(12) United States Patent
Desai et al.

(10) Patent No.: US 12,324,860 B2
(45) Date of Patent: *Jun. 10, 2025

(54) METHODS OF TREATING CENTRAL NERVOUS SYSTEM DISORDERS VIA ADMINISTRATION OF NANOPARTICLES OF AN mTOR INHIBITOR AND AN ALBUMIN

(71) Applicant: Abraxis BioScience, LLC, Summit, NJ (US)

(72) Inventors: Neil P. Desai, Pacific Palisades, CA (US); Shihe Hou, Millington, NJ (US)

(73) Assignee: Abraxis BioScience, LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/441,673

(22) Filed: Feb. 14, 2024

(65) Prior Publication Data
US 2024/0299313 A1    Sep. 12, 2024

Related U.S. Application Data

(63) Continuation of application No. 17/024,482, filed on Sep. 17, 2020, now Pat. No. 11,944,708, which is a
(Continued)

(51) Int. Cl.
*A61K 9/51* (2006.01)
*A61K 9/00* (2006.01)
(Continued)

(52) U.S. Cl.
CPC .......... *A61K 9/5169* (2013.01); *A61K 9/0019* (2013.01); *A61K 31/436* (2013.01); *A61K 39/3955* (2013.01); *A61P 25/08* (2018.01)

(58) Field of Classification Search
None
See application file for complete search history.

(56) References Cited

U.S. PATENT DOCUMENTS

| | | |
|---|---|---|
| 5,362,478 A | 11/1994 | Desai |
| 5,439,686 A | 8/1995 | Desai |
| (Continued) | | |

FOREIGN PATENT DOCUMENTS

| | | |
|---|---|---|
| AU | 2015271950 A1 | 2/2016 |
| EP | 0393457 B1 | 7/1994 |
| (Continued) | | |

OTHER PUBLICATIONS

Citraro, R., et al., mTOR pathway inhibition as a new therapeutic strategy in epilepsy and epileptogenesis, Pharm. Res., 107 (2016) pp. 333-343. (Year: 2016).*

(Continued)

*Primary Examiner* — Dominic Lazaro
(74) *Attorney, Agent, or Firm* — MORRISON & FOERSTER LLP

(57) ABSTRACT

The present application provides methods of treating a CNS disorder (such as glioblastoma and epilepsy) in an individual, comprising systemically (e.g., intravenously or subcutaneously) administering to the individual an effective amount of a composition comprising nanoparticles comprising an mTOR inhibitor (such as a limus drug, such as sirolimus or a derivative thereof) and an albumin, optionally further comprising administering a second agent (such as an anti-VEGF antibody, a proteasome inhibitor, or an alkylating agent).

20 Claims, 16 Drawing Sheets

Related U.S. Application Data continuation of application No. PCT/US2019/023037, filed on Mar. 19, 2019.

(60) Provisional application No. 62/645,634, filed on Mar. 20, 2018, provisional application No. 62/815,346, filed on Mar. 7, 2019.

(51) Int. Cl.
*A61K 31/436* (2006.01)
*A61K 39/395* (2006.01)
*A61P 25/08* (2006.01)

(56) References Cited

U.S. PATENT DOCUMENTS

| | | |
|---|---|---|
| 5,498,421 A | 3/1996 | Grinstaff |
| 5,505,932 A | 4/1996 | Grinstaff |
| 5,508,021 A | 4/1996 | Grinstaff |
| 5,512,268 A | 4/1996 | Grinstaff |
| 5,560,933 A | 10/1996 | Soon-shiong |
| 5,635,207 A | 6/1997 | Grinstaff |
| 5,639,473 A | 6/1997 | Grinstaff |
| 5,650,156 A | 7/1997 | Grinstaff |
| 5,665,382 A | 9/1997 | Grinstaff |
| 5,665,383 A | 9/1997 | Grinstaff |
| 5,916,596 A | 6/1999 | Desai |
| 5,997,904 A | 12/1999 | Magdassi |
| 6,096,331 A | 8/2000 | Desai |
| 6,506,405 B1 | 1/2003 | Desai |
| 6,528,067 B1 | 3/2003 | Magdassi |
| 6,537,579 B1 | 3/2003 | Desai |
| 6,565,842 B1 | 5/2003 | Sojomihardjo |
| 6,652,884 B2 | 11/2003 | Falciani |
| 6,749,868 B1 | 6/2004 | Desai |
| 6,753,006 B1 | 6/2004 | Desai |
| 7,758,891 B2 | 7/2010 | Desai |
| 7,771,751 B2 | 8/2010 | Desai |
| 7,780,984 B2 | 8/2010 | Desai |
| 7,820,788 B2 | 10/2010 | Desai |
| 7,923,536 B2 | 4/2011 | Desai |
| 7,981,445 B2 | 7/2011 | De |
| 8,034,375 B2 | 10/2011 | Desai |
| 8,034,765 B2 | 10/2011 | De |
| 8,137,684 B2 | 3/2012 | Desai |
| 8,138,229 B2 | 3/2012 | Desai |
| 8,257,733 B2 | 9/2012 | Desai |
| 8,268,348 B2 | 9/2012 | Desai |
| 8,314,156 B2 | 11/2012 | Desai |
| 8,735,394 B2 | 5/2014 | Desai |
| 8,846,771 B2 | 9/2014 | Desai |
| 8,853,260 B2 | 10/2014 | Desai |
| 8,911,786 B2 | 12/2014 | Desai |
| 8,927,019 B2 | 1/2015 | Desai |
| 8,999,396 B2 | 4/2015 | Desai |
| 9,012,518 B2 | 4/2015 | Desai |
| 9,012,519 B2 | 4/2015 | Desai |
| 9,061,014 B2 | 6/2015 | Seward |
| 9,101,543 B2 | 8/2015 | Desai |
| 9,149,455 B2 | 10/2015 | Desai |
| 9,308,180 B2 | 4/2016 | De |
| 9,370,494 B2 | 6/2016 | Yeo |
| 9,393,318 B2 | 7/2016 | Desai |
| 9,399,071 B2 | 7/2016 | Desai |
| 9,399,072 B2 | 7/2016 | Desai |
| 9,446,003 B2 | 9/2016 | Desai |
| 9,511,046 B2 | 12/2016 | Desai |
| 9,561,288 B2 | 2/2017 | Desai |
| 9,585,960 B2 | 3/2017 | Foss |
| 9,597,409 B2 | 3/2017 | Desai |
| 9,675,578 B2 | 6/2017 | Desai |
| 9,724,323 B2 | 8/2017 | Desai |
| 9,820,949 B2 | 11/2017 | Desai |
| 9,855,220 B2 | 1/2018 | Desai |
| 9,884,013 B2 | 2/2018 | Seward |
| 9,962,373 B2 | 5/2018 | Desai et al. |
| 10,076,501 B2 | 9/2018 | Foss et al. |
| 10,206,887 B2 | 2/2019 | Desai |
| 10,258,565 B2 | 4/2019 | Seward |
| 10,328,031 B2 | 6/2019 | Desai |
| 10,413,531 B2 | 9/2019 | Desai |
| 10,527,604 B1 | 1/2020 | Peykov |
| 10,555,912 B2 | 2/2020 | Foss |
| 10,660,965 B2 | 5/2020 | Desai |
| 10,682,420 B2 | 6/2020 | Desai |
| 10,705,070 B1 | 7/2020 | Peykov |
| 10,744,110 B2 | 8/2020 | Desai |
| 10,900,951 B1 | 1/2021 | Peykov |
| 10,973,806 B2 | 4/2021 | Desai |
| 11,320,416 B1 | 5/2022 | Peykov et al. |
| 11,497,737 B2 | 11/2022 | Desai |
| 11,944,708 B2 * | 4/2024 | Desai .................. A61K 39/395 |
| 12,061,183 B2 | 8/2024 | Peykov |
| 2003/0185894 A1 | 10/2003 | Zenoni |
| 2003/0187062 A1 | 10/2003 | Zenoni |
| 2003/0199425 A1 | 10/2003 | Desai |
| 2005/0004002 A1 | 1/2005 | Desai |
| 2006/0241056 A1 | 10/2006 | Orlowski et al. |
| 2006/0263434 A1 | 11/2006 | Desai |
| 2007/0082838 A1 | 4/2007 | De |
| 2007/0087022 A1 | 4/2007 | Desai |
| 2007/0093547 A1 | 4/2007 | Desai |
| 2007/0116761 A1 | 5/2007 | Desai |
| 2007/0116774 A1 | 5/2007 | Desai |
| 2007/0117744 A1 | 5/2007 | Desai |
| 2007/0128290 A1 | 6/2007 | Desai |
| 2008/0063724 A1 | 3/2008 | Desai |
| 2008/0160095 A1 | 7/2008 | Desai |
| 2008/0161382 A1 | 7/2008 | Desai |
| 2008/0280987 A1 | 11/2008 | Desai |
| 2009/0098210 A1 | 4/2009 | Desai |
| 2009/0130163 A1 | 5/2009 | Desai |
| 2009/0196933 A1 | 8/2009 | De |
| 2009/0263483 A1 | 10/2009 | Desai |
| 2009/0304805 A1 | 12/2009 | Desai |
| 2010/0035800 A1 | 2/2010 | Desai |
| 2010/0048499 A1 | 2/2010 | Desai |
| 2010/0112077 A1 | 5/2010 | Desai |
| 2010/0166869 A1 | 7/2010 | Desai |
| 2010/0183728 A1 | 7/2010 | Desai |
| 2010/0196490 A1 | 8/2010 | Desai |
| 2010/0215751 A1 | 8/2010 | Desai |
| 2010/0226996 A1 | 9/2010 | Desai |
| 2010/0291584 A1 | 11/2010 | Tseng et al. |
| 2010/0297243 A1 | 11/2010 | Desai |
| 2011/0052708 A1 | 3/2011 | Soon-shiong |
| 2011/0118342 A1 | 5/2011 | De |
| 2011/0151012 A1 | 6/2011 | Desai |
| 2011/0165256 A1 | 7/2011 | Desai |
| 2011/0196026 A1 | 8/2011 | De |
| 2011/0301248 A1 | 12/2011 | Desai |
| 2012/0004177 A1 | 1/2012 | Desai |
| 2012/0070502 A1 | 3/2012 | Desai |
| 2012/0076862 A1 | 3/2012 | Desai |
| 2012/0128732 A1 | 5/2012 | Trieu |
| 2012/0177743 A1 | 7/2012 | Desai |
| 2012/0189701 A1 | 7/2012 | Desai |
| 2012/0231082 A1 | 9/2012 | Desai |
| 2012/0283205 A1 | 11/2012 | Desai |
| 2012/0308612 A1 | 12/2012 | De |
| 2013/0005678 A1 | 1/2013 | Sandvold |
| 2013/0045240 A1 | 2/2013 | Tao |
| 2013/0071438 A1 | 3/2013 | Desai |
| 2013/0115296 A1 | 5/2013 | Yeo |
| 2013/0195922 A1 | 8/2013 | Desai |
| 2013/0195983 A1 | 8/2013 | Desai |
| 2013/0195984 A1 | 8/2013 | Desai |
| 2013/0202709 A1 | 8/2013 | Desai |
| 2013/0209518 A1 | 8/2013 | Desai |
| 2013/0244952 A1 | 9/2013 | Desai |
| 2013/0266659 A1 | 10/2013 | Desai |
| 2013/0280336 A1 | 10/2013 | Desai |
| 2013/0280337 A1 | 10/2013 | Desai |
| 2014/0017315 A1 | 1/2014 | Desai |

(56) References Cited

U.S. PATENT DOCUMENTS

| | | |
|---|---|---|
| 2014/0017316 A1 | 1/2014 | Desai |
| 2014/0017323 A1 | 1/2014 | Desai |
| 2014/0023717 A1 | 1/2014 | Desai |
| 2014/0039069 A1 | 2/2014 | Desai |
| 2014/0039070 A1 | 2/2014 | Desai |
| 2014/0056986 A1 | 2/2014 | Desai |
| 2014/0072630 A1 | 3/2014 | Tao |
| 2014/0072631 A1 | 3/2014 | Trieu |
| 2014/0072643 A1 | 3/2014 | Desai |
| 2014/0079787 A1 | 3/2014 | Yeo |
| 2014/0079788 A1 | 3/2014 | Desai |
| 2014/0079793 A1 | 3/2014 | Desai |
| 2014/0080901 A1 | 3/2014 | Desai |
| 2014/0134257 A1 | 5/2014 | Desai |
| 2014/0155344 A1 | 6/2014 | Desai |
| 2014/0170228 A1 | 6/2014 | Desai |
| 2014/0186447 A1 | 7/2014 | Desai |
| 2014/0199403 A1 | 7/2014 | Desai |
| 2014/0199404 A1 | 7/2014 | Heise |
| 2014/0199405 A1 | 7/2014 | Pierce |
| 2014/0271871 A1 | 9/2014 | Desai |
| 2014/0296279 A1 | 10/2014 | Seward |
| 2014/0296353 A1 | 10/2014 | Desai |
| 2014/0302157 A1 | 10/2014 | Desai |
| 2015/0050356 A1 | 2/2015 | Desai |
| 2015/0065781 A1 | 3/2015 | Bais et al. |
| 2015/0079177 A1 | 3/2015 | Desai |
| 2015/0079181 A1 | 3/2015 | Desai |
| 2015/0104521 A1 | 4/2015 | Desai |
| 2015/0111960 A1 | 4/2015 | Desai |
| 2015/0157722 A1 | 6/2015 | Foss |
| 2015/0165047 A1 | 6/2015 | Desai |
| 2015/0190519 A1 | 7/2015 | Desai |
| 2015/0190556 A1 | 7/2015 | Desai |
| 2015/0313866 A1 | 11/2015 | Desai |
| 2016/0008330 A1 | 1/2016 | Desai |
| 2016/0015681 A1 | 1/2016 | Desai |
| 2016/0015817 A1 | 1/2016 | Benettaib |
| 2016/0151325 A1 | 6/2016 | Desai |
| 2016/0228401 A1 | 8/2016 | Desai |
| 2016/0374952 A1 | 12/2016 | Yeo |
| 2017/0007569 A1 | 1/2017 | De |
| 2017/0014373 A1 | 1/2017 | Desai |
| 2017/0020824 A1 | 1/2017 | Desai |
| 2017/0049711 A1 | 2/2017 | Desai |
| 2017/0100344 A1 | 4/2017 | Desai |
| 2017/0105951 A1 | 4/2017 | Desai |
| 2017/0157035 A1 | 6/2017 | Seward |
| 2017/0172975 A1 | 6/2017 | Desai |
| 2017/0181988 A1 | 6/2017 | Malhotra |
| 2017/0202782 A1 | 7/2017 | Pierce |
| 2017/0203012 A1 | 7/2017 | Desai |
| 2017/0224627 A1 | 8/2017 | Foss |
| 2017/0333384 A1 | 11/2017 | Desai |
| 2017/0340599 A1 | 11/2017 | Desai |
| 2018/0015181 A1 | 1/2018 | Desai |
| 2018/0064679 A1 | 3/2018 | Pierce |
| 2018/0133157 A1 | 5/2018 | Desai |
| 2018/0147139 A1 | 5/2018 | Seward |
| 2018/0153820 A1 | 6/2018 | Desai |
| 2018/0153863 A1 | 6/2018 | Desai |
| 2018/0169017 A1 | 6/2018 | Desai |
| 2018/0177770 A1 | 6/2018 | Desai |
| 2018/0177771 A1 | 6/2018 | Desai |
| 2018/0214425 A1 | 8/2018 | Desai |
| 2018/0256551 A1 | 9/2018 | Desai et al. |
| 2018/0289620 A1 | 10/2018 | Desai et al. |
| 2018/0374583 A1 | 12/2018 | Goldstein |
| 2019/0022020 A1 | 1/2019 | Desai |
| 2019/0054033 A1 | 2/2019 | Foss |
| 2019/0147986 A1 | 5/2019 | Luo |
| 2019/0167629 A1 | 6/2019 | Desai |
| 2019/0175564 A1 | 6/2019 | Desai |
| 2019/0183789 A1 | 6/2019 | Seward |
| 2019/0184031 A1 | 6/2019 | Desai |
| 2019/0192477 A1 | 6/2019 | Desai |
| 2019/0247357 A1 | 8/2019 | Foss |
| 2019/0307732 A1 | 10/2019 | Desai |
| 2019/0343789 A1 | 11/2019 | Desai |
| 2020/0040398 A1 | 2/2020 | Desai |
| 2020/0129469 A1 | 4/2020 | Renschler |
| 2020/0138793 A1 | 5/2020 | Desai |
| 2020/0246275 A1 | 8/2020 | Pierce |
| 2020/0316216 A1 | 10/2020 | Desai |
| 2021/0000752 A1 | 1/2021 | Desai |
| 2021/0085621 A1 | 3/2021 | Desai et al. |
| 2021/0137848 A1 | 5/2021 | Desai et al. |
| 2021/0315823 A1 | 10/2021 | Desai et al. |
| 2021/0322335 A1 | 10/2021 | Desai et al. |
| 2021/0322391 A1 | 10/2021 | Desai |
| 2022/0054404 A1 | 2/2022 | Desai et al. |
| 2023/0000844 A1 | 1/2023 | Desai et al. |
| 2023/0080409 A1 | 3/2023 | Desai |
| 2023/0190715 A1 | 6/2023 | Desai |
| 2023/0243806 A1 | 8/2023 | Peykov et al. |
| 2023/0263779 A1 | 8/2023 | Desai |
| 2023/0293449 A1 | 9/2023 | Desai et al. |
| 2024/0009323 A1 | 1/2024 | Desai |
| 2024/0065984 A1 | 2/2024 | Desai |
| 2024/0082224 A1 | 3/2024 | Desai |

FOREIGN PATENT DOCUMENTS

| | | |
|---|---|---|
| EP | 0363284 B1 | 5/1997 |
| EP | 0364344 B1 | 5/1998 |
| JP | 2013511549 A | 4/2013 |
| WO | 198810266 A1 | 12/1988 |
| WO | 199113904 A1 | 9/1991 |
| WO | 199212140 A1 | 7/1992 |
| WO | 199418954 A1 | 9/1994 |
| WO | 199814174 A1 | 4/1998 |
| WO | 199814175 A1 | 4/1998 |
| WO | 199900113 A1 | 1/1999 |
| WO | 200064437 A1 | 11/2000 |
| WO | 200071079 A2 | 11/2000 |
| WO | 200113904 A2 | 3/2001 |
| WO | 200113904 A3 | 6/2001 |
| WO | 200189522 A1 | 11/2001 |
| WO | 2002087545 A1 | 11/2002 |
| WO | 2003096944 A1 | 11/2003 |
| WO | 2004004749 A1 | 1/2004 |
| WO | 2004052401 A2 | 6/2004 |
| WO | 2004052401 A3 | 2/2005 |
| WO | 2006089207 A2 | 8/2006 |
| WO | 2006089290 A1 | 8/2006 |
| WO | 2007027819 A2 | 3/2007 |
| WO | 2007027941 A2 | 3/2007 |
| WO | 2007027819 A3 | 4/2007 |
| WO | 2007027941 A3 | 4/2007 |
| WO | 2006089207 A3 | 5/2007 |
| WO | 200071079 A3 | 3/2008 |
| WO | 2008027055 A1 | 3/2008 |
| WO | 2008057562 A1 | 5/2008 |
| WO | 2008076373 A1 | 6/2008 |
| WO | 2008109163 A1 | 9/2008 |
| WO | 2008137148 A2 | 11/2008 |
| WO | 2008150532 A1 | 12/2008 |
| WO | 2008137148 A3 | 2/2009 |
| WO | 2009112022 A2 | 9/2009 |
| WO | 2009124119 A2 | 10/2009 |
| WO | 2009126175 A1 | 10/2009 |
| WO | 2009126401 A1 | 10/2009 |
| WO | 2009126938 A1 | 10/2009 |
| WO | 2010068925 A1 | 6/2010 |
| WO | 2010105172 A1 | 9/2010 |
| WO | 2010118365 A1 | 10/2010 |
| WO | 2010121000 A1 | 10/2010 |
| WO | 2010129622 A1 | 11/2010 |
| WO | 2011025838 A1 | 3/2011 |
| WO | 2011063309 A1 | 5/2011 |
| WO | 2011119988 A1 | 9/2011 |
| WO | 2011123393 A1 | 10/2011 |
| WO | 2011123395 A1 | 10/2011 |
| WO | 2011153009 A1 | 12/2011 |

(56) References Cited

FOREIGN PATENT DOCUMENTS

| | | | |
|---|---|---|---|
| WO | 2011153010 A1 | 12/2011 | |
| WO | 2011156119 A1 | 12/2011 | |
| WO | 2012149451 A1 | 11/2012 | |
| WO | 2013090634 A1 | 6/2013 | |
| WO | 2014105644 A1 | 7/2014 | |
| WO | 2014110345 A1 | 7/2014 | |
| WO | 2014110408 A1 | 7/2014 | |
| WO | 2014110443 A1 | 7/2014 | |
| WO | 2014123612 A1 | 8/2014 | |
| WO | 2014143613 A1 | 9/2014 | |
| WO | 2014151853 A1 | 9/2014 | |
| WO | 2014159171 A1 | 10/2014 | |
| WO | 2015157120 A1 | 10/2015 | |
| WO | 2016057712 A1 | 4/2016 | |
| WO | 2016141365 A1 | 9/2016 | |
| WO | 2017004249 A1 | 1/2017 | |
| WO | 2017004266 A1 | 1/2017 | |
| WO | 2017004267 A1 | 1/2017 | |
| WO | WO-2017004264 A1 * | 1/2017 | ......... A61K 31/4188 |
| WO | 2017201189 A1 | 11/2017 | |
| WO | 2018064405 A1 | 4/2018 | |
| WO | 2018067943 A1 | 4/2018 | |
| WO | 2018071399 A1 | 4/2018 | |
| WO | 2019126223 A1 | 6/2019 | |
| WO | 2019183146 A1 | 9/2019 | |
| WO | 2019226685 A1 | 11/2019 | |
| WO | 2020191053 A1 | 9/2020 | |
| WO | 2021086946 A1 | 5/2021 | |
| WO | 2021096997 A1 | 5/2021 | |

OTHER PUBLICATIONS

Adams, J. (May 2004). "The Proteasome: A Suitable Antineoplastic Target," J. Nat. Rev. Cancer 4:349-360.
Altmayer, P. et al. (1995). "Propofol Binding to Human Blood Proteins," Arzneimittelforschung 45:1053-1056.
Angliker, H. et al. (1987). "The Synthesis of Lysyifluoromethanes and Their Properties as Inhibitors of Trypsin, Plasmin and Cathepsin B," Biochem. J. 241:871-875.
Badesch, D. B. et al. (2010). "Pulmonary Arterial Hypertension: Baseline Characteristics From the REVEAL Registry," Chest 137(2):376-387.
Barry, W. T. et al. (2005, e-pub. Jan. 10, 2005). "Significance Analysis of Functional Categories in Gene Expression Studies: A Structured Permutation Approach," Bioinformatics 21(9):1943-1949.
Bussemaker, H. J. et al. (Sep. 27, 2007). "Dissecting Complex Transcriptional Responses Using Pathway-Level Scores Based on Prior Information," BMC Bioinformatics 8(Suppl. 6): S6, 7 pages.
Calatozzolo, C., et al. (2012, e-pub. Jul. 26, 2012). "Multidrug Resistance Proteins Expression in Glioma Patients with Epilepsy," J. Neurooncol. 110:129-135.
Cancer Genome Atlas Research. (2013). "Comprehensive Molecular Characterization of Clear Cell Renal Cell Carcinoma," Nature 499:43-49, 19 pages.
Carter, D.C. et al. (1994). "Structure of Serum Albumin," Adv. Protein. Chem. 45:153-203.
Citraro, R. et al. (2016, e-pub. Apr. 2, 2016). "mTOR Pathway Inhibition as a New Therapeutic Strategy in Epilepsy and Epileptogenesis," Pharmacological Research 107:333 to 343.
Curatolo, P. et al. (2016, e-pub. Feb. 29, 2016). "The Role of mTOR Inhibitors in the Treatment of Patients with Tuberous Sclerosis Complex: Evidence-Based and Expert Opinions," Drugs 76:551-565.
Curry, S. et al. (Sep. 1998). "Crystal Structure of Human Serum Albumin Complexed With Fatty Acid Reveals an Asymmetric Distribution of Binding Sites," Nat. Struct. Biol. 5(9):827-835.
Dickson, M.A. et al. (Apr. 1, 2013). "Extrarenal Perivascular Epithelioid Cell Tumors (PEComas) Respond to mTOR Inhibition: Clinical and Molecular Correlates," International Journal of Cancer 132(7):1711-1717.

English language translation of WO 2009/112022 A2. (Year: 2009).
European Search Report mailed on Jan. 20, 2022, for European Patent Application No. 19770483.6, filed on Oct. 15, 2020, 7 pages.
Fang, Y. et al. (Nov. 30, 2001). "Phosphatidic Acid-Mediated Mitogenic Activation of mTOR Signaling," Science 294(5548):1942-1945.
Fehske, K.J. et al. (1981). "The Location of Drug Binding Sites in Human Serum Albumin," Biochem. Pharmcol. 30 (7):687-692.
Ferrara, N. (1999). "Molecular and Biological Properties of Vascular Endothelial Growth Factor," J. Mol. Med. 77:527-543.
Ferrara, N. et al. (Feb. 1997). "The Biology of Vascular Endothelial Growth Factor," Endocrine Rev. 18(1):4-25.
Finlayson, J.S. (1980). "Albumin Products," Seminars in Thrombosis and Hemostasis 6(2):85-120.
Garrido, M.J. et al. (Nov.-Dec. 1994). "Characterization of Propofol Binding to Plasma Proteins and Possible Interaction," Rev. Esp. Anestestiol. Reanim. 41(6):308-312. (English Translation of Abstract Only.).
Gonzalez-Angulo, A.M. et al. (Oct. 1, 2013). "Weekly nab-Rapamycin in Patients With Advanced Nonhematologic Malignancies: Final Results of a Phase I Trial," Clinical Cancer Research 19(19):5474-5484, 21 pages.
Goodman, L.S. et al. (1996). Goodman & Gilman's The Pharmacological Basis of Therapeutics, 9th Edition, New York, McGraw-Hill, Health Professions Divisions, pp. v-xii, (Table of Contents Only.).
Grabiner, B.C. et al. (May 2014). "A Diverse Array of Cancer-Associated mTOR Mutation are Hyperactivating and Can Predict Rapamycin Sensitivity," Cancer Discovery 4:554-563.
Green, G.D.J. et al. (Feb. 25, 1981). "Peptidyl Diazomethyl Ketones Are Specific Inactivators of Thiol Proteinases," J. Biol. Chem. 256(4):1923-1928.
Hanif, F. et al. (2017). "Glioblastoma Multiforme: A Review of its Epidemiology and Pathogenesis through Clinical Presentation and Treatment," Asian Pacific Journal of Cancer Prevention 18(1):3-9.
Hansel, D.E. et al. (Jun. 2010). "Mammalian Target of Rapamycin (mTOR) Regulates Cellular Proliferation and Tumor Growth in Urothelial Carcinoma," The American Journal of Pathology 176(6):3062-3072.
Hauser, C.J. et al. (Jun. 1980). "Oxygen Transport Responses to Colloids and Cystalloids in Critically Ill Surgical Patients," Surgery, Gynecology and Obstetrics 150(6):811-816.
He, X.M. et al. (Jul. 16, 1992). "Atomic Structure and Chemistry of Human Serum Albumin," Nature 358:209-215.
Houck, K.A. et al. (Dec. 1991). "The Vascular Endothelial Growth Factor Family: Identification of a Fourth Molecular Species and Characterizaion of Alternative Splicing of RNA," Mol. Endocrin. 5(12):1806-1814.
International Preliminary Report on Patentability mailed on Oct. 1, 2020, for PCT Patent Application No. PCT/US2019/023037, filed on Mar. 19, 2019, 11 pages.
International Search Report and Written Opinion mailed on May 22, 2019, for P*CT Patent Application No. PCT/US2019/023037, filed on Mar. 19, 2019, 15 pages.
Iyer, G. et al. (Oct. 12, 2012). "Genome Sequencing Identifies a Basis for Everolimus Sensitivity," Science 338 (6104):221.
Jacinto, E. et al. (Nov. 2004, e-pub. Oct. 3, 2004). "Mammalian TOR Complex 2 Controls the Actin Cytoskeleton and is Rapamycin Insensitive," Nat. Cell Biol. 6(11):1122-1128, Supplementary Information pp. 1-3, total 10 pages.
Joazeiro, C. et al. (Aug. 15, 2006). "Proteasome Inhibitor Drugs on the Rise," Cancer Res. 66(16):7840-7842.
Kabat, J. et al. (2012). "Focal Cortical Dysplasia—Review," Pol. J. Radiol. 77(2):35-43.
Kerbel, R.S. (Mar. 2000). "Tumor Angiogenesis: Past, Present, and the Near Future," Carcinogenesis 21 (3):505-515.
Kim, D-H. et al. (Jul. 26, 2002). "mTOR Interacts with Raptor to Form a Nutrient-Sensitive Complex that Signals to the Cell Growth Machinery," Cell 110:163-175.
Kim, J.C. et al. (2001). "The Limits of Bacillus Calmette-Guerin for Carcinoma in Situ of the Bladder," The Journal of Urology 165(3):745-756.

(56) References Cited

OTHER PUBLICATIONS

Kisselev, A.L. et al. (2001, e-pub. Jul. 12, 2001). "Proteasome Inhibitors: From Research Tools to Drug Candidates," Chem. Biol. 8(8):739-758.

Knight, Z.A. et al. (May 19, 2006). "A Pharmacological Map of the PI3-K Family Defines a Role for p110a in Insulin Signaling," Cell 125:733-747.

Kragh-Hansen, U. (Feb. 1990). "Structure and Ligand Binding Properties of Human Serum Albumin," Dan. Med. Bull. 37(1):57-84.

Krymskaya, V.P. et al. (2011). "mTOR is Required for Pulmonary Arterial Vascular Smooth Muscle Cell Proliferation Under Chronic Hypoxia," The FASEB Journal 25(6):1922-1933.

Legendre, C. et al. (2003). "Cardiovascular Risk Factors of Sirolimus Compared With Cyclosporine: Early Experience From Two Randomized Trials in Renal Transplantation," Transplantation proceedings 35(3 Suppl):151S-153S.

Leung, D.W. et al. (Dec. 8, 1989). "Vascular Endothelial Growth Factor is a Secreted Angiogenic Mitogen," Science 246:1306-1309.

Lim, S.M. et al. (May 20, 2015). "Next-Generation Sequencing to Reveal Somatic Mutations That Confer Sensitivity to Everolimus," J Clin. Onocl. 33(15): Abstract No. 11010, 3 pages.

Lin, F. et al. (2013). "Dual mTORC1 and mTORC2 Inhibitor Palomid 529 Penetrates the Blood-brain Barrier Without Restriction by ABCB1 and ABCG2," In J. Cancer 133(5):1222-1234.

Lyden, D. et al. (2001). "Impaired Recruitment of Bone-Marrow-Derived Endothelial and Hematopoietic Precursor Cells Blocks Tumor Angiogenesis and Growth." Nat. Med. 7:1194-1201.

Maglietta, R. et al. (2007, e-pub. May 31, 2007). "Statistical Assessment of Functional Categories of Genes Deregulated in Pathological Conditions by Using Microarray Data," Bioinformatics 23:2063-2072.

Manton, C.A. et al. (Jan. 25, 2016). "Induction of Cell Death by the Novel Proteasome Inhibitor Marizomib in Glioblastoma in Vitro and in Vivo," Scientific Reports, 6(18953):1-16.

McKiernan, J.M. et al. (2010). "Phase II Trial of Intracesical Nanoparticle Albumin-Bound (nab-) Paclitaxel for the Treatment of Non-Muscle Invasive Urothelial Carcinoma of the Bladder after BCG Treatment Failure," The Journal of Urology 183(Suppl. 4): 22 pages.

Muller, B.G. et al. (1996). "Albumin Nanospheres as Carriers for Passive Drug Targeting: An Optimized Manufacturing Technique," Pharmaceutical Research 13(1):32-37.

Novak, B.A. et al. (2006, e-pub. Nov. 8, 2005). Pathway Recognition and Augmentation by Computational Analysis of Microarray Expression Data, Bioinformatics 22(2):233-241.

Parkes, C. et al. (Sep. 1, 1985). "Calpain Inhibition by Peptide Epoxides," Biochem. J. 230:509-516.

Paal, K. et al. (2001). "High Affinity Binding of Paclitaxel to Human Serum Albumin," Eur. J. Biochem. 268 (7):2187-2191.

Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.

Purcell, M. et al. (2000). "Interaction of Taxol With Human Serum Albumin," Biochim. Biophys. Acta. 1478:61-68.

Roper, J. et al. (Sep. 26, 2011). "The Dual PI3K/mTOR Inhibitor NVP-BEZ235 Induces Tumor Regression in a Genetically Engineered Mouse Model of PIK3CA Wild-Type Colorectal Cancer," PLoS One 6(9):e25132, 10 pages.

Sarbassov, D.D. et al. (Jul. 27, 2004). "Rictor, a Novel Binding Partner of mTOR, Defines a Rapamycin-Insensitive and Raptor Independent Pathway that Regulates the Cytoskeleton," Curr. Biol. 14:1296-1302.

Seager, C.M. et al. (Dec. 1, 2009). "Intravesical Delivery of Rapamycin Suppresses Tumorigenesis in a Mouse Model of Progressive Bladder Cancer," Cancer Prevention Research 2(12):1008-1014.

Segal, E. et al. (Jun. 2003). "Module Networks: Identifying Regulatory Modules and Their Condition-Specific Regulators From Gene Expression Data," Nat. Genet. 34(2):166-176.

Segal, E. et al. (Oct. 2004, e-pub. Sep. 26, 2004) "A Module Map Showing Conditional Activity of Expression Modules in Cancer," Nat. Genet. 36(10):1090-1098.

Sirven, J.I. (Sep. 2015). "Epilepsy: A Spectrum Disorder," Cold Spring Harbor Prespect. Med. 5(9):1-16.

Sugio, S. et al. (1999). "Crystal Structure of Human Serum Albumin at 2.5 Å Resolution," Protein. Eng. 12(6):439-446.

Tian, L. et al. (Sep. 20, 2005). "Discovering Statistically Significant Pathways in Expression Profiling Studies," Proc Nat'l Acad Sci USA 102:13544-13549.

Tullis, J.L. (Jan. 24, 1977). "Albumin. 1. Background and Use," JAMA 237(4): 355-360.

Tullis, J.L. (Jan. 31, 1977). "Albumin. 2. Guidelines for Clinical Use," JAMA 237(5):460-463.

Urien, S. et al. (May 1996). "Docetaxel Serum Protein Binding With High Affinity to Alpha-Acid Glycoprotein," Invest. New Drugs 147:147-151.

Verhaak, R.G.W. et al. (Jan. 19, 2010). "Integrated Genomic Analysis Identifies Clinically Relevant Subtypes of Glioblastoma Characterized by Abnormalities in PDGFRA, IDH1, EGFR, and NF1," Cancer Cell 17(1):98-110.

Vlasak, R. et al. (May 1989). "Influenza C Virus Esterase: Analysis of Catalytic Site, Inhibition, and Possible Function," J. VIrol. 63(5):2056-2062.

Vörum, H. (Nov. 1999). "Reversible Ligand Binding to Human Serum Albumin," Dan. Med. Bull. 46(5):379-399.

Wagle, N. et al. (2012). "High-Throughout Detection of Actionable Genomic Alterations in Clinical Tumor Samples by Targeted, Massively Parallel Sequencing," Cancer discovery 2.1:82-93.

Wagle, N. et al. (2014). "Response and Acquired Resistance to Everolimus in Anaplastic Thyroid Cancer," N. Eng. J. Med. 371:1426-1433.

Wagle, N. et al. (May 2014). "Activating mTOR Mutationsin a Patient with an Extraordinary Response on a Phase I Trial of Everolimus and Pazopanib," Cancer Discovery 4:546-553.

Weathers, S-P. et al. (Sep. 2016). "A Randomized Phase II Trial of Standard Dose Bevacizumab Versus Low Dose Bevacizumab Plus Lomustine (CCNU) in Adults With Recurrent Glioblastoma," J. Neurooncol. 129(3):487-494, 16 pages.

European Examination mailed on Jul. 30, 2024, for European Patent Application No. 19770483.6, filed on Oct. 15, 1 2020, 5 pages.

* cited by examiner

FIG. 3

| ABI-009 (mg/kg) | Time (hr) | Brain (ng/g) Mean | Brain (ng/g) SD | Heart (ng/g) Mean | Heart (ng/g) SD | Liver (ng/g) Mean | Liver (ng/g) SD | Lung (ng/g) Mean | Lung (ng/g) SD | Pancreas (ng/g) Mean | Pancreas (ng/g) SD | Blood (ng/ml) Mean | Blood (ng/ml) SD |
|---|---|---|---|---|---|---|---|---|---|---|---|---|---|
| 1.7 (N = 3/group) | 2 | 42.4 | 4.0 | 2244.0 | 82.5 | 3168.0 | 589.5 | 3358.0 | 389.1 | 2350.0 | 616.5 | 58.5 | 1.2 |
| | 8 | 38.2 | 3.6 | 1324.0 | 148.2 | 1564.0 | 137.1 | 2436.0 | 262.3 | 1468.0 | 136.1 | 24.9 | 5.1 |
| | 24 | 40.8 | 13.3 | 595.3 | 145.6 | 502.0 | 262.1 | 1190.0 | 497.5 | 401.3 | 142.2 | 9.6 | 2.9 |
| | 72 | 31.8 | 8.6 | 182.0 | 32.9 | 163.7 | 9.9 | 321.7 | 59.7 | 141.0 | 23.6 | 2.7 | 0.5 |
| | 120 | 94.9 | 4.5 | 100.1 | 25.7 | 76.0 | 21.8 | 170.7 | 53.2 | 79.0 | 55.1 | 1.2 | 0.4 |
| 9.5 (N = 3/group) | 2 | 215.3 | 33.5 | 5082.0 | 1039.4 | 10620.0 | 1803.0 | 5080.0 | 499.5 | 5528.0 | 1714.4 | 560.3 | 106.7 |
| | 8 | 263.7 | 27.6 | 2992.0 | 311.8 | 5138.0 | 1241.2 | 3428.0 | 469.4 | 4060.0 | 1326.7 | 160.3 | 21.5 |
| | 24 | 328.0 | 39.7 | 946.0 | 190.3 | 1014.3 | 408.5 | 1652.0 | 449.1 | 952.0 | 270.5 | 15.1 | 5.6 |
| | 72 | 246.3 | 10.6 | 245.7 | 58.2 | 251.7 | 71.2 | 486.3 | 131.9 | 252.0 | 58.5 | 4.3 | 2.3 |
| | 120 | 225.3 | 54.2 | 96.1 | 15.6 | 95.7 | 29.7 | 165.7 | 21.2 | 84.5 | 47.8 | 1.1 | 0.3 |
| 17 (N = 3/group) | 2 | 568.3 | 84.6 | 8400.0 | 692.0 | 28140.0 | 1478.2 | 9720.0 | 334.1 | 13840.0 | 2160.3 | 1510.0 | 115.3 |
| | 8 | 640.7 | 56.0 | 4980.0 | 579.6 | 9860.0 | 723.3 | 4468.0 | 638.9 | 6728.0 | 1830.9 | 372.7 | 31.5 |
| | 24 | 884.0 | 86.8 | 1496.0 | 359.6 | 2360.0 | 933.6 | 2224.0 | 337.2 | 1380.0 | 351.6 | 34.5 | 15.1 |
| | 72 | 606.0 | 70.7 | 225.7 | 43.4 | 220.0 | 45.4 | 316.3 | 52.8 | 171.7 | 59.5 | 3.0 | 0.7 |
| | 120 | 522.3 | 53.5 | 158.3 | 39.0 | 159.3 | 51.2 | 203.3 | 60.5 | 146.0 | 53.5 | 2.1 | 0.5 |

Group 2 (representative)

METHODS OF TREATING CENTRAL NERVOUS SYSTEM DISORDERS VIA ADMINISTRATION OF NANOPARTICLES OF AN mTOR INHIBITOR AND AN ALBUMIN

CROSS-REFERENCE TO RELATED APPLICATIONS

This application is a continuation application of U.S. patent application Ser. No. 17/024,482, filed Sep. 17, 2020, which is a continuation application of International Application No. PCT/US2019/023037, filed Mar. 19, 2019, which claims priority benefit of U.S. Provisional Application No. 62/645,634 filed Mar. 20, 2018 and U.S. Provisional Application No. 62/815,346 filed Mar. 7, 2019, the entire contents of each of which are hereby incorporated by reference for all purposes.

FIELD OF THE INVENTION

This application pertains to methods and compositions for the treatment of a CNS disorder by administering compositions comprising nanoparticles that comprise an mTOR inhibitor (such as a limus drug, e.g., sirolimus or a derivative thereof) and an albumin alone or in combination with a second agent.

BACKGROUND OF THE INVENTION

Central nervous system diseases, also known as central nervous system disorders, are a spectrum of neurological disorders that affect the structure or function of the brain or spinal cord, which collectively form the central nervous system (CNS). Current treatments include surgeries and prescribed medicines. However, many CNS disorders are difficult to treat because of a natural barrier in the brain.

The mammalian target of rapamycin (mTOR) is a conserved serine/threonine kinase that serves as a central hub of signaling in the cell to integrate intracellular and extracellular signals and to regulate cellular growth and homeostasis. Activation of the mTOR pathway is associated with cell proliferation and survival, while inhibition of mTOR signaling leads to inflammation and cell death. Dysregulation of the mTOR signaling pathway has been implicated in an increasing number of human diseases, including cancer and autoimmune disorders. Consequently, mTOR inhibitors have found wide applications in treating diverse pathological conditions such as cancer, organ transplantation, restenosis, and rheumatoid arthritis.

Sirolimus, also known as rapamycin, is an immunosuppressant drug used to prevent rejection in organ transplantation; it is especially useful in kidney transplants. Sirolimus-eluting stents were approved in the United States to treat coronary restenosis. Additionally, sirolimus has been demonstrated as an effective inhibitor of tumor growth in various cell lines and animal models. Other limus drugs, such as analogs of sirolimus, have been designed to improve the pharmacokinetic and pharmacodynamic properties of sirolimus. For example, Temsirolimus was approved in the United States and Europe for the treatment of renal cell carcinoma. Everolimus was approved in the U. S. for treatment of advanced breast cancer, pancreatic neuroendocrine tumors, advanced renal cell carcinoma, and subependymal giant cell astrocytoma (SEGA) associated with Tuberous Sclerosis. The mode of action of sirolimus is to bind the cytosolic protein FK-binding protein 12 (FKBP12), and the sirolimus-FKBP12 complex in turn inhibits the mTOR pathway by directly binding to the mTOR Complex 1 (mTORC1).

Albumin-based nanoparticle compositions have been developed as a drug delivery system for delivering substantially water insoluble drugs. See, for example, U.S. Pat. Nos. 5,916,596; 6,506,405; 6,749,868, and 6,537,579, 7,820,788, and 7,923,536. Abraxane®, an albumin stabilized nanoparticle formulation of paclitaxel, was approved in the United States in 2005 and subsequently in various other countries for treating metastatic breast cancer, non-small cell lung cancer and pancreatic cancer.

The disclosures of all publications, patents, patent applications and published patent applications referred to herein are hereby incorporated herein by reference in their entirety.

BRIEF SUMMARY OF THE INVENTION

The present application provides methods of treating a CNS disorder (such as epilepsy, cortical dysplasia and glioblastoma) in an individual, comprising systemically administering to the individual an effective amount of a composition comprising nanoparticles comprising an mTOR inhibitor and an albumin. In some embodiments, the amount of the mTOR inhibitor in the nanoparticle composition is from about 0.1 mg/m$^2$ to about 120 mg/m$^2$ for each administration. In some embodiments, the nanoparticle composition is administered once every week, twice every three weeks, or three times every four weeks. In some embodiments, the average diameter of the nanoparticles in the nanoparticle composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated with the albumin. In some embodiments, the nanoparticles comprise the mTOR inhibitor coated with the albumin. In some embodiments, the nanoparticle composition is administered for at least about one to six cycles, wherein each cycle consists of 21 days or 28 days.

In some embodiments according to any one of the methods described herein, the mTOR inhibitor is a limus drug. In some embodiments, the mTOR inhibitor is rapamycin.

In some embodiments according to any one of the methods described herein, the CNS disorder is epilepsy. In some embodiments, the individual has undergone an epilepsy surgery. In some embodiments, the individual has at least 5 seizures in 30 days post epilepsy surgery or does not have a week of seizure freedom following epilepsy surgery. In some embodiments, the method further comprises administering to the individual an effective amount of an anti-epilepsy agent. In some embodiments, the mTOR inhibitor in the nanoparticle composition is from about 0.1 mg/m$^2$ to about 25 mg/m$^2$ for each administration.

In some embodiments according to any one of the methods described herein, the CNS disorder is glioblastoma. In some embodiments, the glioblastoma is recurrent glioblastoma. In some embodiments, the glioblastoma is newly diagnosed glioblastoma. In some embodiments, the individual has undergone surgical resection of newly diagnosed glioblastoma prior to the initiation of the nanoparticle administration.

In some embodiments according to any one of the methods described herein, the method further comprising administering to the individual an effective amount of a second agent selected from the group consisting of an anti-VEGF antibody, an alkylating agent and a proteasome inhibitor. In some embodiments, the amount of the mTOR inhibitor in the nanoparticle composition is from about 20 mg/m² to about 100 mg/m² for each administration. In some embodiments, the second agent is an anti-VEGF antibody. In some embodiments, the anti-VEGF antibody is bevacizumab. In some embodiments, the amount of the anti-VEGF is from about 1 mg/kg to about 5 mg/kg for each administration. In some embodiments, the anti-VEGF antibody is administered once every two weeks. In some embodiments, the anti-VEGF antibody is administered at an amount of less than about 5 mg/kg each week. In some embodiments, the anti-VEGF antibody is administered within an hour of the administration of the nanoparticles. In some embodiments, the second agent is a proteasome inhibitor. In some embodiments, the proteasome inhibitor is marizomib. In some embodiments, the amount of the proteasome inhibitor is about 0.1 mg/m² to about 5.0 mg/m² for each administration. In some embodiments, the proteasome inhibitor is administered three times every four weeks. In some embodiments, the proteasome inhibitor is administered within an hour of the administration of the nanoparticles. In some embodiments, the second agent is an alkylating agent. In some embodiments, the alkylating agent is temozolomide. In some embodiments, the amount of the alkylating agent is about 25 mg/m² to about 100 mg/m². In some embodiments, the amount of the alkylating agent is about 50 mg/m². In some embodiments, the alkylating agent is administered daily. In some embodiments, the alkylating agent is administered daily for at least about three weeks. In some embodiments, the amount of the alkylating agent is about 125 mg/m² to about 175 mg/m² for each administration. In some embodiments, the alkylating agent is administered about 4-6 times every four weeks. In some embodiments, the alkylating agent is administered daily for five consecutive days every four weeks. In some embodiments, the alkylating agent is administered for at least six cycles, wherein each cycle consists of twenty-eight days. In some embodiments, the alkylating agent is administered orally. In some embodiments, the alkylating agent is a nitrosourea compound. In some embodiments, the compound is lomustine. In some embodiments, the amount of the nitrosourea compound is about 80 mg/m² to about 100 mg/m² for each administration. In some embodiments, the nitrosourea compound is administered orally. In some embodiments, the nitrosourea compound is administered once every six weeks.

In some embodiments according to any one of the methods described herein, the method further comprises radiotherapy. In some embodiments, the radiotherapy is a focal radiotherapy. In some embodiments, the focal radiotherapy is administered daily. In some embodiments, about 40-80 Gy focal radiotherapy is administered each week.

In some embodiments according to any one of the methods described herein, the CNS disorder (e.g., the glioblastoma) comprises an mTOR-activation aberration. In some embodiments, the mTOR-activation aberration comprises a PTEN aberration.

In some embodiments according to any one of the methods described herein, wherein the individual is a human.

In some embodiments according to any one of the methods described herein, the nanoparticle composition is parenterally administered into the individual. In some embodiments, the nanoparticle composition is intravenously administered into the individual. In some embodiments, the nanoparticle composition is subcutaneously administered into the individual.

The present application provides kits comprising a nanoparticle composition comprising an mTOR inhibitor and an albumin for treating a CNS disorder. In some embodiments, the kit further comprising an agent selected from the group consisting of an anti-VEGF antibody, an alkylating agent and a proteasome inhibitor. In some embodiments, further comprising an agent for assessing an mTOR-activating aberration.

BRIEF DESCRIPTION OF FIGURES

FIG. 3 provides rapamycin concentrations in blood and different organs following intravenous administration of ABI-009.

Histologic lesions are limited to an aggregate of mixed inflammatory cells (black arrow) within the subcutaneous tissues (SC). The dermis (D) and epidermis (E) are indicated.

Figure 14:
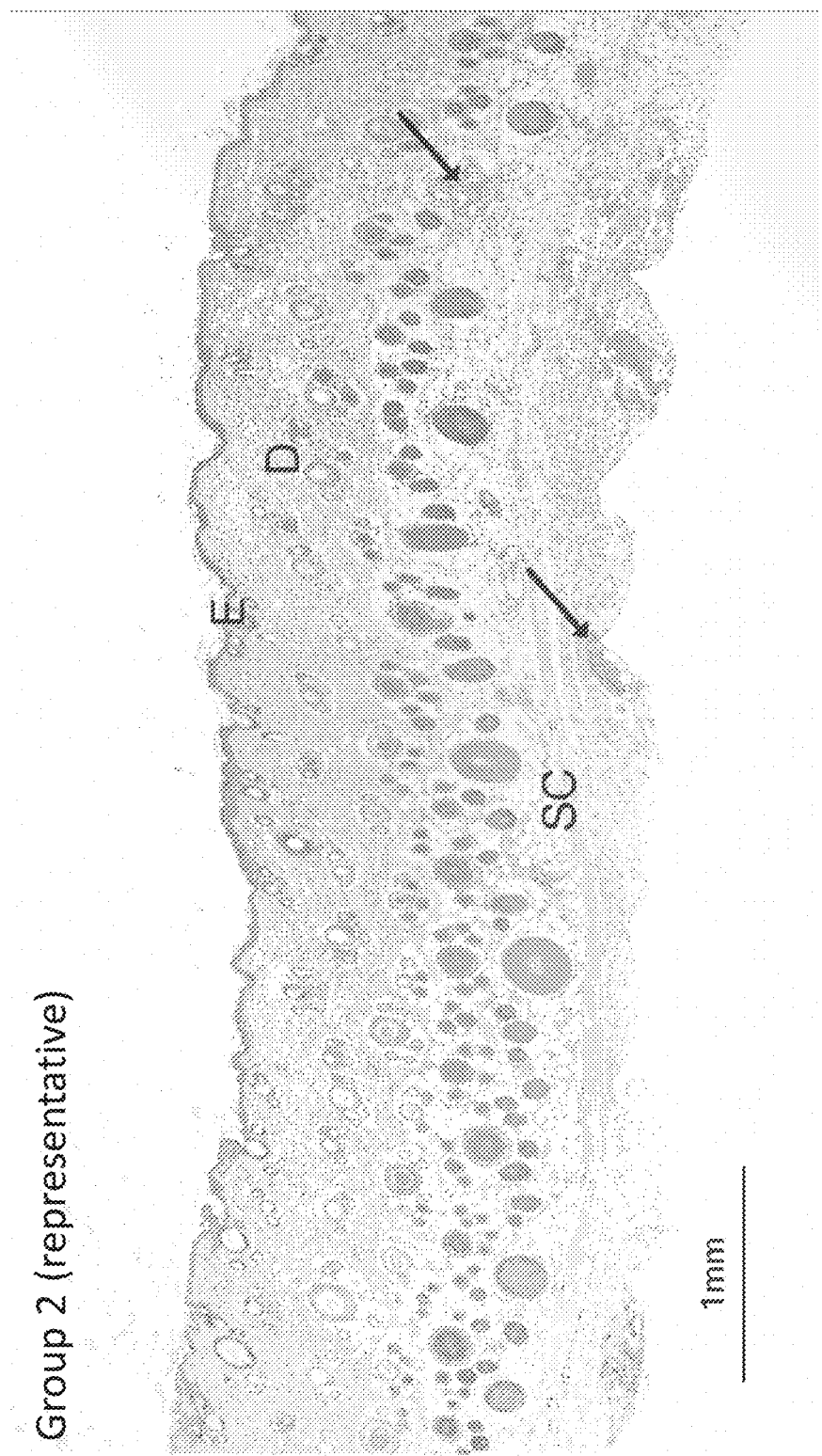

FIG. 14 is a representative histogram image of skin from rat in Group 2 (HSA in 0.9% saline). Multifocal mixed inflammatory cell aggregates (black arrows) are visible within the subcutis (SC). The epidermis (E) and dermis (D) are unremarkable.

Figure 15:
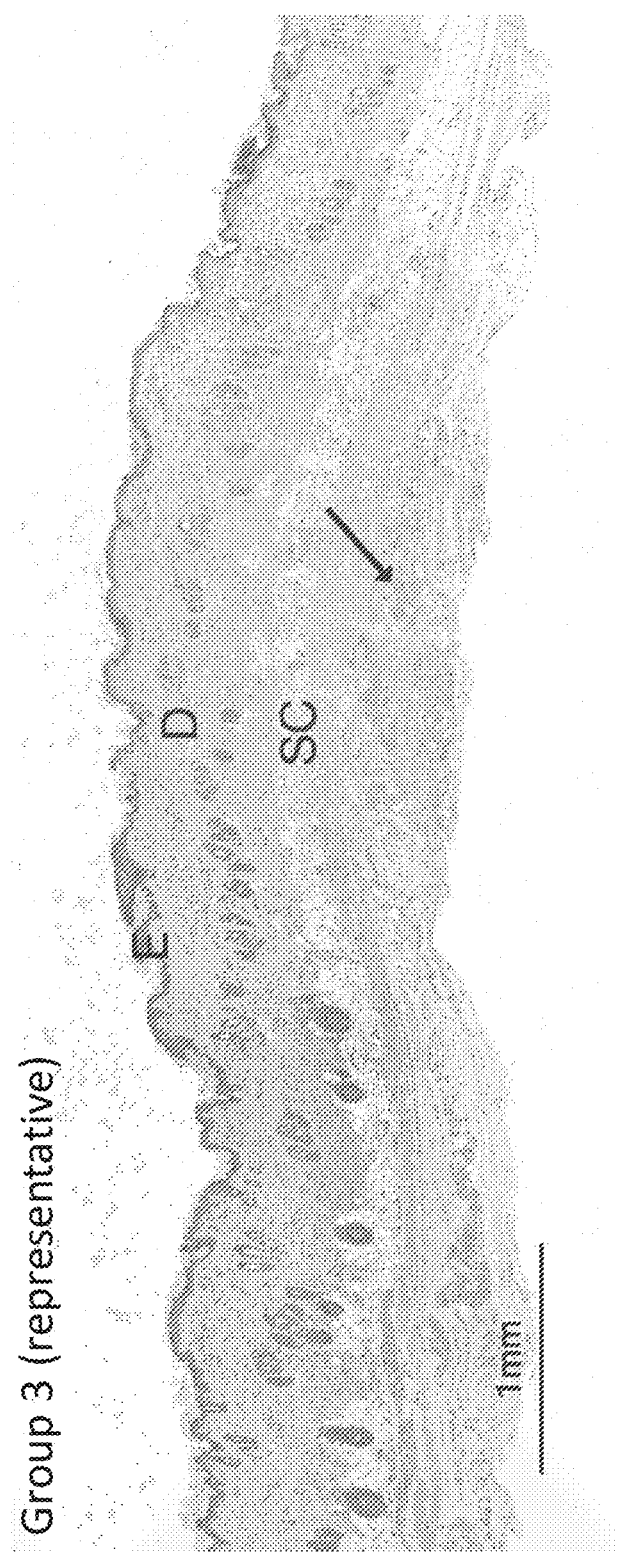

FIG. 15 is a representative histogram image of skin from rat in Group 3 (ABI-009, 1.7 mg/kg). Minimal mixed inflammatory cell infiltration (black arrow) is visible in the subcutaneous tissues (SC). The epidermis (E) and dermis (D) are indicated.

Figure 16:
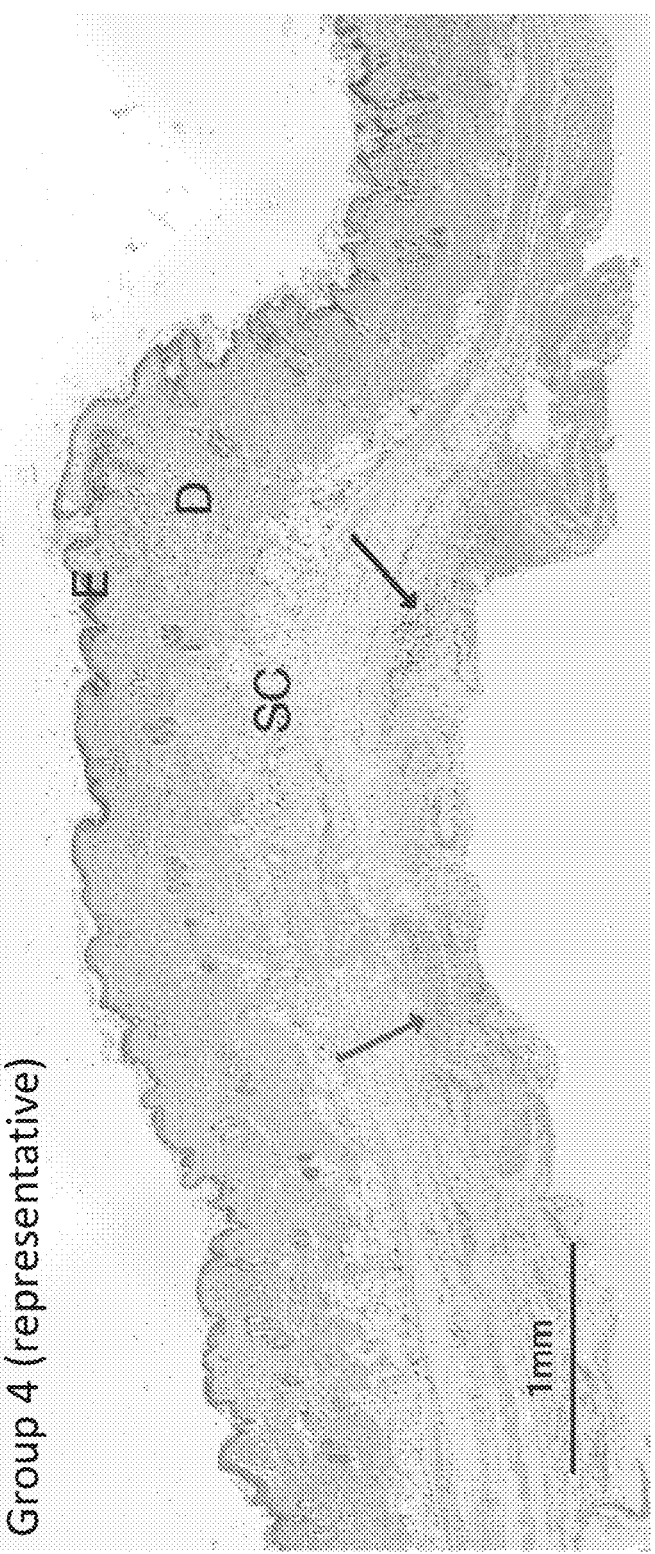

FIG. 16 is a representative histogram image of skin from rat in Group 4 (ABI-009, 5 mg/kg). Scattered mixed inflammatory cell infiltration (black arrow) and a site of minimal necrosis (blue arrow) are present in the subcutis (SC). The epidermis (E) and dermis (D) are unremarkable.

Figure 17:
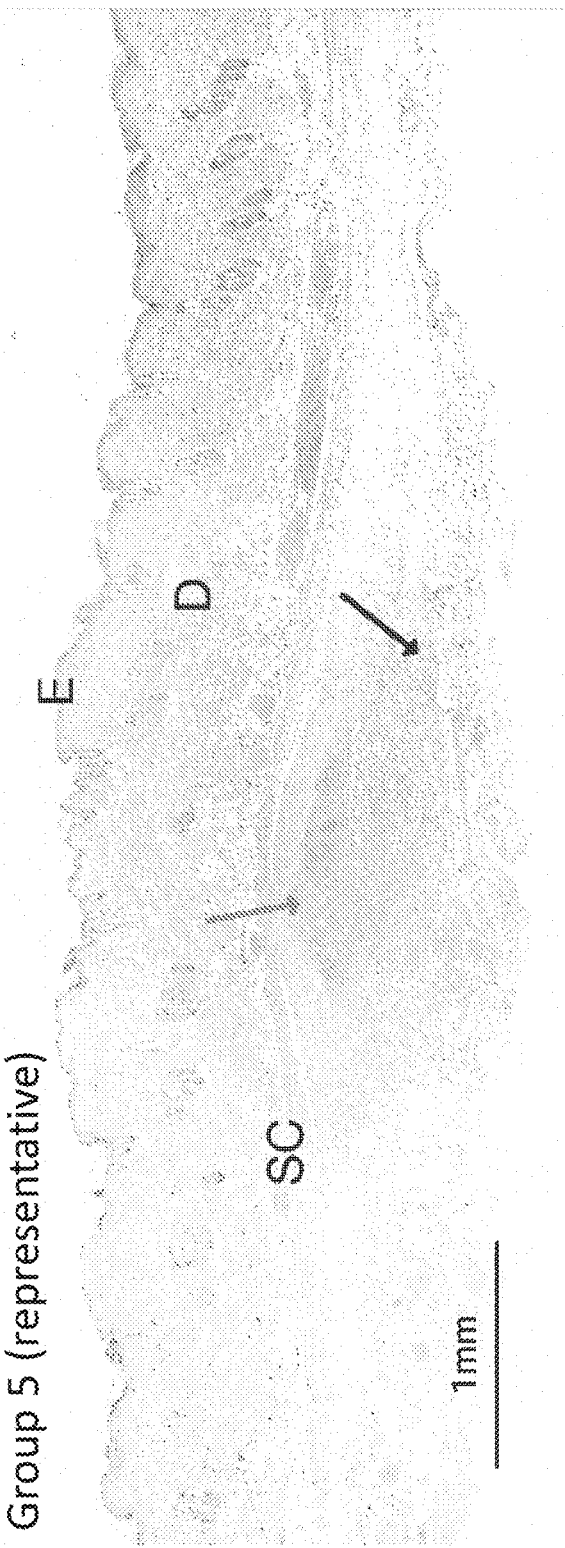

FIG. 17 is a representative histogram image of skin from rat in Group 4 (ABI-009, 10 mg/kg). Subcutaneous (SC) mixed inflammatory cell infiltration (black arrow) and a region of necrosis (blue arrow) are captured. The epidermis (E) and dermis (D) are unremarkable.

Figure 18:
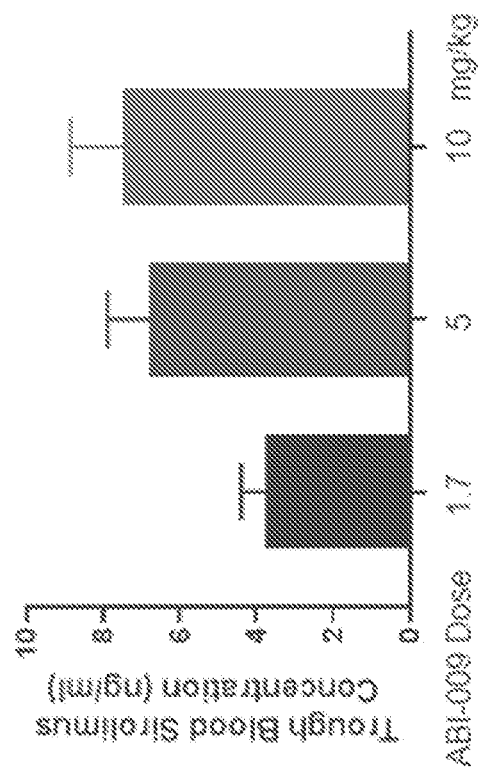

FIG. 18 shows the mean through sirolimus blood levels in rats administered with ABI-009 at 1.7 mg/kg, 5 mg/kg or 10 mg/kg.

DETAILED DESCRIPTION OF THE INVENTION

The present application provides methods for treating a CNS disorder (e.g., glioblastoma, epilepsy, cortical dysplasia) in an individual, comprising systemically (e.g., intravenously or subcutaneously) administering to the individual an effective amount of a composition comprising an mTOR inhibitor (e.g., a limus drug, e.g., sirolimus or a derivative thereof) and an albumin. One important reason for the difficulty of treating CNS diseases is that many therapeutic agents cannot pass through the blood-brain barrier (BBB). This application is based upon applicants' surprising finding that systemically administered nanoparticles comprising an mTOR inhibitor (e.g., a limus drug, e.g., sirolimus) and an albumin not only penetrate blood-brain barrier, but also stay in the CNS for a sustained period of time (such as at least 120 hours). In some aspects, the present application provides methods for treating epilepsy. In some aspects, the present application provides methods for treating cortical dysplasia (e.g., focal cortical dysplasia). In some aspects, the present application provides methods for treating a brain tumor, such as glioblastoma.

The present application also provides methods for treating a CNS disorder (e.g., glioblastoma, epilepsy, cortical dysplasia) in an individual, comprising a) systemically (e.g., intravenously or subcutaneously) administering to the individual an effective amount of a composition comprising an mTOR inhibitor (e.g., a limus drug, e.g., sirolimus or a derivative thereof) and an albumin; b) administering to the individual a second agent (e.g., an anti-VEGF antibody, a proteasome inhibitor such as marizomib, an alkylating agent such as temozolomide or lomustine, an anti-epilepsy drug).

Definitions

Unless specifically indicated otherwise, all technical and scientific terms used herein have the same meaning as commonly understood by those of ordinary skill in the art to which this application belongs. In addition, any method or material similar or equivalent to a method or material described herein can be used in the practice of the present application. For purposes of the present application, the following terms are defined.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

The term "about X-Y" used herein has the same meaning as "about X to about Y." The expression "about X, Y and/or Z" used herein has the same meaning as "about X, about Y, and/or about Z."

As used herein, reference to "not" a value or parameter generally means and describes "other than" a value or parameter. For example, the method is not used to treat cancer of type X means the method is used to treat cancer of types other than X.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

As used herein "nab" ® stands for nanoparticle albumin-bound, and "nab-sirolimus" is an albumin stabilized nanoparticle formulation of sirolimus. Nab-sirolimus is also known as nab-rapamycin, which has been previously described. See, for example, WO2008109163A1, WO2014151853, WO2008137148A2, and WO2012149451A1, each of which is incorporated herein by reference in their entirety.

Reference to "rapamycin" herein applies to rapamycin or its derivatives and accordingly the application contemplates and includes all these embodiments. In this application, "rapamycin" and "sirolimus" are used interchangeably. Rapamycin is sometimes referred to elsewhere as rapamycin, rapammune, or rapamune. Reference to "rapamycin" is to simplify the description and is exemplary. Derivatives of rapamycin include, but are not limited to, compounds that are structurally similar to rapamycin, or are in the same general chemical class as rapamycin, analogs of rapamycin, or pharmaceutically acceptable salts of rapamycin or its derivatives or analogs. In some embodiments, an mTOR inhibitor (e.g., rapamycin or a derivative thereof, e.g., rapamycin) increases basal AKT activity, increases AKT phosphorylation, increases PI3-kinase activity, increases the length of activation of AKT (e.g., activation induced by exogenous IGF-1), inhibits serine phosphorylation of IRS-1, inhibits IRS-1 degradation, inhibits or alters CXCR4 subcellular localization, inhibits VEGF secretion, decreases expression of cyclin D2, decreases expression of survivin, inhibits IL-6-induced multiple myeloma cell growth, inhibits pulmonary hypertension cell proliferation, increases apoptosis, increases cell cycle arrest, increases cleavage of poly(ADPribose) polymerase, increases cleavage of caspase-8/caspase-9, alters or inhibits signaling in the phosphatidylinositol 3-kinase/AKT/mTOR and/or cyclin D1/retinoblastoma pathways, inhibits angiogenesis, and/or inhibits osteoclast formation. In some embodiments, the derivative of rapamycin retains one or more similar biological, pharmacological, chemical and/or physical properties (including, for example, functionality) as rapamycin. An exemplary rapamycin derivative includes benzoyl rapamycin, such as that disclosed in paragraph [0022] of WO 2006/089207, which is hereby incorporated by reference in its entirety. Other exemplary rapamycin derivatives include WY-090217, AY-22989, NSC-226080, SiiA-9268A, oxaazacyclohentriacontine, temrapamycin (CCI 779 (Wyeth)), everolimus (RAD 001 (Novartis)), pimecrolimus (ASM981), SDZ-RAD, SAR943, ABT-578, AP23573, and Biolimus A9.

As used herein, "treatment" or "treating" is an approach for obtaining beneficial or desired results including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, reducing recurrence rate of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. In some embodiments, the treatment reduces the severity of one or more symptoms associated with cancer by at least about any of 10%, 20%, 30%, 40%, 50%, 60%, 70%, 80%, 90%, 95% or 100% compared to the corresponding symptom in the same subject prior to treatment or compared to the corresponding symptom in other subjects not receiving the treatment. Also encompassed by "treatment" is a reduction of pathological consequence of cancer. The methods of the application contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "effective amount" used herein refers to an amount of a compound or composition sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation in cancer. In some embodiments, an effective amount is an amount sufficient to delay development of cancer. In some embodiments, an effective amount is an amount sufficient to prevent or delay recurrence. In some embodiments, an effective amount is an amount sufficient to reduce recurrence rate in the individual. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; (vii) reduce recurrence rate of tumor, and/or (viii) relieve to some extent one or more of the symptoms associated with the cancer.

As is understood in the art, an "effective amount" may be in one or more doses, i.e., a single dose or multiple doses may be required to achieve the desired treatment endpoint. An effective amount may be considered in the context of administering one or more therapeutic agents, and a nanoparticle composition (e.g., a composition including sirolimus and an albumin) may be considered to be given in an effective amount if, in conjunction with one or more other agents, a desirable or beneficial result may be or is achieved. The components (e.g., the first and second therapies) in a combination therapy of the application may be administered sequentially, simultaneously, or concurrently using the same or different routes of administration for each component. Thus, an effective amount of a combination therapy includes an amount of the first therapy and an amount of the second therapy that when administered sequentially, simultaneously, or concurrently produces a desired outcome.

"In conjunction with" or "in combination with" refers to administration of one treatment modality in addition to another treatment modality, such as administration of a nanoparticle composition described herein in addition to administration of the other agent to the same individual under the same treatment plan. As such, "in conjunction with" or "in combination with" refers to administration of one treatment modality before, during or after delivery of the other treatment modality to the individual.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy is contained in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U. S. Food and Drug administration.

Method of Treating a CNS Disease

The present application provides a variety of methods of using nanoparticle compositions with an mTOR inhibitor (e.g., rapamycin) and a carrier protein (e.g., albumin) to treat a central nervous system (CNS) disorder. In some embodiments, the nanoparticle composition is systemically (e.g., intravenously or subcutaneously) administered into the individual. In some embodiments, the CNS disorder is epilepsy (e.g., surgically refractory epilepsy). In some embodiments, the CNS disorder is glioblastoma (e.g., recurrent glioblastoma, e.g., newly diagnosed glioblastoma). In some embodiments, the individual has undergone surgical resection of newly diagnosed glioblastoma. In some embodiments, the method further comprises a second agent, such as an alkylating agent, a proteasome inhibitor and/or an anti-VEGF antibody. In some embodiments, the method further comprises a non-invasive treatment (for example, a non-invasive treatment that interferes with cell (such as glioblastoma cancer cell division), for example by creating low-intensity, wave-like electric fields called tumor treating fields, e.g., Optune® treatment). In some embodiments, the method further comprises radiotherapy (e.g., focal radiotherapy).

In some embodiments, there is provided a method of treating a CNS disorder in an individual, comprising systemically (e.g., intravenously or subcutaneously) administering to the individual an effective amount of a composition comprising nanoparticles comprising an mTOR inhibitor and an albumin. In some embodiments, the mTOR inhibitor is a limus drug.

In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the CNS disorder comprises an mTOR-activation aberration. In some embodiments, the mTOR-activation aberration comprises a PTEN aberration. In some embodiments, the individual is a human.

In some embodiments, there is provided a method of treating a CNS disorder in an individual, comprising (a) systemically (e.g., intravenously or subcutaneously) administering to the individual an effective amount of a composition comprising nanoparticles comprising an mTOR inhibitor and an albumin; and (b) administering to the individual an effective amount of an anti-VEGF antibody (e.g., bevacizumab). In some embodiments, the amount of the anti-VEGF is from about 1 mg/kg to about 5 mg/kg for each administration. In some embodiments, the anti-VEGF antibody is administered once every two weeks. In some embodiments, the anti-VEGF antibody is administered at an amount of less than about 5 mg/kg each week. In some embodiments, the anti-VEGF antibody is administered within an hour of the administration of the nanoparticles. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the CNS disorder comprises an mTOR-activation aberration. In some embodiments, the mTOR-activation aberration comprises a PTEN aberration. In some embodiments, the individual is a human.

In some embodiments, there is provided a method of treating a CNS disorder in an individual, comprising (a) systemically (e.g., intravenously or subcutaneously) administering to the individual an effective amount of a composition comprising nanoparticles comprising an mTOR inhibitor and an albumin; and (b) administering to the individual an effective amount of an alkylating agent (e.g., temozolomide). In some embodiments, the amount of the alkylating agent is about 25 mg/m$^2$ to about 100 mg/m$^2$. In some embodiments, the alkylating agent is administered daily. In some embodiments, the alkylating agent is administered daily for at least about three weeks. In some embodiments, the amount of the alkylating agent is about 125 mg/m$^2$ to about 175 mg/m$^2$ for each administration. In some embodiments, the alkylating agent is administered about 4-6 times every four weeks. In some embodiments, the alkylating agent is administered daily for five consecutive days every four weeks. In some embodiments, the alkylating agent is administered for at least six cycles, wherein each cycle consists of twenty-eight days. In some embodiments, the alkylating agent is administered orally. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the CNS disorder comprises an mTOR-activation aberration. In some embodiments, the mTOR-activation aberration comprises a PTEN aberration. In some embodiments, the individual is a human.

In some embodiments, there is provided a method of treating a CNS disorder in an individual, comprising (a) systemically (e.g., intravenously or subcutaneously) administering to the individual an effective amount of a composition comprising nanoparticles comprising an mTOR inhibitor and an albumin; (b) administering to the individual an effective amount of an alkylating agent (e.g., temozolomide); and (c) administering to the individual an effective amount of radiotherapy. In some embodiments, the radiotherapy is focal radiotherapy. In some embodiments, the amount of the alkylating agent is about 25 mg/m$^2$ to about 100 mg/m$^2$. In some embodiments, the alkylating agent is administered daily. In some embodiments, the alkylating agent is administered daily for at least about three weeks. In some embodiments, the amount of the alkylating agent is about 125 mg/m$^2$ to about 175 mg/m$^2$ for each administration. In some embodiments, the alkylating agent is administered about 4-6 times every four weeks. In some embodiments, the alkylating agent is administered daily for five consecutive days every four weeks. In some embodiments, the alkylating agent is administered for at least six cycles, wherein each cycle consists of twenty-eight days. In some embodiments, the alkylating agent is administered orally. In some embodiments, the focal radiotherapy is administered daily. In some embodiments, about 40-80 Gy focal radiotherapy is administered each week. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1.

In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the CNS disorder comprises an mTOR-activation aberration. In some embodiments, the mTOR-activation aberration comprises a PTEN aberration. In some embodiments, the individual is a human.

In some embodiments, there is provided a method of treating a CNS disorder in an individual, comprising (a) systemically (e.g., intravenously or subcutaneously) administering to the individual an effective amount of a composition comprising nanoparticles comprising an mTOR inhibitor and an albumin; and (b) administering to the individual an effective amount of an alkylating agent, wherein the alkylating agent is a nitrosourea compound (e.g., lomustine). In some embodiments, the amount of the nitrosourea compound is about 80 mg/m$^2$ to about 100 mg/m$^2$ for each administration. In some embodiments, the nitrosourea compound is administered orally. In some embodiments, the nitrosourea compound is administered once every six weeks. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the CNS disorder comprises an mTOR-activation aberration. In some embodiments, the mTOR-activation aberration comprises a PTEN aberration. In some embodiments, the individual is a human.

In some embodiments, there is provided a method of treating a CNS disorder in an individual, comprising (a) systemically (e.g., intravenously or subcutaneously) administering to the individual an effective amount of a composition comprising nanoparticles comprising an mTOR inhibitor and an albumin; (b) administering to the individual an effective amount of a proteasome inhibitor. In some embodiments, the proteasome inhibitor is brain-penetrant proteasome inhibitor. In some embodiments, the proteasome inhibitor is marizomib. In some embodiments, the amount of the proteasome inhibitor is about 0.1 mg/m$^2$ to about 5.0 mg/m$^2$ for each administration. In some embodiments, the proteasome inhibitor is administered three times every four weeks. In some embodiments, the proteasome inhibitor is administered within an hour of the administration of the nanoparticles. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the CNS disorder comprises an mTOR-activation aberration. In some embodiments, the mTOR-activation aberration comprises a PTEN aberration. In some embodiments, the individual is a human.

In some embodiments, a method is provided for delivering an effective amount of an mTOR inhibitor (such as sirolimus) to the brain of an individual, the method comprising subcutaneously administering a composition, such as a pharmaceutical composition, comprising nanoparticles comprising rapamycin and an albumin, wherein the dose of rapamycin in the nanoparticles to deliver an effective amount of rapamycin to the brain is any of about 0.1 mg/m$^2$ to about 10 mg/m$^2$ (such as about 0.1 mg/m$^2$ to about 5 mg/m$^2$, about 5 mg/m$^2$ to about 10 mg/m$^2$) and values and ranges therein. In some embodiments, the individual has a CNS disorder (such as epilepsy).

In some embodiments, a method is provided for delivering an effective amount of an mTOR inhibitor (such as sirolimus) to the brain of an individual, the method comprising intravenously (such as via an IV push within 5, 4, or 3 minutes) administering a composition, such as a pharmaceutical composition, comprising nanoparticles comprising rapamycin and an albumin, wherein the dose of rapamycin in the nanoparticles to deliver an effective amount of rapamycin to the brain is any of about 0.1 mg/m$^2$ to about 10 mg/m$^2$ (such as about 0.1 mg/m$^2$ to about 5 mg/m$^2$, about 5 mg/m$^2$ to about 10 mg/m$^2$), and values and ranges therein. In some embodiments, the individual has a CNS disorder (such as epilepsy).

The present application provides methods of treating multiple CNS disorders in an individual. In some embodiments, the CNS disorder is a tumor in the central nervous system. In some embodiments, the CNS disorder is a developmental disorder in the central nervous system. In some embodiments, the CNS disorder is a degenerative disorder in the central nervous system.

In some embodiments, the CNS disorder is a glioma. In some embodiments, the CNS disorder is a glioblastoma. In some embodiments, the CNS disorder is epilepsy. In some embodiments, the CNS disorder is cortical dysplasia (e.g., focal cortical dysplasia). In some embodiments, the CNS disorder is selected from the group consisting of tuberous sclerosis complex, brain tumor, Fragile X syndrome, Down syndrome, Rett syndrome, Alzheimer's disease, Parkinson's disease, and Huntington's disease.

A. Method of Treating Glioblastoma

In some embodiments, there is provided a method of treating glioblastoma (e.g., recurrent glioblastoma or newly diagnosed glioblastoma) in an individual, comprising systemically (e.g., intravenously or subcutaneously) administering to the individual an effective amount of a composition comprising nanoparticles comprising an mTOR inhibitor and an albumin. In some embodiments, the individual has undergone surgical resection prior to the initiation of the nanoparticle administration. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the glioblastoma comprises an mTOR-activation aberration. In some embodiments, the mTOR-activation aberration comprises a PTEN aberration. In some embodiments, the individual is a human.

In some embodiments, there is provided a method of treating glioblastoma (e.g., recurrent glioblastoma) in an individual, comprising (a) systemically (e.g., intravenously or subcutaneously) administering to the individual a composition comprising nanoparticles comprising an effective amount of an mTOR inhibitor and an albumin; and (b) administering to the individual an effective amount of an anti-VEGF antibody (e.g., bevacizumab). In some embodiments, the amount of the anti-VEGF is from about 1 mg/kg to about 5 mg/kg for each administration. In some embodiments, the anti-VEGF antibody is administered once every two weeks. In some embodiments, the anti-VEGF antibody is administered at an amount of less than about 5 mg/kg each week. In some embodiments, the anti-VEGF antibody is administered within an hour of the administration of the nanoparticles. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as about 60 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the glioblastoma comprises an mTOR-activation aberration. In some embodiments, the mTOR-activation aberration comprises a PTEN aberration. In some embodiments, the individual is a human. In some embodiments, the individual has a Grade 3 or Grade 4 Glioblastoma. In some embodiments, the individual has anaplastic oligodendroglioma (such as Grade 3 anaplastic oligodendroglioma). In some embodiments, the individual is refractory to a prior surgery and/or a prior treatment for glioblastoma (such as standard temozolomide (TMZ)/radiation therapy (RT) treatment).

In some embodiments, there is provided a method of treating glioblastoma (e.g., recurrent glioblastoma or newly diagnosed glioblastoma) in an individual, comprising (a) systemically (e.g., intravenously or subcutaneously) administering to the individual a composition comprising nanoparticles comprising an effective amount of an mTOR inhibitor and an albumin; and (b) administering to the individual an effective amount of an alkylating agent (e.g., temozolomide). In some embodiments, the individual has undergone surgical resection of newly diagnosed glioblastoma prior to the initiation of the nanoparticle administration. In some embodiments, the amount of the alkylating agent (such as temozolomide) is about 25 mg/m$^2$ to about 100 mg/m$^2$ (such as about 50 mg/m$^2$). In some embodiments, the alkylating agent is administered daily. In some embodiments, the alkylating agent is administered daily for at least about three weeks. In some embodiments, the amount of the alkylating agent is about 125 mg/m$^2$ to about 175 mg/m$^2$ for each administration. In some embodiments, the alkylating agent is administered about 4-6 times every four weeks. In some embodiments, the alkylating agent is administered daily for five consecutive days every four weeks. In some embodiments, the alkylating agent is administered for at least six cycles, wherein each cycle consists of twenty-eight days. In some embodiments, the alkylating agent is administered orally. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as about 45-60 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1.

In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the glioblastoma comprises an mTOR-activation aberration. In some embodiments, the mTOR-activation aberration comprises a PTEN aberration. In some embodiments, the individual is a human. In some embodiments, the individual has a Grade 3 or Grade 4 Glioblastoma. In some embodiments, the individual is refractory to a prior surgery and/or a prior treatment for glioblastoma (such as standard temozolomide (TMZ)/radiation therapy (RT) treatment).

In some embodiments, there is provided a method of treating glioblastoma (e.g., newly diagnosed glioblastoma) in an individual, comprising (a) systemically (e.g., intravenously or subcutaneously) administering to the individual an effective amount of a composition comprising nanoparticles comprising an mTOR inhibitor and an albumin; (b) administering to the individual an effective amount of an alkylating agent (e.g., temozolomide); and (c) administering to the individual an effective amount of radiotherapy.

In some embodiments, the radiotherapy is focal radiotherapy. In some embodiments, the individual has undergone surgical resection of newly diagnosed glioblastoma prior to the initiation of the nanoparticle administration. In some embodiments, the radiotherapy is focal radiotherapy. In some embodiments, the amount of the alkylating agent is about 25 mg/m$^2$ to about 100 mg/m$^2$. In some embodiments, the alkylating agent is administered daily. In some embodiments, the alkylating agent is administered daily for at least about three weeks. In some embodiments, the amount of the alkylating agent is about 125 mg/m$^2$ to about 175 mg/m$^2$ for each administration. In some embodiments, the alkylating agent is administered about 4-6 times every four weeks. In some embodiments, the alkylating agent is administered daily for five consecutive days every four weeks. In some embodiments, the alkylating agent is administered for at least six cycles, wherein each cycle consists of twenty-eight days. In some embodiments, the alkylating agent is administered orally. In some embodiments, the focal radiotherapy is administered daily. In some embodiments, about 40-80 Gy focal radiotherapy is administered each week. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the glioblastoma comprises an mTOR-activation aberration. In some embodiments, the mTOR-activation aberration comprises a PTEN aberration. In some embodiments, the individual is a human. In some embodiments, the individual has a Grade 3 or Grade 4 Glioblastoma. In some embodiments, the individual is refractory to a prior surgery and/or a prior treatment for glioblastoma (such as standard temozolomide (TMZ)/radiation therapy (RT) treatment).

In some embodiments, there is provided a method of treating glioblastoma (e.g., recurrent glioblastoma or newly diagnosed glioblastoma) in an individual, comprising (a) systemically (e.g., intravenously or subcutaneously) administering to the individual an effective amount of a composition comprising nanoparticles comprising an mTOR inhibitor and an albumin; and (b) administering to the individual an effective amount of an alkylating agent, wherein the alkylating agent is a nitrosourea compound (e.g., lomustine). In some embodiments, the individual has undergone surgical resection of newly diagnosed glioblastoma prior to the initiation of the nanoparticle administration. In some embodiments, the amount of the nitrosourea compound (such as lomustine) is about 80 mg/m$^2$ to about 100 mg/m$^2$ (such as about 90 mg/m$^2$) for each administration. In some embodiments, the nitrosourea compound is administered orally. In some embodiments, the nitrosourea compound is administered once every six weeks. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as about 60 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1.

In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the glioblastoma comprises an mTOR-activation aberration. In some embodiments, the mTOR-activation aberration comprises a PTEN aberration. In some embodiments, the individual is a human. In some embodiments, the individual has a Grade 3 or Grade 4 Glioblastoma. In some embodiments, the individual is refractory to a prior surgery and/or a prior treatment for glioblastoma (such as standard temozolomide (TMZ)/radiation therapy (RT) treatment, a non-invasive treatment (e.g., optune device), marizomib treatment and CAR-T cell immunotherapy).

In some embodiments, there is provided a method of treating glioblastoma (e.g., recurrent glioblastoma) in an individual, comprising (a) systemically (e.g., intravenously or subcutaneously) administering to the individual an effective amount of a composition comprising nanoparticles comprising an mTOR inhibitor and an albumin; (b) administering to the individual an effective amount of a proteasome inhibitor. In some embodiments, the proteasome inhibitor is brain-penetrant proteasome inhibitor. In some embodiments, the proteasome inhibitor is marizomib. In some embodiments, the amount of the proteasome inhibitor is about 0.1 mg/m$^2$ to about 5.0 mg/m$^2$ for each administration. In some embodiments, the proteasome inhibitor is administered three times every four weeks. In some embodiments, the proteasome inhibitor is administered within an hour of the administration of the nanoparticles. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1.

In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the glioblastoma comprises an mTOR-activation aberration. In some embodiments, the mTOR-activation aberration comprises a PTEN aberration. In some embodiments, the individual is a human.

In some embodiments, there is provided a method of treating glioblastoma (e.g., newly diagnosed glioblastoma) in an individual, comprising a first treatment, a second treatment and a third treatment, wherein: the first treatment comprises systemically (e.g., intravenously or subcutaneously) administering a composition comprising nanoparticles comprising an mTOR inhibitor and an albumin; the second treatment comprises a) systemically (e.g., intravenously or subcutaneously) administering the nanoparticle composition, b) administering an alkylating agent, and c) administering a radiotherapy; the third treatment comprises a) systemically (e.g., intravenously or subcutaneously) administering the nanoparticle composition, and b) administering the alkylating agent; wherein the second treatment initiates after the completion of the first treatment; and wherein the third treatment initiates after the completion of the second treatment. In some embodiments, the individual has undergone surgical resection of newly diagnosed glioblastoma prior to the initiation of the nanoparticle administration. In some embodiments, the first treatment initiates about 2-5 weeks following surgical resection of the newly diagnosed glioblastoma. In some embodiments, the second treatment initiates 1-2 weeks after the completion of the first treatment. In some embodiments, the third treatment initiates 3-5 weeks after the completion of the second treatment. In some embodiments, the alkylating agent is temozolomide. In some embodiments, the radiotherapy is focal radiotherapy. In some embodiments, the individual has undergone surgical resection of newly diagnosed glioblastoma prior to the initiation of the nanoparticle administration. In some embodiments, the radiotherapy is focal radiotherapy. In some embodiments, the amount of the alkylating agent is about 25 mg/m$^2$ to about 100 mg/m$^2$. In some embodiments, the alkylating agent is administered daily. In some embodiments, the alkylating agent is administered daily for at least about three weeks. In some embodiments, the amount of the alkylating agent is about 125 mg/m$^2$ to about 175 mg/m$^2$ for each administration. In some embodiments, the alkylating agent is administered about 4-6 times every four weeks. In some embodiments, the alkylating agent is administered daily for five consecutive days every four weeks. In some embodiments, the alkylating agent is administered for at least six cycles, wherein each cycle consists of twenty-eight days. In some embodiments, the alkylating agent is administered orally. In some embodiments, the focal radiotherapy is administered daily. In some embodiments, about 40-80 Gy focal radiotherapy is administered each week. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the glioblastoma comprises an mTOR-activation aberration. In some embodiments, the mTOR-activation aberration comprises a PTEN aberration. In some embodiments, the individual is a human.

In some embodiments, there is provided a method of treating recurrent glioblastoma in an individual, comprising systemically (e.g., intravenously or subcutaneously) administering to the individual an effective amount of a composition comprising nanoparticles comprising an mTOR inhibitor (e.g., a limus drug, e.g., sirolimus) and an albumin, wherein the mTOR inhibitor is administered twice every three weeks, and wherein the amount of the mTOR inhibitor in the nanoparticle composition is about 50 mg/m$^2$ to about 100 mg/m$^2$ (e.g., 56 mg/m$^2$, 60 mg/m$^2$, 75 mg/m$^2$, 100 mg/m$^2$). In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days. In some embodiments, the recurrent glioblastoma comprises an mTOR-activation aberration. In some embodiments, the mTOR-activation aberration comprises a PTEN aberration. In some embodiments, the individual is a human.

In some embodiments, there is provided a method of treating recurrent glioblastoma in an individual, comprising intravenously (such as via an IV push within 5, 4, or 3 minutes) administering to the individual an effective amount of a composition comprising nanoparticles comprising an mTOR inhibitor (e.g., a limus drug, e.g., sirolimus) and an albumin, wherein the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$). In some embodiments, the mTOR inhibitor is administered at a frequency of about once every three weeks to about once a week (such as about twice every three weeks). In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days. In some embodiments, the recurrent glioblastoma comprises an mTOR-activation aberration. In some embodiments, the mTOR-activation aberration comprises a PTEN aberration. In some embodiments, the individual is a human.

In some embodiments, there is provided a method of treating recurrent glioblastoma in an individual, comprising subcutaneously administering to the individual an effective amount of a composition comprising nanoparticles comprising an mTOR inhibitor (e.g., a limus drug, e.g., sirolimus) and an albumin, wherein the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$). In some embodiments, the mTOR inhibitor is administered at a frequency of about once every three weeks to about once a week (such as about twice every three weeks). In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days. In some embodiments, the recurrent glioblastoma comprises an mTOR-activation aberration. In some embodiments, the mTOR-activation aberration comprises a PTEN aberration. In some embodiments, the individual is a human.

In some embodiments, there is provided a method of treating recurrent glioblastoma in an individual, comprising (a) systemically (e.g., intravenously or subcutaneously) administering to the individual an effective amount of a composition comprising nanoparticles comprising an mTOR inhibitor (e.g., a limus drug, e.g., sirolimus) and an albumin; and (b) administering to the individual an effective amount of an anti-VEGF antibody (e.g., bevacizumab), wherein mTOR inhibitor is administered three times every four weeks, wherein the amount of the mTOR inhibitor in the nanoparticle composition is about 30 mg/m$^2$ to about 60 mg/m$^2$ (e.g., 30 mg/m$^2$, 45 mg/m$^2$, 56 mg/m$^2$), wherein the anti-VEGF antibody is administered once every two weeks, and wherein the amount of the anti-VEGF is about 5 mg/kg for each administration. In some embodiments, the anti-VEGF antibody is administered within an hour of the administration of the nanoparticles. In some embodiments, the average diameter of the nanoparticles in the composition is no greater than about 200 nm.

In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 28 days. In some embodiments, the recurrent glioblastoma comprises an mTOR-activation aberration. In some embodiments, the mTOR-activation aberration comprises a PTEN aberration. In some embodiments, the individual is a human.

In some embodiments, there is provided a method of treating a recurrent glioblastoma in an individual, comprising (a) systemically (e.g., intravenously or subcutaneously) administering to the individual an effective amount of a composition comprising nanoparticles comprising an mTOR inhibitor (e.g., a limus drug, e.g., sirolimus) and an albumin; (b) administering to the individual an effective amount of marizomib, wherein the mTOR inhibitor and marizomib are administered three times every four weeks, wherein the amount of the mTOR inhibitor in the nanoparticle composition is about 30 mg/m$^2$ to about 60 mg/m$^2$ (e.g., 30 mg/m$^2$, 45 mg/m$^2$, 56 mg/m$^2$), and wherein the amount of the proteasome inhibitor is about 0.8 mg/m$^2$ for each administration. In some embodiments, the proteasome inhibitor is administered within an hour of the administration of the nanoparticles. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 28 days. In some embodiments, the recurrent glioblastoma comprises an mTOR-activation aberration. In some embodiments, the mTOR-activation aberration comprises a PTEN aberration. In some embodiments, the individual is a human.

In some embodiments, there is provided a method of treating a recurrent glioblastoma in an individual, comprising (a) systemically (e.g., intravenously or subcutaneously) administering to the individual an effective amount of a composition comprising nanoparticles comprising an mTOR inhibitor (e.g., a limus drug, e.g., a sirolimus) and an albumin; and (b) administering to the individual an effective amount of temozolomide, wherein the mTOR inhibitor is administered three times every four weeks, wherein the amount of the mTOR inhibitor in the nanoparticle composition is about 30 mg/m$^2$ to about 60 mg/m$^2$ (e.g., 30 mg/m$^2$, 45 mg/m$^2$, 56 mg/m$^2$), and wherein temozolomide is administered daily at a dose of about 50 mg/m$^2$ for each administration. In some embodiments, temozolomide is administered for at least about four weeks. In some embodiments, temozolomide is administered for at least six cycles, wherein each cycle consists of twenty-eight days. In some embodiments, temozolomide is administered orally. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 28 days. In some embodiments, the recurrent glioblastoma comprises an mTOR-activation aberration. In some embodiments, the mTOR-activation aberration comprises a PTEN aberration. In some embodiments, the individual is a human.

In some embodiments, there is provided a method of treating a recurrent glioblastoma in an individual, comprising (a) systemically (e.g., intravenously or subcutaneously) administering to the individual an effective amount of a composition comprising nanoparticles comprising an mTOR inhibitor (e.g., a limus drug, e.g., sirolimus) and an albumin; and (b) administering to the individual an effective amount of lomustine, wherein mTOR inhibitor is administered two times every three weeks, wherein the amount of the mTOR inhibitor in the nanoparticle composition is about 30 mg/m$^2$ to about 60 mg/m$^2$ (e.g., 30 mg/m$^2$, 45 mg/m$^2$, 56 mg/m$^2$), wherein lomustine is administered once every six weeks, and wherein the amount of lomustine is about 90 mg/m$^2$ for each administration. In some embodiments, the lomustine is administered orally. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days. In some embodiments, the recurrent glioblastoma comprises an mTOR-activation aberration. In some embodiments, the mTOR-activation aberration comprises a PTEN aberration. In some embodiments, the individual is a human.

In some embodiments, there is provided a method of treating newly diagnosed glioblastoma in an individual, comprising systemically (e.g., intravenously or subcutaneously) administering to the individual an effective amount of a composition comprising nanoparticles comprising an mTOR inhibitor (e.g., a limus drug, e.g., sirolimus) and an albumin, wherein mTOR inhibitor is administered once a week, and wherein the amount of the mTOR inhibitor in the nanoparticle composition is about 50 mg/m$^2$ to about 100 mg/m$^2$ (e.g., 56 mg/m$^2$, 75 mg/m$^2$, 100 mg/m$^2$). In some embodiments, the individual has been subjected to a resection surgery. In some embodiments, it has been at least about 3 weeks after the completion of the resection surgery when the treatment is initiated. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for one cycle of about 28 days. In some embodiments, the newly diagnosed glioblastoma comprises an mTOR-activation aberration. In some embodiments, the mTOR-activation aberration comprises a PTEN aberration. In some embodiments, the individual is a human.

In some embodiments, there is provided a method of treating a newly diagnosed glioblastoma in an individual, comprising (a) systemically (e.g., intravenously or subcutaneously) administering to the individual an effective amount of a composition comprising nanoparticles comprising an mTOR inhibitor (e.g., a limus drug, e.g., sirolimus) and an albumin; (b) administering to the individual an effective amount of a temozolomide, wherein mTOR inhibitor is administered three times every four weeks, wherein the amount of the mTOR inhibitor in the nanoparticle composition is about 30 mg/m$^2$ to about 60 mg/m$^2$ (e.g., 30 mg/m$^2$, 45 mg/m$^2$, 56 mg/m$^2$), and wherein temozolomide is administered at a dose of about 150 mg/m$^2$ for each administration. In some embodiments, temozolomide is administered daily for about 4-6 times a week. In some embodiments, temozolomide is administered daily for five consecutive days every four week. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition, and/or temozolomide are administered for about or about or at least about six cycles, wherein each cycle consists of 28 days. In some embodiments, the newly diagnosed glioblastoma comprises an mTOR-activation aberration. In some embodiments, the mTOR-activation aberration comprises a PTEN aberration. In some embodiments, the individual is a human.

In some embodiments, there is provided a method of treating a newly diagnosed glioblastoma in an individual, comprising (a) systemically (e.g., intravenously or subcutaneously) administering to the individual an effective amount of a composition comprising nanoparticles comprising an mTOR inhibitor (e.g., a limus drug, e.g., sirolimus) and an albumin; and (b) administering to the individual an effective amount of a temozolomide, and (c) administering to the individual an effective amount of radiotherapy, wherein mTOR inhibitor is administered twice every three weeks, wherein the amount of the mTOR inhibitor in the nanoparticle composition is about 30 mg/m$^2$ to about 60 mg/m$^2$ (e.g., 30 mg/m$^2$, 45 mg/m$^2$, 56 mg/m$^2$), wherein temozolomide is administered daily at a dose of about 75 mg/m$^2$ for each administration, and wherein about 60 Gy radiotherapy is administered every week. In some embodiments, temolozomide is administered daily for about or at least about six weeks. In some embodiments, temozolomide is administered orally. In some embodiments, the radiotherapy is focal radiotherapy. In some embodiments, the radiotherapy is administered daily for about five days a week. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition, temozolomide, and/or radiotherapy are administered for about or about or at least about two cycles, wherein each cycle consists of 21 days. In some embodiments, the newly diagnosed glioblastoma comprises an mTOR-activation aberration. In some embodiments, the mTOR-activation aberration comprises a PTEN aberration. In some embodiments, the individual is a human.

B. Method of Treating Epilepsy

In some embodiments, there is provided a method of treating epilepsy (e.g., surgical-refractory epilepsy) in an individual, comprising systemically (e.g., intravenously or subcutaneously) administering to the individual an effective amount of a composition comprising nanoparticles comprising an mTOR inhibitor and an albumin. In some embodiments, the individual has undergone an epilepsy surgery. In some embodiments, the individual has at least 5, 6, 7, or 8 seizures in 30 days post epilepsy surgery and/or does not have a week of seizure freedom following epilepsy surgery. In some embodiments, the individual is no more than about 26 years old. In some embodiments, the individual is about 3 years or old. In some embodiments, the individual is about 0-26, 1-26, 2-26, or 3-26 years old. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the individual has an mTOR-activation aberration. In some embodiments, the mTOR-activation aberration comprises a PTEN aberration. In some embodiments, the individual is a human.

In some embodiments, there is provided a method of treating epilepsy (e.g., surgical-refractory epilepsy) in an individual, comprising (a) systemically (e.g., intravenously or subcutaneously) administering to the individual an effective amount of a composition comprising nanoparticles comprising an mTOR inhibitor and an albumin; and (b) administering a second agent or non-invasive treatment (for example, a non-invasive treatment that interferes with cell (such as glioblastoma cancer cell division), for example by creating low-intensity, wave-like electric fields called tumor treating fields, e.g., Optune® treatment). In some embodiments, the second agent is an anti-epilepsy drug. In some embodiments, the anti-epilepsy drug is a standard therapy for epilepsy. In some embodiments, the dosage of the anti-epilepsy drug is not significantly different from the standard or recommended dosage on a label. In some embodiments, the individual has undergone an epilepsy surgery. In some embodiments, the individual has at least 5, 6, 7, or 8 seizures in 30 days post epilepsy surgery and/or does not have a week of seizure freedom following epilepsy surgery. In some embodiments, the individual is no more than 26 years old. In some embodiments, the individual is no less than 3 years old. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the individual has an mTOR-activation aberration. In some embodiments, the mTOR-activation aberration comprises a PTEN aberration. In some embodiments, the individual is a human.

In some embodiments, there is provided a method of treating epilepsy in an individual, comprising systemically (e.g., intravenously or subcutaneously) administering to the individual an effective amount of a composition comprising nanoparticles comprising an mTOR inhibitor (e.g., a limus drug, e.g., sirolimus) and an albumin, wherein the mTOR inhibitor is administered weekly, and wherein the amount of the mTOR in the nanoparticle composition is about 1 mg/m$^2$ to about 20 mg/m$^2$ (e.g., 1 mg/m$^2$, 2.5 mg/m$^2$, 5 mg/m$^2$, 10 mg/m$^2$, 20 mg/m$^2$) for each administration. In some embodiments, the individual has been subjected to an epilepsy surgery prior to the treatment. In some embodiments, the individual has at least 5, 6, 7, or 8 seizures in 30 days post epilepsy surgery and/or does not have a week of seizure freedom following epilepsy surgery. In some embodiments, the individual is about 0-26, 1-26, 2-26, or 3-26 years old. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for about or at least about 24 weeks. In some embodiments, the individual comprises an mTOR-activation aberration. In some embodiments, the mTOR-activation aberration comprises a PTEN aberration. In some embodiments, the individual is a human.

In some embodiments, there is provided a method of treating epilepsy in an individual, comprising intravenously (such as via an IV push within 5, 4, or 3 minutes) administering to the individual an effective amount of a composition comprising nanoparticles comprising an mTOR inhibitor (e.g., a limus drug, e.g., sirolimus) and an albumin, wherein the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$). In some embodiments, the mTOR inhibitor is administered at a frequency of about once every three weeks to about once a week (such as once every three weeks). In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the individual is refractory to a prior anti-epilepsy surgery and/or at least one (such as one, two, three or more) anti-epilepsy drug (such as those described herein) or a non-invasive treatment (for example, a non-invasive treatment that interferes with cell (such as glioblastoma cancer cell division), for example by creating low-intensity, wave-like electric fields called tumor treating fields, e.g., Optune® treatment). In some embodiments, the epilepsy is associated with cortical dysplasia (such as type 2A and/or type 2B cortical dysplasia). In some embodiments, the epilepsy is associated with infantile spasms (such as intractable infantile spasms). In some embodiments, the epilepsy is associated with hemiparesis (such as left-sided congenital hemiparesis). In some embodiments, the individual is a male. In some embodiments, the individual is a human. In some embodiments, the individual is no more than 26 years old (such as no more than 26, 24, 22, 20, or 18 years old).

In some embodiments, there is provided a method of treating epilepsy in an individual, comprising subcutaneously administering to the individual an effective amount of a composition comprising nanoparticles comprising an mTOR inhibitor (e.g., a limus drug, e.g., sirolimus) and an albumin, wherein the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$). In some embodiments, the mTOR inhibitor is administered at a frequency of about once every three weeks to about once a week (such as once every three weeks). In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the individual is refractory to a prior anti-epilepsy surgery and/or at least one (such as one, two, three or more) anti-epilepsy drug (such as those described herein) or a non-invasive treatment (for example, a non-invasive treatment that interferes with cell (such as glioblastoma cancer cell division), for example by creating low-intensity, wave-like electric fields called tumor treating fields, e.g., Optune® treatment). In some embodiments, the epilepsy is associated with cortical dysplasia (such as type 2A and/or type 2B cortical dysplasia). In some embodiments, the epilepsy is associated with infantile spasms (such as intractable infantile spasms). In some embodiments, the epilepsy is associated with hemiparesis (such as left-sided congenital hemiparesis). In some embodiments, the individual is a male. In some embodiments, the individual is a human. In some embodiments, the individual is no more than 26 years old (such as no more than 26, 24, 22, 20, or 18 years old).

In some embodiments, there is provided a method of treating epilepsy in an individual, comprising (a) systemically (e.g., intravenously or subcutaneously) administering to the individual an effective amount of a composition comprising nanoparticles comprising an mTOR inhibitor (e.g., a limus drug, e.g., sirolimus) and an albumin; and (b) administering a second agent, wherein the mTOR inhibitor is administered weekly, wherein the amount of the mTOR in the nanoparticle composition is about 1 mg/m$^2$ to about 20 mg/m$^2$ (e.g., 1 mg/m$^2$, 2.5 mg/m$^2$, 5 mg/m$^2$, 10 mg/m$^2$, 20 mg/m$^2$) for each administration, and wherein the second agent is an anti-epilepsy drug. In some embodiments, the individual has been subjected to an epilepsy surgery prior to the treatment. In some embodiments, the individual has at least 5, 6, 7, or 8 seizures in 30 days post epilepsy surgery and/or does not have a week of seizure freedom following epilepsy surgery. In some embodiments, the individual is about 0-26, 1-26, 2-26, or 3-26 years old. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for about or at least about 24 weeks. In some embodiments, the individual comprises an mTOR-activation aberration. In some embodiments, the mTOR-activation aberration comprises a PTEN aberration. In some embodiments, the individual is a human.

C. Method of Treating Cortical Dysplasia

In some embodiments, there is provided a method of treating CNS dysplasia (e.g., cortical dysplasia, e.g., focal cortical dysplasia) in an individual, comprising systemically (e.g., intravenously or subcutaneously) administering to the individual an effective amount of a composition comprising nanoparticles comprising an mTOR inhibitor and an albumin. In some embodiments, the individual has undergone an epilepsy surgery. In some embodiments, the individual has at least 5, 6, 7, or 8 seizures in 30 days post epilepsy surgery and/or does not have a week of seizure freedom following epilepsy surgery. In some embodiments, the individual is no more than 26 years old. In some embodiments, the individual is no less than 3 years old. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the individual comprises an mTOR-activation aberration. In some embodiments, the mTOR-activation aberration comprises a PTEN aberration. In some embodiments, the individual is a human.

In some embodiments, there is provided a method of treating e CNS dysplasia (e.g., cortical dysplasia, e.g., focal cortical dysplasia) in an individual, comprising (a) systemically (e.g., intravenously or subcutaneously) administering to the individual an effective amount of a composition comprising nanoparticles comprising an mTOR inhibitor and an albumin; and (b) administering a second agent. In some embodiments, the second agent is an anti-epilepsy drug. In some embodiments, the anti-epilepsy drug is a standard therapy for epilepsy. In some embodiments, the dosage of the anti-epilepsy drug is not significantly different from the standard or recommended dosage on a label. In some embodiments, the individual has undergone an epilepsy surgery. In some embodiments, the individual has at least 5, 6, 7, or 8 seizures in 30 days post epilepsy surgery and/or does not have a week of seizure freedom following epilepsy surgery. In some embodiments, the individual is no more than 26 years old. In some embodiments, the individual is no less than 3 years old. In some embodiments, the mTOR inhibitor is a limus drug. In some embodiments, the mTOR inhibitor is rapamycin. In some embodiments, the amount of the mTOR inhibitor in the nanoparticle composition is no more than about 100 mg/m$^2$ (such as no more than about 100, 56, 30, 10, or 5 mg/m$^2$). In some embodiments, the nanoparticle composition is administered once every week, twice every three weeks, or three times every four weeks. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for at least about one to six cycles, wherein each cycle consists of 21 days or 28 days. In some embodiments, the individual comprises an mTOR-activation aberration. In some embodiments, the mTOR-activation aberration comprises a PTEN aberration. In some embodiments, the individual is a human.

In some embodiments, there is provided a method of treating cortical dysplasia (e.g., focal cortical dysplasia) in an individual, comprising systemically (e.g., intravenously or subcutaneously) administering to the individual an effective amount of a composition comprising nanoparticles comprising an mTOR inhibitor (e.g., a limus drug, e.g., sirolimus) and an albumin, wherein the mTOR inhibitor is administered weekly, and wherein the amount of the mTOR in the nanoparticle composition is about 1 mg/m$^2$ to about 20 mg/m$^2$ (e.g., 1 mg/m$^2$, 2.5 mg/m$^2$, 5 mg/m$^2$, 10 mg/m$^2$, 20 mg/m$^2$) for each administration. In some embodiments, the individual has been subjected to an epilepsy surgery prior to the treatment. In some embodiments, the individual has at least 5, 6, 7, or 8 seizures in 30 days post epilepsy surgery and/or does not have a week of seizure freedom following epilepsy surgery. In some embodiments, the individual is about 0-26, 1-26, 2-26, or 3-26 years old. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for about or at least about 24 weeks. In some embodiments, the individual comprises an mTOR-activation aberration. In some embodiments, the mTOR-activation aberration comprises a PTEN aberration. In some embodiments, the individual is a human.

In some embodiments, there is provided a method of treating cortical dysplasia in an individual, comprising intravenously (such as via an IV push within 5, 4, or 3 minutes) administering to the individual an effective amount of a composition comprising nanoparticles comprising an mTOR inhibitor (e.g., a limus drug, e.g., sirolimus) and an albumin, wherein the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$). In some embodiments, the mTOR inhibitor is administered at a frequency of about once every three weeks to about once a week (such as once every three weeks). In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the individual is refractory to a prior anti-epilepsy surgery and/or at least one (such as one, two, three or more) anti-epilepsy drug (such as those described herein) or a non-invasive treatment (for example, a non-invasive treatment that interferes with cell (such as glioblastoma cancer cell division), for example by creating low-intensity, wave-like electric fields called tumor treating fields, e.g., Optune® treatment). In some embodiments, the cortical dysplasia is a type 2A or type 2B. In some embodiments, the individual is a male. In some embodiments, the individual is a human. In some embodiments, the individual is no more than 26 years old (such as no more than 26, 24, 22, 20, or 18 years old).

In some embodiments, there is provided a method of treating cortical dysplasia in an individual, comprising subcutaneously administering to the individual an effective amount of a composition comprising nanoparticles comprising an mTOR inhibitor (e.g., a limus drug, e.g., sirolimus) and an albumin, wherein the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$). In some embodiments, the mTOR inhibitor is administered at a frequency of about once every three weeks to about once a week (such as once every three weeks). In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the individual is refractory to a prior anti-epilepsy surgery and/or at least one (such as one, two, three or more) anti-epilepsy drug (such as those described herein) or a non-invasive treatment (for example, a non-invasive treatment that interferes with cell (such as glioblastoma cancer cell division), for example by creating low-intensity, wave-like electric fields called tumor treating fields, e.g., Optune® treatment). In some embodiments, the cortical dysplasia is a type 2A or type 2B. In some embodiments, the individual is a male. In some embodiments, the individual is a human. In some embodiments, the individual is no more than 26 years old (such as no more than 26, 24, 22, 20, or 18 years old).

In some embodiments, there is provided a method of treating cortical dysplasia (e.g., focal cortical dysplasia) in an individual, comprising (a) systemically (e.g., intravenously or subcutaneously) administering to the individual an effective amount of a composition comprising nanoparticles comprising an mTOR inhibitor (e.g., a limus drug, e.g., sirolimus) and an albumin; and (b) administering a second agent, wherein the mTOR inhibitor is administered weekly, wherein the amount of the mTOR in the nanoparticle composition is about 1 mg/m$^2$ to about 20 mg/m$^2$ (e.g., 1 mg/m$^2$, 2.5 mg/m$^2$, 5 mg/m$^2$, 10 mg/m$^2$, 20 mg/m$^2$) for each administration, and wherein the second agent is an anti-epilepsy drug. In some embodiments, the individual has been subjected to an epilepsy surgery prior to the treatment. In some embodiments, the individual has at least 5, 6, 7, or 8 seizures in 30 days post epilepsy surgery and/or does not have a week of seizure freedom following epilepsy surgery. In some embodiments, the individual is about 0-26, 1-26, 2-26, or 3-26 years old. In some embodiments, the average diameter of the nanoparticles in the composition is no greater than about 200 nm. In some embodiments, the weight ratio of the albumin to the mTOR inhibitor in the nanoparticle composition is no greater than about 9:1. In some embodiments, the nanoparticles comprise the mTOR inhibitor associated (e.g., coated) with the albumin. In some embodiments, the nanoparticle composition is administered for about or at least about 24 weeks. In some embodiments, the individual comprises an mTOR-activation aberration. In some embodiments, the mTOR-activation aberration comprises a PTEN aberration. In some embodiments, the individual is a human.

Dosing and Method of Administration

A. Nanoparticle Composition

In some embodiments, the nanoparticle composition is administered systemically. In some embodiments, the nanoparticle composition is administered parenterally. In some embodiments, the nanoparticle composition is administered intravenously, intraarterially, intraperitoneally, intravesicularly, subcutaneously, intrathecally, intrapulmonarily, intramuscularly, intratracheally, intraocularly, transdermally, orally, or by inhalation. In some embodiments, the nanoparticle composition is administered intravenously (such as by IV push within 5, 4, or 3 minutes). In some embodiments, the nanoparticle composition is administered subcutaneously.

In some embodiments, the mTOR inhibitor nanoparticle composition is administered at least about any of 1×, 2×, 3×, 4×, 5×, 6×, or 7× (i.e., daily) a week. In some embodiments, the nanoparticle composition is administered no more than once every three days, once every five days, or once every week. In some embodiments, the nanoparticle composition is administered about once every two weeks, once every three weeks, once every four weeks, twice every three weeks, or three times every four weeks. In some embodiments, the nanoparticle composition is administered once monthly, once every two months, once every three months, or once more than every three months. In some embodiments, the intervals between each administration are less than about any of 6 months, 3 months, 1 month, 15 days, 8 days, 5 days, 3 days, or 1 day. In some embodiments, there is no break in the dosing schedule. In some embodiments, the interval between each administration is no more than about a week.

In some embodiments, the mTOR inhibitor nanoparticle composition is administered intravenously (such as via an IV push within 5, 4, or 3 minutes) to an individual (such as a human) and the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$).

In some embodiments, the mTOR inhibitor nanoparticle composition is administered subcutaneously to an individual (such as a human) and the amount of the mTOR inhibitor (such as a limus drug, e.g., sirolimus) in the nanoparticle composition is no more than about 100 mg/m$^2$ (such as no more than about 100, 56, 30, 10, or 5 mg/m$^2$).

In some embodiments, the amount of an mTOR inhibitor (such as a limus drug, e.g., sirolimus) in the mTOR inhibitor nanoparticle composition is included in any of the following ranges: about 0.1 mg to about 1000 mg, about 0.1 mg to about 2.5 mg, about 0.5 mg to about 5 mg, about 5 mg to about 10 mg, about 10 mg to about 15 mg, about 15 mg to about 20 mg, about 20 mg to about 25 mg, about 20 mg to about 50 mg, about 25 mg to about 50 mg, about 50 mg to about 75 mg, about 50 mg to about 100 mg, about 75 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg, about 500 mg to about 600 mg, about 600 mg to about 700 mg, about 700 mg to about 800 mg, about 800 mg to about 900 mg, or about 900 mg to about 1000 mg, including any range between these values. In some embodiments, the amount of the mTOR inhibitor in the nanoparticle composition is about 5 mg to about 320 mg, about 10 mg to about 210 mg, or about 15 mg to about 160 mg for each administration into an individual. In some embodiments, the amount of the mTOR inhibitor in the nanoparticle composition is at least about 5 mg, 10 mg, or 15 mg for each administration into an individual. In some embodiments, the amount of the mTOR inhibitor in the nanoparticle composition is no great than about 320 mg, 210 mg, or 160 mg for each administration into an individual. In some embodiments, the individual is a human. In some embodiments, the concentration of the mTOR inhibitor (such as a limus drug, e.g., sirolimus) in the mTOR inhibitor nanoparticle composition is dilute (about 0.1 mg/ml) or concentrated (about 100 mg/ml), including for example about any of 0.1 mg/ml to about 50 mg/ml, about 0.1 mg/ml to about 20 mg/ml, about 1 mg/ml to about 10 mg/ml, about 2 mg/ml to about 8 mg/ml, about 4 mg/ml to about 6 mg/ml, or about 5 mg/ml. In some embodiments, the concentration of the mTOR inhibitor (such as a limus drug, e.g., sirolimus) in the mTOR inhibitor nanoparticle composition is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

In some embodiments of any of the above aspects, the amount of an mTOR inhibitor (such as a limus drug, e.g., sirolimus) in the mTOR inhibitor nanoparticle composition is at least about any of 0.1 mg/kg, 0.25 mg/kg, 0.75 mg/kg, 1 mg/kg, 1.5 mg/kg, 2 mg/kg, 2.25 mg/kg 2.5 mg/kg, 2.75 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In some embodiments, the amount of the mTOR inhibitor in the nanoparticle composition is about 0.1 mg/kg to about 5 mg/kg, about 0.2 mg/kg to about 3.5 mg/kg, or about 0.25 mg/kg to about 2.75 mg/kg for each administration into an individual. In some embodiments, the amount of the mTOR inhibitor in the nanoparticle composition is at least about 0.1 mg/kg, 0.2 mg/kg or 0.25 mg/kg for each administration into an individual. In some embodiments, the amount of the mTOR inhibitor in the nanoparticle composition is no great than about 5 mg/kg, 4 mg/kg, 3.5 mg/kg, 3 mg/kg, or 2.75 mg/kg for each administration into an individual. In some embodiments, the individual is a human.

In some embodiments, the amount of the mTOR inhibitor in the nanoparticle composition is about 5 mg/m$^2$ to about 200 mg/m$^2$, about 7.5 mg/m$^2$ to about 150 mg/m$^2$, about 9.5 mg/m$^2$ to about 100 mg/m$^2$ for each administration into an individual. In some embodiments, the amount of the mTOR inhibitor in the nanoparticle composition is at least about 5 mg/m$^2$, 7.5 mg/m$^2$, or 9.5 mg/m$^2$ for each administration into an individual. In some embodiments, the amount of the mTOR inhibitor in the nanoparticle composition is no great than about 200 mg/m$^2$, 150 mg/m$^2$, or 100 mg/m$^2$ for each administration into an individual. In some embodiments, the individual is a human.

In some embodiments, the amount of the mTOR inhibitor in the nanoparticle composition is from about 0.1 mg/m$^2$ to about 150 mg/m$^2$ for each administration. In some embodiments, the amount of the mTOR inhibitor in the nanoparticle composition is from about 0.1 mg/m$^2$ to about 120 mg/m$^2$ for each administration. In some embodiments, the amount of the mTOR inhibitor in the nanoparticle composition is no more than about 200 mg/m$^2$, 150 mg/m$^2$, 120 mg/m$^2$, 100 mg/m$^2$, 80 mg/m$^2$, 60 mg/m$^2$, 40 mg/m$^2$, or 20 mg/m$^2$ for each administration. In some embodiments, the amount of the mTOR inhibitor in the nanoparticle composition is no more than about 15 mg/m$^2$, 12.5 mg/m$^2$, 10 mg/m$^2$, 7.5 mg/m$^2$, 5 mg/m$^2$, 2.5 mg/m$^2$, 2 mg/m$^2$, or 1 mg/m$^2$ for each administration. In some embodiments, the amount of the mTOR inhibitor in the nanoparticle composition is about 0.1-20 mg/m$^2$, 20-40 mg/m$^2$, 40-60 mg/m$^2$, 60-80 mg/m$^2$, 80-100 mg/m$^2$, or 100-120 mg/m$^2$ for each administration. In some embodiments, the method comprises administering a second agent, wherein the amount of the mTOR inhibitor in the nanoparticle composition is no more than about 100 mg/m$^2$ for each administration.

In some embodiments, the amount of the mTOR inhibitor in the nanoparticle composition is from about 25 mg/m$^2$ to about 500 mg/m$^2$, about 40 mg/m$^2$ to about 400 mg/m$^2$, about 50 mg/m$^2$ to about 300 mg/m$^2$, or about 60 mg/m$^2$ to about 225 mg/m$^2$ for every three to four weeks. In some embodiments, the amount of the mTOR inhibitor in the nanoparticle composition is from about 1 mg/m$^2$ to about 100 mg/m$^2$, about 4 mg/m$^2$ to about 80 mg/m$^2$, or about 10 mg/m$^2$ to about 20 mg/m$^2$ for every four weeks.

The dose of the nanoparticle composition may be discontinued or interrupted, with or without dose reduction, to manage adverse drug reactions.

In some embodiments, the nanoparticle composition is administered for at least one (such as at least any of 2, 3, 4, 5, 6, 7, 8, 9, 10, 11, 12 or more) cycle. In some embodiments, the nanoparticle composition is administered for at most 12 (such as at most any of 11, 10, 9, 8, 7, 6 or less) cycles. In some embodiments, a cycle consists of three weeks or four weeks. In some embodiments, the nanoparticle composition is administered for at least about one to six cycles, wherein each cycle consists of 21 days or 28 days. In some embodiments, the nanoparticle composition is administered for about or at least about six weeks, eight weeks, twelve weeks, or twenty-four weeks. In some embodiments, the nanoparticle composition is administered for about or at least about one month, two months, three months, four months, five months or six months. In some embodiments, the nanoparticle composition is administered for no greater than twelve months, fifteen months, eighteen months, one year, or two years.

In some embodiments, the mTOR inhibitor nanoparticle composition allows infusion of the mTOR inhibitor nanoparticle composition to an individual over an infusion time that is shorter than about 24 hours. For example, in some embodiments, the mTOR inhibitor nanoparticle composition (such as sirolimus/albumin nanoparticle composition) is administered over an infusion period of less than about any of 24 hours, 12 hours, 8 hours, 5 hours, 3 hours, 2 hours, 1 hour, 30 minutes, 20 minutes, or 10 minutes. In some embodiments, the mTOR inhibitor nanoparticle composition (such as sirolimus/albumin nanoparticle composition) is administered over an infusion period of about 30 minutes.

In some embodiments, the nanoparticle composition is administered about twice every three weeks and the amount of the mTOR inhibitor in the nanoparticle composition is about 100 mg/m$^2$ for each administration. In some embodiments, the nanoparticle composition is administered for about or at least about six months.

In some embodiments, the nanoparticle composition is systemically (e.g., intravenously or subcutaneously) administered about three times every four weeks or two times every three weeks, and the amount of the mTOR inhibitor in the nanoparticle composition no more than about 100 mg/m$^2$ for each administration (e.g., 0.1-20 mg/m$^2$, about 20-40 mg/m$^2$, 40-60 mg/m$^2$, 60-80 mg/m$^2$, or 80-100 mg/m$^2$). In some embodiments, the nanoparticle composition is administered for about or at least about six months or twelve months.

In some embodiments, the nanoparticle composition is administered as a single therapy for treating a CNS disorder.

The amount of the mTOR inhibitor nanoparticle composition (such as sirolimus/albumin nanoparticle composition) may vary with the particular composition, the mode of administration, and the type of CNS disorder being treated. In some embodiments, the doses are effective to result in an objective response (such as a partial response or a complete response). In some embodiments, the doses are sufficient to result in a complete response in the individual. In some embodiments, the doses are sufficient to result in a partial response in the individual. In some embodiments, the doses administered are sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the mTOR inhibitor nanoparticle composition (such as sirolimus/albumin nanoparticle composition). Responses of an individual to the treatment of the methods described herein can be determined, for example, based on RECIST levels.

In some embodiments, the amount of the mTOR inhibitor nanoparticle (such as sirolimus/albumin nanoparticle composition) composition is sufficient to prolong progress-free survival of the individual. In some embodiments, the amount of the mTOR inhibitor nanoparticle (such as sirolimus/albumin nanoparticle composition) composition is sufficient to prolong overall survival of the individual. In some embodiments, the amount of the mTOR inhibitor nanoparticle composition (such as sirolimus/albumin nanoparticle composition) is sufficient to produce clinical benefit of more than about any of 50%, 60%, 70%, or 77% among a population of individuals treated with the mTOR inhibitor nanoparticle composition.

In some embodiments, the amount of the mTOR inhibitor nanoparticle composition (such as sirolimus/albumin nanoparticle composition) is sufficient to decrease the size of a tumor (e.g., a brain tumor, e.g., a glioblastoma), decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, the amount of the mTOR inhibitor nanoparticle composition (such as sirolimus/albumin nanoparticle composition) is sufficient to ameliorate a symptom (e.g., seizure size or seizure number in a period of time) of a CNS disorder (e.g., epilepsy) to a lesser degree compared to the corresponding symptom in the same individual prior to treatment or in other individuals not receiving the treatment. In some embodiments, the amount of the mTOR inhibitor nanoparticle composition (such as sirolimus/albumin nanoparticle composition) is sufficient to ameliorate a symptom (e.g., seizure size or seizure number in a period of time) of a CNS disorder (e.g., epilepsy) by at least about any of 5%, 10%, 20%, 30%, 40%, 50%, 60%, 70%, 80%, 90%, 95% or 100% compared to the corresponding symptom in the same individual prior to treatment or in other individuals not receiving the treatment. Exemplary symptoms include but are not limited to headache; pain in the face, back, arms, or legs; an inability to concentrate; loss of feeling; memory loss; loss of muscle strength; tremors; seizures; increased reflexes, spasticity, tics; paralysis; and slurred speech.

In some embodiments, the amount of the mTOR inhibitor nanoparticle composition (such as sirolimus/albumin nanoparticle composition) is below the levels that induce a toxicological effect (i.e., an effect above a clinically acceptable level of toxicity) or are at a level where a potential side effect can be controlled or tolerated when the mTOR inhibitor nanoparticle composition is administered to the individual.

In some embodiments, the amount of the mTOR inhibitor nanoparticle composition (such as sirolimus/albumin nanoparticle composition) is close to a maximum tolerated dose (MTD) of the composition. In some embodiments, the amount of the mTOR inhibitor nanoparticle composition (such as sirolimus/albumin nanoparticle composition) is about or more than about any of 50%, 60%, 70%, 80%, 90%, 95%, or 98% of the MTD. In some embodiments, the amount of the mTOR inhibitor nanoparticle composition (such as sirolimus/albumin nanoparticle composition) is less than about any of 50%, 60%, 70%, 80%, 90%, 95%, or 98% of the MTD.

B. Second Agent

The present application in some embodiments comprises administration of a second agent. In some embodiments, the second agent is administered systemically. In some embodiments, the second agent is administered parenterally. In some embodiments, the second agent is administered topically (i.e., locally). In some embodiments, the second agent is administered intravenously, intraarterially, intraperitoneally, intravesicularly, subcutaneously, intrathecally, intrapulmonarily, intramuscularly, intratracheally, intraocularly, transdermally, orally, or by inhalation.

In some embodiments, the nanoparticle composition and the second agent is administered concurrently into the individual. In some embodiments, the nanoparticle composition and the second agent is administered sequentially into the individual. In some embodiments, the nanoparticle composition and the second agent is administered simultaneously into the individual.

In some embodiments, the second agent is administered prior to the administration of the nanoparticle composition. In some embodiments, the nanoparticle composition is administered within one hour, thirty minutes, fifteen minutes, or ten minutes after the completion of the nanoparticle composition administration.

In some embodiments, the second agent is administered after the completion of the nanoparticle composition administration. In some embodiments, the second agent is administered within one hour, thirty minutes, fifteen minutes, or ten minutes after the completion of the nanoparticle composition administration.

In some embodiments, the second agent is administered the same day as the administration of the nanoparticle composition for at least once. In some embodiments, the second agent is administered the same day as the administration of the nanoparticle composition for at least once, twice, three times or four times in a cycle of three weeks or four weeks.

In some embodiments, the second agent is administered at least about any of 1×, 2×, 3×, 4×, 5×, 6×, or 7× (i.e., daily) a week. In some embodiments, the second agent is administered about once every two weeks, once every three weeks, once every four weeks, twice every three weeks, or three times every four weeks. In some embodiments, the second agent is administered once monthly, once every two months, once every three months, or less frequently than once every three months. In some embodiments, the intervals between each administration are less than about any of 6 months, 3 months, 1 month, 15 days, 8 days, 5 days, 3 days, or 1 day. In some embodiments, there is no break in the dosing schedule. In some embodiments, the interval between each administration is no more than about a week.

In some embodiments, the second agent is administered for at least one (such as at least any of 2, 3, 4, 5, 6, 7, 8, 9, 10, 11, 12 or more) cycle. In some embodiments, the second agent is administered for at most 12 (such as at most any of 11, 10, 9, 8, 7, 6 or less) cycles. In some embodiments, a cycle consists of three weeks or four weeks.

In some embodiments, the second agent described herein is administered by infusion. In some embodiments, the infusion time is shorter than about 24 hours. For example, in some embodiments, the second agent is administered over an infusion period of less than about any of 24 hours, 12 hours, 8 hours, 5 hours, 3 hours, 2 hours, 1.5 hours, 1 hour, 30 minutes, 20 minutes, or 10 minutes.

The dose of the second agent may be discontinued or interrupted, with or without dose reduction, to manage adverse drug reactions. In some embodiments, the second agent is administered according to the prescribing information of an approved brand of the second agent.

In some embodiments, the second agent is applied to the individual so as to allow reduction of the normal amount of the mTOR inhibitor (such as rapamycin) in the nanoparticle composition required to effect the same degree of treatment by at least about any of 5%, 10%, 20%, 30%, 50%, 60%, 70%, 80%, 90%, or more. In some embodiments, enough mTOR inhibitor in the nanoparticle composition is administered so as to allow reduction of the normal dose of the second agent required to effect the same degree of treatment by at least about any of 5%, 10%, 20%, 30%, 50%, 60%, 70%, 80%, 90%, or more.

In some embodiments, the combination of administration of the nanoparticle composition and the second agent produces supra-additive effect.

The amount of the mTOR inhibitor nanoparticle composition (such as sirolimus/albumin nanoparticle composition) and the dose of the second agent administered to an individual (such as a human) may vary with the particular composition, the mode of administration, and the type of CNS disorder being treated. In some embodiments, the doses are effective to result in an objective response (such as a partial response or a complete response). In some embodiments, the doses are sufficient to result in a complete response in the individual. In some embodiments, the doses are sufficient to result in a partial response in the individual. In some embodiments, the doses administered are sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the mTOR inhibitor nanoparticle composition (such as sirolimus/albumin nanoparticle composition) and the second agent. Responses of an individual to the treatment of the methods described herein can be determined, for example, based on RECIST levels.

In some embodiments, the amounts of the mTOR inhibitor nanoparticle (such as sirolimus/albumin nanoparticle composition) composition and the second agent are sufficient to prolong progress-free survival of the individual. In some embodiments, the amounts of the mTOR inhibitor nanoparticle (such as sirolimus/albumin nanoparticle composition) composition and the second agent are sufficient to prolong overall survival of the individual. In some embodiments, the amounts of the mTOR inhibitor nanoparticle composition (such as sirolimus/albumin nanoparticle composition) and the second agent are sufficient to produce clinical benefit of more than about any of 50%, 60%, 70%, or 77% among a population of individuals treated with the mTOR inhibitor nanoparticle composition and the second agent.

In some embodiments, the amounts of the mTOR inhibitor nanoparticle composition (such as sirolimus/albumin nanoparticle composition) and the second agent are sufficient to decrease the size of a tumor (e.g., a brain tumor, e.g., a glioblastoma), decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, the amounts of the mTOR inhibitor nanoparticle composition (such as sirolimus/albumin nanoparticle composition) and the second agent are sufficient to ameliorate a symptom (e.g., seizure size or seizure number in a period of time) of a CNS disorder (e.g., epilepsy) to a lesser degree compared to the corresponding symptom in the same individual prior to treatment or in other individuals not receiving the treatment. In some embodiments, the amounts of the mTOR inhibitor nanoparticle composition (such as sirolimus/albumin nanoparticle composition) and the second agent are sufficient to ameliorate a symptom (e.g., seizure size or seizure number in a period of time) of a CNS disorder (e.g., epilepsy) by at least about any of 5%, 10%, 20%, 30%, 40%, 50%, 60%, 70%, 80%, 90%, 95% or 100% compared to the corresponding symptom in the same individual prior to treatment or in other individuals not receiving the treatment. Exemplary symptoms include but are not limited to headache; pain in the face, back, arms, or legs; an inability to concentrate; loss of feeling; memory loss; loss of muscle strength; tremors; seizures; increased reflexes, spasticity, tics; paralysis; and slurred speech.

In some embodiments, the amounts of the mTOR inhibitor nanoparticle composition (such as sirolimus/albumin nanoparticle composition) and the second agent are below the levels that induce a toxicological effect (i.e., an effect above a clinically acceptable level of toxicity) or are at a level where a potential side effect can be controlled or tolerated when the mTOR inhibitor nanoparticle composition and the second agent are administered to the individual.

In some embodiments, the amount of the mTOR inhibitor nanoparticle composition (such as sirolimus/albumin nanoparticle composition) is close to a maximum tolerated dose (MTD) of the composition following the same dosing regimen when administered with the second agent. In some embodiments, the amount of the mTOR inhibitor nanoparticle composition (such as sirolimus/albumin nanoparticle composition) is more than about any of 50%, 60%, 70%, 80%, 90%, 95%, or 98% of the MTD when administered with the second agent.

1. Anti-VEGF Antibody

In some embodiments, the anti-VEGF antibody (e.g., bevacizumab) is administered at least about any of 1×, 2×, 3×, 4×, 5×, 6×, or 7× (i.e., daily) a week. In some embodiments, the anti-VEGF antibody is administered about once every two weeks, once every three weeks, once every four weeks, twice every three weeks, or three times every four weeks. In some embodiments, the anti-VEGF antibody is administered once monthly, once every two months, once every three months, or once more than every three months. In some embodiments, the intervals between each administration are less than about any of 6 months, 3 months, 1 month, 15 days, 8 days, 5 days, 3 days, or 1 day. In some embodiments, there is no break in the dosing schedule. In some embodiments, the interval between each administration is no more than about a week.

In some embodiments, the amount of the anti-VEGF is from about 0.1 mg/kg to about 20 mg/kg, about 0.5 mg/kg to about 10 mg/kg, about 1 mg/kg to about 7.5 mg/kg, or about 1 mg/kg to about 5 mg/kg for each administration. In some embodiments, the amount of the anti-VEGF is no more than about 20 mg/kg, 10 mg/kg, 7.5 mg/kg, or 5 mg/kg for each administration.

In some embodiments, the amount (e.g., the average amount if not administered weekly) of the anti-VEGF is from about 0.1 mg/kg to about 20 mg/kg, about 0.5 mg/kg to about 10 mg/kg, about 1 mg/kg to about 7.5 mg/kg, or about 1 mg/kg to about 5 mg/kg for each week. In some embodiments, the amount of the anti-VEGF is no more than about 20 mg/kg, 10 mg/kg, 7.5 mg/kg, or 5 mg/kg for each week.

In some embodiments, the amount of the anti-VEGF is from about 0.1 mg/kg to about 20 mg/kg, about 0.5 mg/kg to about 10 mg/kg, about 1 mg/kg to about 7.5 mg/kg, or about 1 mg/kg to about 5 mg/kg for every two weeks. In some embodiments, the amount of the anti-VEGF is no more than about 20 mg/kg, 10 mg/kg, 7.5 mg/kg, or 5 mg/kg for every two weeks.

In some embodiments, the anti-VEGF antibody is administered intravenously.

In some embodiments, the anti-VEGF antibody allows infusion of the anti-VEGF antibody to an individual over an infusion time that is shorter than about 24 hours. For example, in some embodiments, the anti-VEGF antibody is administered over an infusion period of no more than about any of 24 hours, 12 hours, 8 hours, 5 hours, 3 hours, 2 hours, 1.5 hours, 1 hour, 30 minutes, 20 minutes, or 10 minutes. In some embodiments, the first dose of anti-VEGF antibody is administered over a longer infusion period compared to the infusion period for a subsequent dose of anti-VEGF antibody. In some embodiments, a first dose of anti-VEGF antibody is administered over an infusion period of about 60-120 minutes. In some embodiments, a second or subsequent dose of anti-VEGF antibody is administered over an infusion period of about 30-90 minutes.

In some embodiments, the anti-VEGF antibody (e.g., bevacizumab) is intravenously administered once every two weeks, and the anti-VEGF antibody is administered at an amount of about 1 mg/kg to about 10 mg/kg every two weeks. In some embodiments, the anti-VEGF antibody is administered within one hour after the completion of the nanoparticle composition administration.

2. Proteasome Inhibitor

In some embodiments, the proteasome inhibitor (e.g., marizomib) is administered at least about any of 1×, 2×, 3×, 4×, 5×, 6×, or 7× (i.e., daily) a week. In some embodiments, the proteasome inhibitor (e.g., marizomib) is administered about once every two weeks, once every three weeks, once every four weeks, twice every three weeks, or three times every four weeks. In some embodiments, the proteasome inhibitor (e.g., marizomib) is administered once monthly, once every two months, once every three months, or once more than every three months. In some embodiments, the intervals between each administration are less than about any of 6 months, 3 months, 1 month, 15 days, 8 days, 5 days, 3 days, or 1 day. In some embodiments, there is no break in the dosing schedule. In some embodiments, the interval between each administration is no more than about a week.

In some embodiments, the amount of the proteasome inhibitor (e.g., marizomib) is from about $0.05$ mg/m$^2$ to about 5 mg/m$^2$, about 0.1 mg/m$^2$ to about 2.5 mg/m$^2$, about 0.2 mg/m$^2$ to about 1.5 mg/m$^2$, about 0.4 mg/m$^2$ to about 1.2 mg/m$^2$, or about 0.6 mg/m$^2$ to about 1.0 mg/m$^2$ for each administration. In some embodiments, the amount of the proteasome inhibitor (e.g., marizomib) is no more than about 1.5 mg/m$^2$, 1.2 mg/m$^2$, 1.0 mg/m$^2$, 0.9 mg/m$^2$, or 0.8 mg/m$^2$ for each administration. In some embodiments, the amount of the proteasome inhibitor (e.g., marizomib) is more than about 0.4 mg/m$^2$, 0.5 mg/m$^2$, 0.6 mg/m$^2$, 0.7 mg/m$^2$, or 0.75 mg/m$^2$ for each administration.

In some embodiments, the amount (e.g., the average amount if not administered weekly) of the proteasome inhibitor (e.g., marizomib) is from about $0.05$ mg/m$^2$ to about 5 mg/m$^2$, about 0.1 mg/m$^2$ to about 2.5 mg/m$^2$, about 0.2 mg/m$^2$ to about 1.5 mg/m$^2$, about 0.2 mg/m$^2$ to about 1.2 mg/m$^2$, about 0.2 mg/m$^2$ to about 1.0 mg/m$^2$, about 0.4 mg/m$^2$ to about 0.8 mg/m$^2$, or about 0.5 mg/m$^2$ to about 0.7 mg/m$^2$ for each week. In some embodiments, the amount of the proteasome inhibitor (e.g., marizomib) is no more than about 1.5 mg/m$^2$, 1.2 mg/m$^2$, 1.0 mg/m$^2$, 0.9 mg/m$^2$, 0.8 mg/m$^2$, or 0.6 mg/m$^2$ for each administration. In some embodiments, the amount of the proteasome inhibitor (e.g., marizomib) is more than about 0.3 mg/m$^2$, 0.4 mg/m$^2$, 0.5 mg/m$^2$, or 0.6 mg/m$^2$ for each week.

In some embodiments, the amount of the proteasome inhibitor (e.g., marizomib) is from $0.05$ mg/m$^2$ to about 10 mg/m$^2$, about 0.5 mg/m$^2$ to about 7.5 mg/m$^2$, about 1 mg/m$^2$ to about 5 mg/m$^2$, about 1.5 mg/m$^2$ to about 3.5 mg/m$^2$, about 2 mg/m$^2$ to about 3 mg/m$^2$, about 2.1 mg/m$^2$ to about 2.8 mg/m$^2$, or about 2.3 mg/m$^2$ to about 2.5 mg/m$^2$ for every four weeks. In some embodiments, the amount of the proteasome inhibitor (e.g., marizomib) is no more than about 10 mg/m$^2$, 7.5 mg/m$^2$, 5 mg/m$^2$, 3.5 mg/m$^2$, 3 mg/m$^2$, or 2.5 mg/m$^2$ for every four weeks. In some embodiments, the amount of the proteasome inhibitor (e.g., marizomib) is more than about 0.1 mg/m$^2$, 0.5 mg/m$^2$, 1 mg/m$^2$, 1.5 mg/m$^2$, 2 mg/m$^2$, 2.1 mg/m$^2$, or 2.3 mg/m$^2$ for every four weeks.

In some embodiments, the proteasome inhibitor (e.g., marizomib) is administered intravenously.

In some embodiments, the proteasome inhibitor (e.g., marizomib) allows infusion of the proteasome inhibitor (e.g., marizomib) to an individual over an infusion time that is shorter than about 24 hours. For example, in some embodiments, the proteasome inhibitor (e.g., marizomib) is administered over an infusion period of no more than about any of 24 hours, 12 hours, 8 hours, 5 hours, 3 hours, 2 hours, 1.5 hours, 1 hour, 30 minutes, 20 minutes, or 10 minutes.

In some embodiments, the proteasome inhibitor (e.g., marizomib) is intravenously administered three times every four weeks, and the proteasome inhibitor (e.g., marizomib) is administered at an amount of about 0.6 mg/m$^2$ to about 1.0 mg/m$^2$ for each administration. In some embodiments, the proteasome inhibitor (e.g., marizomib) is administered within one hour after the completion of the nanoparticle composition administration.

3. Alkylating Agent

In some embodiments, the alkylating agent (e.g., temozolomide) is administered at least about any of 1×, 2×, 3×, 4×, 5×, 6×, or 7× (i.e., daily) a week. In some embodiments, the alkylating agent (e.g., temozolomide) is administered about once every two weeks, once every three weeks, once every four weeks, twice every three weeks, or three times every four weeks. In some embodiments, the alkylating agent (e.g., temozolomide) is administered once monthly, once every two months, once every three months, or once more than every three months. In some embodiments, the intervals between each administration are less than about any of 6 months, 3 months, 1 month, 15 days, 8 days, 5 days, 3 days, or 1 day. In some embodiments, there is no break in the dosing schedule. In some embodiments, the interval between each administration is no more than about a week.

In some embodiments, the alkylating agent (e.g., temozolomide) is administered daily for about or at least about 3 days, 5 days, a week, two weeks, three weeks, four weeks, five weeks or six weeks. In some embodiments, the alkylating agent (e.g., temozolomide) is administered with an alternating weekly schedule (seven days on and seven days off). In some embodiments, the alkylating agent (e.g., temozolomide) is administered for at least 2 consecutive days, 3 consecutive days, 4 consecutive days or 5 consecutive days in a 21-day cycle or 28-day cycle.

In some embodiments, the amount of the alkylating agent (e.g., temozolomide) is from about 1 mg/m$^2$ to about 250 mg/m$^2$, about 10 mg/m$^2$ to about 200 mg/m$^2$, about 20 mg/m$^2$ to about 150 mg/m$^2$, about 30 mg/m$^2$ to about 100 mg/m$^2$, about 40 mg/m$^2$ to about 90 mg/m$^2$, about 45 mg/m$^2$ to about 85 mg/m$^2$ for each administration. In some embodiments, the amount of the alkylating agent (e.g., temozolomide) is from about 10 mg/m$^2$ to about 100 mg/m$^2$, about 25 mg/m$^2$ to about 75 mg/m$^2$, about 40 mg/m$^2$ to about 60 mg/m$^2$, or about 50 mg/m$^2$ for each administration. In some embodiments, the amount of the alkylating agent (e.g., temozolomide) is from about 10 mg/m$^2$ to about 150 mg/m$^2$, about 25 mg/m$^2$ to about 125 mg/m$^2$, about 50 mg/m$^2$ to about 150 mg/m$^2$, or about 75 mg/m$^2$ for each administration. In some embodiments, the amount of the alkylating agent (e.g., temozolomide) is from about 10 mg/m$^2$ to about 150 mg/m$^2$, about 50 mg/m$^2$ to about 300 mg/m$^2$, about 100 mg/m$^2$ to about 200 mg/m$^2$, about 125 mg/m$^2$ to about 175 mg/m$^2$, or about 150 mg/m$^2$ for each administration.

In some embodiments, the amount of the alkylating agent (e.g., temozolomide) is from about 1 mg/m$^2$ to about 250 mg/m$^2$, about 10 mg/m$^2$ to about 200 mg/m$^2$, about 20 mg/m$^2$ to about 150 mg/m$^2$, about 30 mg/m$^2$ to about 100 mg/m$^2$, about 40 mg/m$^2$ to about 90 mg/m$^2$, about 45 mg/m$^2$ to about 85 mg/m$^2$ for each day. In some embodiments, the amount of the alkylating agent (e.g., temozolomide) is from about 10 mg/m$^2$ to about 100 mg/m$^2$, about 25 mg/m$^2$ to about 75 mg/m$^2$, about 40 mg/m$^2$ to about 60 mg/m$^2$, or about 50 mg/m$^2$ for each day. In some embodiments, the amount of the alkylating agent (e.g., temozolomide) is from about 10 mg/m$^2$ to about 150 mg/m$^2$, about 25 mg/m$^2$ to about 125 mg/m$^2$, about 50 mg/m$^2$ to about 150 mg/m$^2$, or about 75 mg/m$^2$ for each day. In some embodiments, the amount of the alkylating agent (e.g., temozolomide) is from about 10 mg/m$^2$ to about 150 mg/m$^2$, about 50 mg/m$^2$ to about 300 mg/m$^2$, about 100 mg/m$^2$ to about 200 mg/m$^2$, about 125 mg/m$^2$ to about 175 mg/m$^2$, or about 150 mg/m$^2$ for each day.

In some embodiments, the amount of the alkylating agent (e.g., temozolomide) is from about 10 mg/m$^2$ to about 800 mg/m$^2$, about 100 mg/m$^2$ to about 600 mg/m$^2$, about 100 mg/m$^2$ to about 530 mg/m$^2$ for each week. In some embodiments, the amount of the alkylating agent (e.g., temozolomide) is from about 200 mg/m$^2$ to about 500 mg/m$^2$, about 300 mg/m$^2$ to about 400 mg/m$^2$, about 325 mg/m$^2$ to about 375 mg/m$^2$, or about 350 mg/m$^2$ for each week. In some embodiments, the amount of the alkylating agent (e.g., temozolomide) is from about 300 mg/m$^2$ to about 750 mg/m$^2$, about 400 mg/m$^2$ to about 650 mg/m$^2$, about 500 mg/m$^2$ to about 550 mg/m$^2$, or about 525 mg/m$^2$ for each week. In some embodiments, the amount of the alkylating agent (e.g., temozolomide) is from about 25 mg/m$^2$ to about 175 mg/m$^2$, about 50 mg/m$^2$ to about 150 mg/m$^2$, about 75 mg/m$^2$ to about 125 mg/m$^2$, about 100 mg/m$^2$ to about 115 mg/m$^2$, or about 105 mg/m$^2$ to about 110 mg/m$^2$ for each week.

In some embodiments, the amount of the alkylating agent (e.g., temozolomide) is from about 500 mg/m$^2$ to about 2500 mg/m$^2$, about 650 mg/m$^2$ to about 2300 mg/m$^2$, about 750 mg/m$^2$ to about 2100 mg/m$^2$ for a cycle of four weeks (i.e., 28 days). In some embodiments, the amount of the alkylating agent (e.g., temozolomide) is from about 700 mg/m$^2$ to about 2100 mg/m$^2$, about 1000 mg/m$^2$ to about 1800 mg/m$^2$, about 1200 mg/m$^2$ to about 1600 mg/m$^2$, or about 1400 mg/m$^2$ for a cycle of four weeks (i.e., 28 days). In some embodiments, the amount of the alkylating agent (e.g., temozolomide) is from about 1000 mg/m$^2$ to about 3200 mg/m$^2$, about 1500 mg/m$^2$ to about 2700 mg/m$^2$, about 1800 mg/m$^2$ to about 2400 mg/m$^2$, or about 2100 mg/m$^2$ for a cycle of four weeks (i.e., 28 days). In some embodiments, the amount of the alkylating agent (e.g., temozolomide) is from about 300 mg/m$^2$ to about 1200 mg/m$^2$, about 500 mg/m$^2$ to about 1000 mg/m$^2$, about 650 mg/m$^2$ to about 850 mg/m$^2$, about 700 mg/m$^2$ to about 800 mg/m$^2$, or about 750 mg/m$^2$ for a cycle of four weeks (i.e., 28 days).

In some embodiments, the alkylating agent (e.g., temozolomide) is administered orally.

In some embodiments, the alkylating agent (e.g., temozolomide) is orally administered daily, and the alkylating agent (e.g., temozolomide) is administered at an amount of about 25 mg/m$^2$ to about 75 mg/m$^2$ for each administration. In some embodiments, the alkylating agent (e.g., temozolomide) is orally administered daily for at least four weeks, and the alkylating agent (e.g., temozolomide) is administered at an amount of about 50 mg/m$^2$ to about 100 mg/m$^2$ for each administration. In some embodiments, the alkylating agent (e.g., temozolomide) is orally administered for at least four consecutive days in a cycle of 28 days, and the alkylating agent (e.g., temozolomide) is administered at an amount of about 100 mg/m$^2$ to about 200 mg/m$^2$ for each administration.

a) Nitrosourea Compound

In some embodiments, the alkylating agent is a nitrosourea compound. In some embodiments, the nitrosourea compound is lomustine (CCNU). In some embodiments, the nitrosourea compound (e.g., lomustine) is administered about once a week, once every two weeks, once every three weeks, once every four weeks, once every five weeks or once every six weeks. In some embodiments, the nitrosourea compound (e.g., lomustine) is administered at least about any of 1×, 2×, 3×, 4×, 5×, 6×, or 7× (i.e., daily) a week. In some embodiments, the nitrosourea compound (e.g., lomustine) is administered about twice every three weeks, or three times every four weeks. In some embodiments, the nitrosourea compound (e.g., lomustine) is administered once monthly, once every two months, once every three months, or once more than every three months. In some embodiments, the intervals between each administration are less than about any of 6 months, 3 months, 1 month, 15 days, 8 days, 5 days, 3 days, or 1 day. In some embodiments, there is no break in the dosing schedule. In some embodiments, the interval between each administration is no more than about a week.

In some embodiments, the amount of the nitrosourea compound (e.g., lomustine) is from about 30 mg/m² to about 180 mg/m², about 50 mg/m² to about 150 mg/m², about 70 mg/m² to about 120 mg/m², about 80 mg/m² to about 100 mg/m², or about 90 mg/m² for each administration. In some embodiments, the amount of the nitrosourea compound (e.g., lomustine) is no more than about 180 mg/m², 150 mg/m², 120 mg/m², 100 mg/m², or 90 mg/m² for each administration. In some embodiments, the amount of the nitrosourea compound (e.g., lomustine) is more than about 30 mg/m², 50 mg/m², 70 mg/m², 80 mg/m², or 85 mg/m² for each administration.

In some embodiments, the amount of the nitrosourea compound (e.g., lomustine) is from about 30 mg/m² to about 180 mg/m², about 50 mg/m² to about 150 mg/m², about 70 mg/m² to about 120 mg/m², about 80 mg/m² to about 100 mg/m², or about 90 mg/m² for every six weeks. In some embodiments, the amount of the nitrosourea compound (e.g., lomustine) is no more than about 180 mg/m², 150 mg/m², 120 mg/m², 110 mg/m², 100 mg/m², 95 mg/m², or 90 mg/m² for every six weeks. In some embodiments, the amount of the nitrosourea compound (e.g., lomustine) is more than about 30 mg/m², 50 mg/m², 70 mg/m², 75 mg/m², 80 mg/m², or 85 mg/m² for every six weeks.

In some embodiments, the nitrosourea compound (e.g., lomustine) is administered orally.

In some embodiments, the nitrosourea compound (e.g., lomustine) is orally administered once every six weeks, and the nitrosourea compound (e.g., lomustine) is administered at an amount of about 70 mg/m² to about 120 mg/m² for each administration. In some embodiments, the nitrosourea compound (e.g., lomustine) is administered within one hour after the completion of the nanoparticle composition administration.

C. Radiotherapy

In some embodiments, the method further comprises radiotherapy. Radiation contemplated herein includes, for example, 7-rays, X-rays (external beam), and the directed delivery of radioisotopes to cells/tissues associated with the CNS disorder. Other forms of DNA damaging factors are also contemplated such as microwaves and UV irradiation are also contemplated. Radiation may be given in a single dose or in a series of small doses in a dose-fractionated schedule.

In some embodiments, enough radiotherapy is applied to the individual so as to allow reduction of the normal amount of the mTOR inhibitor (such as rapamycin) in the nanoparticle composition and/or the dose of the second agent required to effect the same degree of treatment by at least about any of 5%, 10%, 20%, 30%, 50%, 60%, 70%, 80%, 90%, or more. In some embodiments, enough mTOR inhibitor in the nanoparticle composition and/or the second agent is administered so as to allow reduction of the normal dose of the radiotherapy required to effect the same degree of treatment by at least about any of 5%, 10%, 20%, 30%, 50%, 60%, 70%, 80%, 90%, or more. In some embodiments, the amount of the mTOR inhibitor (such as rapamycin) in the nanoparticle composition, the dose of the second agent, and the dose of the radiotherapy are all reduced as compared to the corresponding normal dose of each when not used in the triple combination.

In some embodiments, the combination of administration of the nanoparticle composition (optionally with the second agent) and the radiation therapy produces supra-additive effect.

In some embodiments, the radiotherapy is whole brain radiotherapy. In some embodiments, the radiotherapy is intensity-modulated radiation therapy (IMRT). In some embodiments, the radiotherapy is focal radiotherapy.

In some embodiments, the radiotherapy is administered at least about 1, 2, 3, 4, or 5 days a week. In some embodiments, the radiotherapy is administered for about or at least about 1, 2, 3, 4, 5, or 6 weeks. In some embodiments, the radiotherapy is administered for at most about 12, 11, 10, 9, 8, 7, or 6 weeks.

In some embodiments, a total dose of radiotherapy of about 10-120Gy, 20-100Gy, 30-90Gy, 40-80Gy, 50-70Gy, 55-65Gy or 60 Gy is administered to the individual daily for at least 1, 2, 3, 4, or 5 days a week. In some embodiments, a total dose of radiotherapy of about or at least about 10Gy, 20Gy, 30Gy, 40Gy, 50Gy, 55Gy or 60 Gy is administered to the individual daily for at least 1, 2, 3, 4, or 5 days a week. In some embodiments, a total dose of radiotherapy of at most about 120Gy, 110Gy, 100Gy, 90Gy, 80Gy, 75Gy, 70Gy, 65Gy or 60 Gy is administered to the individual daily for at least 1, 2, 3, 4, or 5 days a week.

In some embodiments, a total dose of radiotherapy administered to the individual daily has about 10-50, 15-45, 20-40, 25-35, 28-32, or 30 fractions of radiation. In some embodiments, the dose of each fraction is about 50-350cGy, 100-300cGy, 125-275cGy, 150-250cGy, 175-225cGy, 190-210cGy or about 200cGy.

In some embodiments, a total dose of radiotherapy of about 50-70Gy is administered to the individual daily for at least 5 days a week, wherein each total dose of radiotherapy has about 25-35 fractions of radiation, and the dose of each fraction is about 150-250cGy.

Dosage ranges for radioisotopes vary widely, and depends on the half-life of the isotope and the strength and type of radiation emitted.

CNS Disorder

The present application provides methods of treating a CNS disorder in an individual. In some embodiments, the CNS disorder is a tumor in the central nervous system. In some embodiments, the CNS disorder is a developmental disorder in the central nervous system. In some embodiments, the CNS disorder is a degenerative disorder in the central nervous system.

In some embodiments, the CNS disorder is a glioma. In some embodiments, the CNS disorder is a glioblastoma. In some embodiments, the CNS disorder is epilepsy. In some embodiments, the CNS disorder is cortical dysplasia (e.g., focal cortical dysplasia). In some embodiments, the CNS disorder is selected from the group consisting of tuberous sclerosis complex, brain tumor, Fragile X syndrome, Down syndrome, Rett syndrome, Alzheimer's disease, Parkinson's disease, and Huntington's disease.

A. Tumor

In some embodiments, the CNS disorder is a tumor in the central nervous system. In some embodiments, the tumor is malignant. In some embodiments, the tumor is a brain tumor. In some embodiments, the tumor is a primary brain tumor. In some embodiments, the tumor is a secondary brain tumor. In some embodiments, the tumor is a glioma.

1. Glioblastoma

In some embodiments, the CNS disorder is glioblastoma (GBM). In some embodiments, the glioblastoma is classified as classical, pro-neural, neural, or mesenchymal subtype. See Verhaak et al., *Cancer Cell*. 2010 Jan. 19; 17(1): 98.

In some embodiments, the glioblastoma comprises a tumor in brain. In some embodiments, the tumor is in cerebrum. In some embodiments, the tumor is in cerebellar. In some embodiments, the tumor is in brainstem. In some embodiments, the tumor is in diencephalon.

In some embodiments, the tumor has a size less than about 5-6 cm. In some embodiments, the tumor has a size of more than about 5-6 cm. In some embodiments, the tumor crosses the midline. In some embodiments, the tumor does not cross midline.

In some embodiments, the glioblastoma comprises a genetic alteration of the receptor tyrosine kinase/Ras/phosphoinositide 3-kinase signaling pathway. In some embodiments, the glioblastoma comprises a genetic alteration on epidermal growth factor receptor (EGFR). In some embodiments, the alteration is characterized in an overexpression of EGFR. In some embodiments, the glioblastoma comprises a genetic alteration on phosphate and tensin homologue (PTEN). In some embodiments, the glioblastoma comprises a mutation on PTEN. In some embodiments, the glioblastoma has a loss of chromosome 10q. In some embodiments, the glioblastoma comprises a mutation on isocitrate dehydrogenase 1 (IDH1). In some embodiments, the glioblastoma comprises a mutation on p53. In some embodiments, the glioblastoma has a loss of chromosome 19q.

In some embodiments, the glioblastoma comprises a primary glioma in temporal lobe. In some embodiments, the glioblastoma comprises a primary glioma in extratemporal lobe. In some embodiments, the glioblastoma comprises a primary glioma in frontal lobe. In some embodiments, the glioblastoma comprises a primary glioma in parietal lobe. In some embodiments, the glioblastoma comprises a primary glioma in occipital lobe.

In some embodiments, the glioblastoma is primary. In some embodiments, the glioblastoma is de novo. In some embodiments, the glioblastoma is secondary. In some embodiments, the glioblastoma is arising without a known precursor.

a) Recurrent Glioblastoma

In some embodiments, the glioblastoma is recurrent glioblastoma.

In some embodiments, the recurrent glioblastoma is characterized by at least 1, 2, 3, 4, or 5 measurable lesions by RANO criteria (≥10 mm in 2 perpendicular diameters).

In some embodiments, the individual has been subjected to radiation therapy prior to the treatment. In some embodiments, it has been at least 1, 2, 3, 4, 5, 6, 7, 8, 9, 10, 11, or 12 weeks after the radiation therapy when the administering of the nanoparticle composition and/or the second agent is initiated.

In some embodiments, the recurrent glioblastoma is characterized by a new lesion outside of the radiation field after the radiation therapy. In some embodiments, the recurrent glioblastoma is characterized by a relapse after the radiation therapy. In some embodiments, the recurrent glioblastoma is at least 4, 6, or 8 weeks apart from the previous occurrence of the glioblastoma. In some embodiments, the recurrent glioblastoma is characterized by has a new lesion outside of the radiation field, a relapse after the radiation therapy, or the recurrent glioblastoma occurred at least 4, 6, or 8 weeks apart from the previous occurrence of the glioblastoma and the treatment is initiated less than about 1, 2, 3, 4, 5, 6, 7, 8, 9, 10, 11, or 12 weeks after the radiation therapy.

In some embodiments, the individual has been subjected to an alkylating agent (e.g., temozolomide) prior to the treatment. In some embodiments, the individual has been subjected to both radiation therapy and an alkylating agent (e.g., temozolomide) prior to the treatment.

In some embodiments, the individual has been subjected to a surgical resection prior to the treatment. In some embodiments, it has been at least 1, 2, 3, or 4 weeks after the surgical resection when the administering of the nanoparticle composition and/or the second agent is initiated.

In some embodiments, the individual has not been subjected to an anti-angiogenic agent (e.g., anti-VEGF antibody) prior to the treatment. In some embodiments, the individual has not been subjected to an mTOR inhibitor (e.g., a limus drug, e.g., rapamycin) prior to the treatment. In some embodiments, the individual has not been subjected to either an anti-angiogenic agent or an mTOR inhibitor prior to the treatment. In some embodiments, the method for treating recurrent glioblastoma in an individual comprises a) systemically (e.g., intravenously or subcutaneously) administering to the individual an effective amount of nanoparticle composition comprising a mTOR inhibitor and an albumin, and b) administering to the individual an anti-VEGF antibody, wherein the individual has not been subjected to either an anti-angiogenic agent or an mTOR inhibitor prior to the treatment.

In some embodiments, the individual has not been subjected to a proteasome inhibitor (e.g., marizomib) prior to the treatment. In some embodiments, the individual has not been subjected to an mTOR inhibitor (e.g., a limus drug, e.g., rapamycin) prior to the treatment. In some embodiments, the individual has not been subjected to either a proteasome inhibitor or an mTOR inhibitor prior to the treatment. In some embodiments, the method for treating recurrent glioblastoma in an individual comprises a) systemically (e.g., intravenously or subcutaneously) administering to the individual an effective amount of nanoparticle composition comprising a mTOR inhibitor and an albumin, and b) administering to the individual a proteasome inhibitor, wherein the individual has not been subjected to either a proteasome inhibitor or an mTOR inhibitor prior to the treatment.

In some embodiments, the individual does not have seizures for at least about 7, 10, or 14 days prior to the treatment. In some embodiments, the individual has a Karnofsky Performance Status score of at least 50%, 55%, 60%, 65%, or 70%.

b) Newly Diagnosed Glioblastoma

In some embodiments, the glioblastoma is a newly diagnosed glioblastoma (ndGBM).

In some embodiments, the individual has been subjected to a resection surgery prior to the treatment. In some embodiments, the newly diagnosed glioblastoma is characterized by at least 1, 2, 3, 4, or 5 measurable lesions by RANO criteria (≥10 mm in 2 perpendicular diameters) after the surgery.

In some embodiments, the individual has not been subjected to an mTOR inhibitor (e.g., a limus drug, e.g., rapamycin) prior to the treatment. In some embodiments, the individual has not been subjected to a local therapy prior to the treatment. In some embodiments, the individual has not been subjected to a systemic therapy prior to the treatment. In some embodiments, the individual has not been subjected to either a local therapy or a systemic therapy prior to the treatment.

In some embodiments, the individual does not have seizures for at least about 7, 10, or 14 days prior to the treatment. In some embodiments, the individual has a Karnofsky Performance Status score of at least 50%, 55%, 60%, 65%, or 70%.

B. Epilepsy

In some embodiments, the CNS disorder is epilepsy. In some embodiments, the epilepsy is therapy resistant (i.e., intractable). In some embodiments, the individual has at least 1, 2, 3, 4, or 5 seizures every month that persist after being treated with at least two, three, or four anti-epilepsy drugs (AED) or a non-invasive treatment (for example, a non-invasive treatment that interferes with cell (such as glioblastoma cancer cell division), for example by creating low-intensity, wave-like electric fields called tumor treating fields, e.g., Optune® treatment). In some embodiments, the epilepsy is associated with a lesion on MRI.

Seizures and epilepsy are generally divided into focal and generalized according to the mode of seizure onset as well as into genetic, structural, metabolic, immune, infectious, or unknown according to the underlying cause or etiology. In some embodiments, the epilepsy has a genetic basis (e.g., idiopathic localization-related epilepsy). In some embodiments, the epilepsy is cryptogenic epilepsy. In some embodiments, the epilepsy is metabolic epilepsy. In some embodiments, the epilepsy is structural epilepsy. In some embodiments, the epilepsy is immune epilepsy. In some embodiments, the epilepsy is infectious epilepsy.

In some embodiments, the individual has a seizure onset of before the age of six months, twelve months, one year, one and a half year, two years, three years, four years, five years, six years, nine years, twelve years, fifteen years or eighteen years.

In some embodiments, the individual has a mental retardation, perinatal anoxia, a history of neonatal convulsion, and/or a history of status epilepticus.

In some embodiments, the individual has frequent seizures (e.g., at least 1×, 2×, 3×, 4×, 5×, 6×, 7×, 8×, 9×, or 10× seizure(s) a month). For another example, the individual has at least 1×, 2×, 3×, 4×, 5×, 6×, or 7× (i.e., daily) seizure(s) a week. For another example, the individual has at least 1×, 2×, or 3× seizure(s) a day.

In some embodiments, the individual has frequent initial seizures (e.g., at least 1×, 2×, 3×, 4×, 5×, 6×, 7×, 8×, 9×, or 10× seizure(s) in the first month, or first two, three, four, five, six, nine, twelve, or twenty-four months). For another example, the individual has at least 1×, 2×, 3×, 4×, 5×, 6×, or 7× (i.e., daily) seizure(s) in the first week. For another example, the individual has at least 1×, 2×, 3×, 4×, 5×, 6×, or 7× seizure(s) in the first day, or the first two, three, four, five or six days.

In some embodiments, the individual has relatively low rate of seizures at baseline. For example, in some embodiments, the individual has no more than an average of about 10, 9, 8, 7, 6, 5, 4, 3, or 2 seizures a week in the last 30 days prior to the initiation of the treatment.

In some embodiments, the individual has relatively high rate of seizures at baseline. For example, in some embodiments, the individual has at least an average of about 12, 13, 14, 15, 16, 17, 18, 19, 20, 21, 22, 23 or 24 seizures a week in the last 30 days prior to the initiation of the treatment.

In some embodiments, the individual has at least 1, 2, 3, 4, 5, 6, 7, 8, 9, 10, 11, or 12 events of abnormal electroencephalography (EEG) finding(s) during a seizure. In some embodiments, the seizure is a partial seizure (i.e., focal seizure). In some embodiments, the EEG is a focal EEG. In some embodiments, the seizure is a generalized seizure. In some embodiments, the abnormal EEG finding(s) comprises a finding in the frontal lobes. In some embodiments, the abnormal EEG finding(s) comprise a finding in the temporal lobes. In some embodiments, the abnormal EEG finding(s) comprise a finding in the parietal lobes. In some embodiments, the abnormal EEG finding(s) comprise a finding in the occipital lobes. In some embodiments, the epilepsy is characterized by a diffuse EEG pattern.

In some embodiments, the epilepsy comprises temporal lobe epilepsy. In some embodiments, the epilepsy comprises uncontrolled and/or unilateral temporal lobe epilepsy.

In some embodiments, the epilepsy comprises extratemporal lobe epilepsy.

In some embodiments, the epilepsy comprises intractable epilepsy developed before the age of 6 months, 9 months, 12 months, 18 months, one year, one and a half year, two years, three years, four years, five years, six years, twelve years, or eighteen years.

In some embodiments, the individual has been subjected to an epilepsy surgery prior to the treatment. In some embodiments, the epilepsy surgery is performed within half a year, a year, one and a half year, or two years of the epilepsy onset. In some embodiments, the epilepsy surgery is performed when the individual is less than half a year, a year, one and a half years, two years, five years, eight years, twelve years, fifteen years, or eighteen years old. In some embodiments, the surgery is a focal or lobar resection surgery. In some embodiments, the surgery is a hemispheric resection surgery. In some embodiments, the resection is a total resection (i.e., the resection of lesion visible on MRI or epileptic focus determined by intracranial EEG). In some embodiments, the resection is a subtotal resection. See Kabat et al, Pol. J. Radiol, 2012; 77(2): 35-43. In some embodiments, the individual is refractory to the surgery.

In some embodiments, the surgery comprises a temporal resection. In some embodiments, the surgery does not comprise an extratemporal resection. In some embodiments, the surgery comprises an extratemporal resection. In some embodiments, the surgery does not comprise a temporal resection. In some embodiments, the epilepsy is characterized by a period of zero seizure following the surgery. In some embodiments, the period is about 1, 2, 3, 4, 5, 6 months.

In some embodiments, the epilepsy is resistant to both surgery and at least one (such as one, two, three, or more) anti-epilepsy drugs or a non-invasive treatment (for example, a non-invasive treatment that interferes with cell (such as glioblastoma cancer cell division), for example by creating low-intensity, wave-like electric fields called tumor treating fields, e.g., Optune® treatment).

In some embodiments, the epilepsy is associated with cortical dysplasia (such as type 2A and/or type 2B cortical dysplasia).

In some embodiments, the epilepsy is associated with infantile spasms (such as intractable infantile spasms). In some embodiments, the epilepsy is associated with hemiparesis (such as left-sided congenital hemiparesis).

In some embodiments, the epilepsy is associated with a tumor. In some embodiments, the tumor is a low-grade neoplastic tumor. In some embodiments, the tumor is a glioma. In some embodiments, the tumor is gangliogliomas. In some embodiments, the tumor is dysembryoplastic neuroepithelial tumor (DNET). In some embodiments, the DNET is associated with cortical dysplasia.

In some embodiments, the epilepsy is associated with perinatal infarcts. In some embodiments, the epilepsy is associated with an infection (e.g., bacterial or viral encephalitides). In some embodiments, the epilepsy is associated with sclerosis. In some embodiments, the sclerosis is hippocampal sclerosis.

In some embodiments, the epilepsy is associated with tuberous sclerosis complex. In some embodiments, the tuberous sclerosis complex is characterized by causing focal or multifocal seizures. In some embodiments, the seizures are treatment-resistant. In some embodiments, the seizures impair neurocognitive development.

In some embodiments, the epilepsy is associated with Rasmussen's syndrome. In some embodiments, the epilepsy is associated with hypothalamic hamartoma. In some embodiments, the epilepsy is associated with hemimegaloencephaly. In some embodiments, the epilepsy is associated with Lennox-Gastaut syndrome.

In some embodiments, the individual is less than 1, 2, 3, 5, 10, 12, 15, 16, 18, or 26 years old. In some embodiments, the individual is more than about 0.5, 1, 1.5, 2, 3, 5, 10, 12, 15, 16, 18, or 26 years old. In some embodiments, the individual is about 0-26, 1-26, 2-26, 3-26, 0-18, 0-15, or 0-12 years old.

C. Cortical Dysplasia (e.g., Focal Cortical Dysplasia)

In some embodiments, the CNS disorder is cortical dysplasia (e.g., focal cortical dysplasia).

In some embodiments, the cortical dysplasia (e.g., focal cortical dysplasia) is in a mild form. In some embodiments, the cortical dysplasia (e.g., focal cortical dysplasia) is in a severe form. See Palmini et al., Neurology, 2004. 62 (6 Suppl 3): p. S2-8; and Vinters et al., Int. Rev. Neurobiol, 2002. 49: p. 63-76. In some embodiments, the cortical dysplasia (e.g., focal cortical dysplasia) is in a severe form and be extratemporal.

In some embodiments, the cortical dysplasia (e.g., focal cortical dysplasia) is in Type I, Type II, or Type III. In some embodiments, the cortical dysplasia (e.g., focal cortical dysplasia) is in Type Ia or Type Ib. In some embodiments, the cortical dysplasia (e.g., focal cortical dysplasia) is in Type IIa or Type IIb. In some embodiments, the cortical dysplasia (e.g., focal cortical dysplasia) is in Type IIIa, Type IIIb or Type IIIc. See Kabat et al, Pol. J. Radiol, 2012; 77(2): 35-43.

In some embodiments, the cortical dysplasia (e.g., focal cortical dysplasia) comprises tuberous sclerosis.

In some embodiments, the cortical dysplasia (e.g., focal cortical dysplasia) is characterized by a measurable lesion. In some embodiments, the lesion is in temporal lobe. In some embodiments, the lesion is in extratemporal lobe.

In some embodiments, the cortical dysplasia (e.g., focal cortical dysplasia) is characterized by an ill-defined epilepsy focus. In some embodiments, the cortical dysplasia (e.g., focal cortical dysplasia) is characterized by a secondarily generalized tonic-clonic seizure. In some embodiments, the cortical dysplasia (e.g., focal cortical dysplasia) is characterized by intracranial electrodes application. In some embodiments, the cortical dysplasia (e.g., focal cortical dysplasia) is characterized by extensive resections.

In some embodiments, the cortical dysplasia (e.g., focal cortical dysplasia) is characterized by epilepsy. In some embodiments, the epilepsy is intractable. In some embodiments, the cortical dysplasia (e.g., focal cortical dysplasia) is characterized by mental retardation. In some embodiments, the cortical dysplasia (e.g., focal cortical dysplasia) is characterized by an early onset of seizure. For example, the age at seizure onset is about six months, twelve months, one year, one and a half year, or two years. In some embodiments, the cortical dysplasia (e.g., focal cortical dysplasia) is characterized by a high frequency of the seizures. For example, the seizures occur at least 1×, 2×, 3×, 4×, 5×, 6×, or 7× (i.e., daily) a week. For another example, the seizures occur at least 1×, 2×, or 3× a day. For another example, the seizures occur at least 1×, 2×, 3×, 4×, 5×, 6×, 7×, 8×, 9×, or 10× a month.

In some embodiments, the cortical dysplasia (e.g., focal cortical dysplasia) is characterized by a prior resection surgery. In some embodiments, the prior resection surgery is performed within half a year, a year, one and a half year, or two years of the onset of the disease symptom (e.g., epilepsy). In some embodiments, the resection surgery is performed when the individual is less than half a year, a year, one and a half years, two years, five years, eight years, twelve years, fifteen years, or eighteen years old. In some embodiments, the surgery is a focal or lobar resection surgery. In some embodiments, the surgery is a hemispheric resection surgery. In some embodiments, the resection is a total resection (i.e., the resection of lesion visible on MRI or epileptic focus determined by intracranial EEG). In some embodiments, the resection is a subtotal resection. See Kabat et al, Pol. J. Radiol, 2012; 77(2): 35-43.

In some embodiments, the surgery comprises a temporal resection. In some embodiments, the surgery does not comprise an extratemporal resection. In some embodiments, the surgery comprises an extratemporal resection. In some embodiments, the surgery does not comprise a temporal resection. In some embodiments, the epilepsy is characterized by a period of zero seizure following the surgery. In some embodiments, the period is about 1, 2, 3, 4, 5, 6 months.

In some embodiments, the individual is less than 1, 2, 3, 5, 10, 15, 16, 18, or 26 years old. In some embodiments, the individual is more than about 0.5, 1, 1.5, 2, 3, 5, 10, 15, 16, 18, or 26 years old. In some embodiments, the individual is about 0-26, 1-26, 2-26, or 3-26 years old.

Individual

In some embodiments, the individual is a mammal. In some embodiments, the individual is a human.

In some embodiments, the individual is less than 1, 2, 3, 5, 10, 12, 15, 16, 18, or 26 years old. In some embodiments, the individual is more than about 0.5, 1, 1.5, 2, 3, 5, 10, 12, 15, 16, 18, or 26 years old. In some embodiments, the individual is about 0-26, 1-26, 2-26, 3-26, 0-18, 0-15, or 0-12 years old.

In some embodiments, the individual is a male.

In some embodiments, the individual is diagnosed with medically intractable epilepsy. The medically intractable epilepsy is defined by the failure of at least 2 appropriately dosed and tolerated AEDs to eliminate all clinical seizures over a six months period. In some embodiments, the AED treatment(s) is prior to an epilepsy surgery.

In some embodiments, the individual has been subjected to respective epilepsy surgery (i.e., epilepsy resection surgery).

In some embodiments, the individual has clinical seizures that persist at least 1, 2, or 3 months. In some embodiments, the clinical seizures occur after the respective epilepsy surgery.

In some embodiments, the individual has at least 1, 2, 3, 4, 5, 6, 7, 8, or 9 seizures in the last 30 days prior to the initiation of the treatment. In some embodiments, the individual dos not have a seizure freedom that lasts longer than 7 days, 10 days or 14 days in the last 30 days prior to the initiation of the treatment. In some embodiments, the individual has at least 8 or 9 seizures in the last 30 days without 2 weeks of seizure freedom prior to the initiation of the treatment.

In some embodiments, the individual has relatively low rate of seizures at baseline. For example, in some embodiments, the individual has no more than an average of about 10, 9, 8, 7, 6, 5, 4, 3, or 2 seizures a week in the last 30 days prior to the initiation of the treatment.

In some embodiments, the individual has relatively high rate of seizures at baseline. For example, in some embodiments, the individual has at least an average of about 12, 13, 14, 15, 16, 17, 18, 19, 20, 21, 22, 23 or 24 seizures a week in the last 30 days prior to the initiation of the treatment.

In some embodiments, the individual has cortical dysplasia (such as type 2A and/or type 2B). In some embodiments, the individual has intractable infantile spasms. In some embodiments, the individual has left-sided congenital hemiparesis.

In some embodiments, the individual has not been subjected to a resection surgery. In some embodiments, the individual has been subjected to a resection surgery. In some embodiments, the surgery is performed within half a year, a year, one and a half year, or two years of the onset of the disorder (e.g., epilepsy). In some embodiments, the surgery is performed when the individual is less than half a year, a year, one and a half years, two years, five years, eight years, twelve years, fifteen years, or eighteen years old. In some embodiments, the surgery is a focal or lobar resection surgery. In some embodiments, the surgery is a hemispheric resection surgery. In some embodiments, the resection is a total resection (i.e., the resection of lesion visible on MRI or epileptic focus determined by intracranial EEG). In some embodiments, the resection is a subtotal resection. See Kabat et al, Pol. J. Radiol, 2012; 77(2): 35-43. In some embodiments, the surgery comprises a temporal resection. In some embodiments, the surgery does not comprise an extratemporal resection. In some embodiments, the surgery comprises an extratemporal resection. In some embodiments, the surgery does not comprise a temporal resection. In some embodiments, the prior resection surgery is performed within half a year, a year, one and a half year, or two years of the onset of the disease symptom (e.g., epilepsy).

In some embodiments, the individual has a period of zero seizure following the surgery. In some embodiments, the period is about 1, 2, 3, 4, 5, or 6 months. In some embodiments, the period is about 1, 2, 3, or 4 weeks. In some embodiments, the individual has at least 1, 2, 3, 4, 5, 6, 7, 8, 9, or 10 seizures in about 1, 2, 3, 4, 5, 6 months following the surgery. In some embodiments, the individual has at least 1, 2, 3, 4, 5, 6, 7, 8, 9, or 10 seizures in about 1, 2, 3, or 4 weeks following the surgery.

In some embodiments, the individual has at least 1, 2, 3, 4, or 5 measurable lesions by RANO criteria (≥10 mm in 2 perpendicular diameters).

In some embodiments, the individual has been subjected to radiation therapy prior to the treatment. In some embodiments, it has been at least 1, 2, 3, 4, 5, 6, 7, 8, 9, 10, 11, or 12 weeks after the radiation therapy when the administering of the nanoparticle composition and/or the second agent is initiated.

In some embodiments, the individual has a new lesion outside of the radiation field after the radiation therapy. In some embodiments, the individual has a relapse after the radiation therapy. In some embodiments, the individual has a recurrent glioblastoma, and the recurrent glioblastoma is at least 4, 6, or 8 weeks apart from the previous occurrence of the glioblastoma. In some embodiments, the individual has a new lesion outside of the radiation field, a relapse after the radiation therapy, or the recurrent glioblastoma occurred at least 4, 6, or 8 weeks apart from the previous occurrence of the glioblastoma and the treatment is initiated less than about 1, 2, 3, 4, 5, 6, 7, 8, 9, 10, 11, or 12 weeks after the radiation therapy. In some embodiments, the individual has a Grade 3 or Grade 4 Glioblastoma. In some embodiments, the individual has anaplastic oligodendroglioma (such as Grade 3 anaplastic oligodendroglioma). In some embodiments, the individual is refractory to a prior surgery and/or a prior treatment for glioblastoma (such as standard temozolomide (TMZ)/radiation therapy (RT) treatment, Optune® treatment, marizomib treatment and CAR-T cell immunotherapy).

In some embodiments, the individual has been subjected to an alkylating agent (e.g., temozolomide) prior to the treatment. In some embodiments, the individual has been subjected to both radiation therapy and an alkylating agent (e.g., temozolomide) prior to the treatment.

In some embodiments, the individual has been subjected to a surgical resection prior to the treatment. In some embodiments, it has been at least 1, 2, 3, or 4 weeks after the surgical resection when the administering of the nanoparticle composition and/or the second agent is initiated.

In some embodiments, the individual has not been subjected to an anti-angiogenic agent (e.g., anti-VEGF antibody) prior to the treatment. In some embodiments, the individual has not been subjected to an mTOR inhibitor (e.g., a limus drug, e.g., rapamycin) prior to the treatment. In some embodiments, the individual has not been subjected to either an anti-angiogenic agent, or an mTOR inhibitor prior to the treatment. In some embodiments, the method for treating the CNS disorder in an individual comprises a) systemically (e.g., intravenously or subcutaneously) administering to the individual an effective amount of nanoparticle composition comprising a mTOR inhibitor and an albumin, and b) administering to the individual an anti-VEGF antibody, wherein the individual has not been subjected to either an anti-angiogenic agent, or an mTOR inhibitor prior to the treatment.

In some embodiments, the individual has not been subjected to a proteasome inhibitor (e.g., marizomib) prior to the treatment. In some embodiments, the individual has not been subjected to an mTOR inhibitor (e.g., a limus drug, e.g., rapamycin) prior to the treatment. In some embodiments, the individual has not been subjected to either a proteasome inhibitor or an mTOR inhibitor prior to the treatment. In some embodiments, the method for treating the CNS disorder in an individual comprises a) systemically (e.g., intravenously or subcutaneously) administering to the individual an effective amount of nanoparticle composition comprising a mTOR inhibitor and an albumin, and b) administering to the individual a proteasome inhibitor, wherein the individual has not been subjected to either a proteasome inhibitor, or an mTOR inhibitor prior to the treatment.

In some embodiments, the individual has not been subjected to a local therapy prior to the treatment. In some embodiments, the individual has not been subjected to a systemic therapy prior to the treatment. In some embodiments, the individual has not been subjected to a local therapy or a systemic therapy prior to the treatment.

In some embodiments, the individual has a Karnofsky Performance Status score of at least 50%, 55%, 60%, 65%, or 70%.

In some embodiments, the individual has at least 1, 2, 3, 4, or 5 seizures every month that persist after being treated with at least two, three, or four anti-epilepsy drugs (AED) or a non-invasive treatment (for example, a non-invasive treatment that interferes with cell (such as glioblastoma cancer cell division), for example by creating low-intensity, wave-like electric fields called tumor treating fields, e.g., Optune® treatment).

In some embodiments, the individual has a seizure onset of before the age of six months, twelve months, one year, one and a half year, two years, three years, four years, five years, six years, nine years, twelve years, fifteen years or eighteen years.

In some embodiments, the individual has a mental retardation, perinatal anoxia, a history of neonatal convulsion, and/or a history of status epilepticus.

In some embodiments, the individual has frequent seizures (e.g., at least 1×, 2×, 3×, 4×, 5×, 6×, 7×, 8×, 9×, or 10× seizure(s) a month). For another example, the individual has at least 1×, 2×, 3×, 4×, 5×, 6×, or 7× (i.e., daily) seizure(s) a week. For another example, the individual has at least 1×, 2×, or 3× seizure(s) a day.

In some embodiments, the individual has frequent initial seizures (e.g., at least 1×, 2×, 3×, 4×, 5×, 6×, 7×, 8×, 9×, or 10× seizure(s) in the first month, or first two, three, four, five, six, nine, twelve, or twenty-four months). For another example, the individual has at least 1×, 2×, 3×, 4×, 5×, 6×, or 7× (i.e., daily) seizure(s) in the first week. For another example, the individual has at least 1×, 2×, 3×, 4×, 5×, 6×, or 7× seizure(s) in the first day, or the first two, three, four, five or six days.

In some embodiments, the individual has at least 1, 2, 3, 4, 5, 6, 7, 8, 9, 10, 11, or 12 events of abnormal electroencephalography (EEG) finding(s) during a seizure. In some embodiments, the seizure is a partial seizure (i.e., focal seizure). In some embodiments, the EEG is a focal EEG. In some embodiments, the seizure is a generalized seizure. In some embodiments, the abnormal EEG finding(s) comprises a finding in the frontal lobes. In some embodiments, the abnormal EEG finding(s) comprise a finding in the temporal lobes. In some embodiments, the abnormal EEG finding(s) comprise a finding in the parietal lobes. In some embodiments, the abnormal EEG finding(s) comprise a finding in the occipital lobes. In some embodiments, the individual has a diffuse EEG pattern.

In some embodiments, the individual has intractable epilepsy developed before the age of 6 months, 9 months, 12 months, 18 months, one year, one and a half year, two years, three years, four years, five years, six years, twelve years, or eighteen years.

In some embodiments, the individual has a prior epilepsy surgery. In some embodiments, the prior epilepsy surgery is performed within half a year, a year, one and a half year, or two years of the epilepsy onset. In some embodiments, the epilepsy surgery is performed when the individual is less than half a year, a year, one and a half years, two years, five years, eight years, twelve years, fifteen years, or eighteen years old. In some embodiments, the surgery is a focal or lobar resection surgery. In some embodiments, the surgery is a hemispheric resection surgery. In some embodiments, the resection is a total resection (i.e., the resection of lesion visible on MRI or epileptic focus determined by intracranial EEG). In some embodiments, the resection is a subtotal resection. See Kabat et al, Pol. J. Radiol, 2012; 77(2): 35-43.

In some embodiments, the surgery comprises a temporal resection. In some embodiments, the surgery does not comprise an extratemporal resection. In some embodiments, the surgery comprises an extratemporal resection. In some embodiments, the surgery does not comprise a temporal resection. In some embodiments, the epilepsy is characterized by a period of zero seizure following the surgery. In some embodiments, the period is about 1, 2, 3, 4, 5, 6 months.

In some embodiments, the individual has an ill-defined epilepsy focus. In some embodiments, the individual has a secondarily generalized tonic-clonic seizure. In some embodiments, the individual has extensive resections.

In some embodiments, the individual has an early onset of seizure. For example, the age at seizure onset is about six months, twelve months, one year, one and a half year, or two years.

In some embodiments, the individual has epilepsy and is refractory to surgery or at least one antiepileptic drug. In some embodiments, the individual has epilepsy and is refractory to both surgery and at least one antiepileptic drug.

Nanoparticle Compositions

The mTOR inhibitor nanoparticle compositions described herein comprise nanoparticles comprising (in various embodiments consisting essentially of or consisting of) an mTOR inhibitor (such as a limus drug, e.g., sirolimus or a derivative thereof) and an albumin (such as human serum albumin). Nanoparticles of poorly water soluble drugs (such as macrolides) have been disclosed in, for example, U.S. Pat. Nos. 5,916,596; 6,506,405; 6,749,868, 6,537,579, 7,820, 788, and 8,911,786, and also in U.S. Pat. Pub. Nos. 2006/0263434, and 2007/0082838; PCT Patent Application WO08/137148, each of which is incorporated herein by reference in their entirety.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 10 to about 400 nm. In some embodiments, the average or mean diameter of the nanoparticles is about 10 to about 150 nm. In some embodiments, the average or mean diameter of the nanoparticles is about 40 to about 120 nm. In some embodiments, the average or mean diameter of the nanoparticles are no less than about 50 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 10 nm to about 400 nm, including for example about 10 nm to about 200 nm, about 20 nm to about 200 nm, about 30 nm to about 180 nm, about 40 nm to about 150 nm, about 40 nm to about 120 nm, and about 60 nm to about 100 nm.

Methods of determining average particle sizes are known in the art, for example, dynamic light scattering (DLS) has been routinely used in determining the size of submicrometre-sized particles based. International Standard ISO22412 Particle Size Analysis-Dynamic Light Scattering, International Organisation for Standardisation (ISO) 2008 and Dynamic Light Scattering Common Terms Defined, Malvern Instruments Limited, 2011. In some embodiments, the particle size is measured as the volume-weighted mean particle size (Dv50) of the nanoparticles in the composition.

In some embodiments, the nanoparticles comprise the mTOR inhibitor associated with the albumin. In some embodiments, the nanoparticles comprise the mTOR inhibitor coated with the albumin.

In some embodiments, the albumin has sulfhydryl groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprising the mTOR inhibitor (such as a limus drug, e.g., sirolimus or a derivative thereof) are associated (e.g., coated) with an albumin (such as human albumin or human serum albumin). In some embodiments, the composition comprises an mTOR inhibitor (such as a limus drug, e.g., sirolimus or a derivative thereof) in both nanoparticle and non-nanoparticle forms (e.g., in the form of solutions or in the form of soluble albumin/nanoparticle complexes), wherein at least about any one of 50%, 60%, 70%, 80%, 90%, 95%, or 99% of the mTOR inhibitor in the composition are in nanoparticle form. In some embodiments, the mTOR inhibitor (such as a limus drug, e.g., sirolimus or a derivative thereof) in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of an mTOR inhibitor (such as a limus drug, e.g., sirolimus or a derivative thereof) that is substantially free of polymeric materials (such as polymeric matrix).

In some embodiments, the composition comprises an albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of an albumin (such as human albumin or human serum albumin) and a mTOR inhibitor (such as a limus drug, e.g., sirolimus or a derivative thereof) in the mTOR inhibitor nanoparticle composition is about 18:1 or less, such as about 15:1 or less, for example about 10:1 or less. In some embodiments, the weight ratio of an albumin (such as human albumin or human serum albumin) and an mTOR inhibitor (such as a limus drug, e.g., sirolimus or a derivative thereof) in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of an albumin and an mTOR inhibitor (such as a limus drug, e.g., sirolimus or a derivative thereof) in the nanoparticle portion of the composition is about any one of 1:2, 1:3, 1:4, 1:5, 1:9, 1:10, 1:15, or less. In some embodiments, the weight ratio of the albumin (such as human albumin or human serum albumin) and the mTOR inhibitor (such as a limus drug, e.g., sirolimus or a derivative thereof) in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the mTOR inhibitor nanoparticle composition (such as sirolimus/albumin nanoparticle composition) comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises an albumin (such as human albumin or human serum albumin). The albumin may either be natural in origin or synthetically prepared. In some embodiments, the albumin is human albumin or human serum albumin. In some embodiments, the albumin is a recombinant albumin.

Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulfide bridges, one free thiol (Cys 34), and a single tryptophan (Trp 214). Intravenous use of HSA solution has been indicated for the prevention and treatment of hypovolemic shock (see, e.g., Tullis, *JAMA*, 237: 355-360, 460-463, (1977)) and Houser et al., *Surgery, Gynecology and Obstetrics*, 150: 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context). Human serum albumin (HSA) has multiple hydrophobic binding sites (a total of eight for fatty acids, an endogenous ligand of HSA) and binds a diverse set of drugs, especially neutral and negatively charged hydrophobic compounds (Goodman et al., The Pharmacological Basis of Therapeutics, $9^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Rapamycin and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(b), 147-51 (1996)).

In some embodiments, the composition described herein is substantially free (such as free) of surfactants, such as Cremophor (or polyoxyethylated castor oil, including Cremophor EL® (BASF)). In some embodiments, the mTOR inhibitor nanoparticle composition (such as sirolimus/albumin nanoparticle composition) is substantially free (such as free) of surfactants. A composition is "substantially free of Cremophor" or "substantially free of surfactant" if the amount of Cremophor or surfactant in the composition is not sufficient to cause one or more side effect(s) in an individual when the mTOR inhibitor nanoparticle composition (such as sirolimus/albumin nanoparticle composition) is administered to the individual. In some embodiments, the mTOR inhibitor nanoparticle composition (such as sirolimus/albumin nanoparticle composition) contains less than about any one of 20%, 15%, 10%, 7.5%, 5%, 2.5%, or 1% organic solvent or surfactant. In some embodiments, the albumin is human albumin or human serum albumin. In some embodiments, the albumin is recombinant albumin.

The amount of an albumin in the composition described herein will vary depending on other components in the composition. In some embodiments, the composition comprises an albumin in an amount that is sufficient to stabilize the mTOR inhibitor (such as a limus drug, e.g., sirolimus or a derivative thereof) in an aqueous suspension, for example, in the form of a stable colloidal suspension (such as a stable suspension of nanoparticles). In some embodiments, the albumin is in an amount that reduces the sedimentation rate of the mTOR inhibitor (such as a limus drug, e.g., sirolimus or a derivative thereof) in an aqueous medium. For particle-containing compositions, the amount of the albumin also depends on the size and density of nanoparticles of the mTOR inhibitor.

An mTOR inhibitor (such as a limus drug, e.g., sirolimus or a derivative thereof) is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as a human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed using an optical microscope at 1000 times, at about fifteen minutes after preparation of the suspension. Stability can also be evaluated under accelerated testing conditions, such as at a temperature that is about 40° C. or higher.

In some embodiments, the albumin is present in an amount that is sufficient to stabilize the mTOR inhibitor (such as a limus drug, e.g., sirolimus or a derivative thereof) in an aqueous suspension at a certain concentration. For example, the concentration of the mTOR inhibitor (such as a limus drug, e.g., sirolimus or a derivative thereof) in the composition is about 0.1 to about 100 mg/ml, including for example about any of 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the mTOR inhibitor (such as a limus drug, e.g., sirolimus or a derivative thereof) is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g., about 0.5% (w/v), about 5% (w/v), about 10% (w/v), about 15% (w/v), about 20% (w/v), about 30% (w/v), about 40% (w/v), or about 50% (w/v)) of an albumin. In some embodiments, the composition, in liquid form, comprises about 0.5% to about 5% (w/v) of albumin.

In some embodiments, the weight ratio of the albumin to the mTOR inhibitor (such as a limus drug, e.g., sirolimus or a derivative thereof) in the mTOR inhibitor nanoparticle composition is such that a sufficient amount of mTOR inhibitor binds to, or is transported by, the cell. While the weight ratio of an albumin to an mTOR inhibitor (such as a limus drug, e.g., sirolimus or a derivative thereof) will have to be optimized for different albumin and mTOR inhibitor combinations, generally the weight ratio of an albumin to an mTOR inhibitor (such as a limus drug, e.g., sirolimus or a derivative thereof) (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to mTOR inhibitor (such as a limus drug, e.g., sirolimus or a derivative thereof) weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human albumin or human serum albumin) to the mTOR inhibitor (such as a limus drug, e.g., sirolimus or a derivative thereof) in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the albumin allows the composition to be administered to an individual (such as a human) without significant side effects. In some embodiments, the albumin (such as human serum albumin or human albumin) is in an amount that is effective to reduce one or more side effects of administration of the mTOR inhibitor (such as a limus drug, e.g., sirolimus or a derivative thereof) to a human. The term "reducing one or more side effects" of administration of the mTOR inhibitor (such as a limus drug, e.g., sirolimus or a derivative thereof) refers to reduction, alleviation, elimination, or avoidance of one or more undesirable effects caused by the mTOR inhibitor, as well as side effects caused by delivery vehicles (such as solvents that render the limus drugs suitable for injection) used to deliver the mTOR inhibitor. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with limus drugs (such as a limus drug, e.g., sirolimus or a derivative thereof) can be reduced.

In some embodiments, the mTOR inhibitor nanoparticle compositions described herein comprise nanoparticles comprising an mTOR inhibitor (such as a limus drug, e.g., sirolimus or a derivative thereof) and an albumin (such as human albumin or human serum albumin), wherein the nanoparticles have an average diameter of no greater than about 200 nm. In some embodiments, the mTOR inhibitor nanoparticle compositions described herein comprise nanoparticles comprising an mTOR inhibitor (such as a limus drug, e.g., sirolimus or a derivative thereof) and an albumin (such as human albumin or human serum albumin), wherein the nanoparticles have an average diameter of no greater than about 150 nm. In some embodiments, the mTOR inhibitor nanoparticle compositions described herein comprise nanoparticles comprising an mTOR inhibitor (such as a limus drug, e.g., sirolimus or a derivative thereof) and an albumin (such as human albumin or human serum albumin), wherein the nanoparticles have an average diameter of no greater than about 150 nm (for example about 100-120 nm, for example about 100 nm). In some embodiments, the mTOR inhibitor nanoparticle compositions described herein comprise nanoparticles comprising sirolimus and human albumin (such as human serum albumin), wherein the nanoparticles have an average diameter of no greater than about 150 nm (for example about 100-120 nm, for example about 100 nm). In some embodiments, the mTOR inhibitor nanoparticle compositions described herein comprise nanoparticles comprising sirolimus and human albumin (such as human serum albumin), wherein the average or mean diameter of the nanoparticles is about 10 to about 150 nm. In some embodiments, the mTOR inhibitor nanoparticle compositions described herein comprise nanoparticles comprising sirolimus and human albumin (such as human serum albumin), wherein the average or mean diameter of the nanoparticles is about 40 to about 120 nm.

In some embodiments, the mTOR inhibitor nanoparticle compositions described herein comprise nanoparticles comprising an mTOR inhibitor (such as a limus drug, e.g., sirolimus or a derivative thereof) and an albumin (such as human albumin or human serum albumin), wherein the nanoparticles have an average diameter of no greater than about 200 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) and an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) and an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising sirolimus and human albumin (such as human serum albumin), wherein the nanoparticles have an average diameter of no greater than about 150 nm (for example about 100-120 nm, for example about 100 nm), wherein the weight ratio of albumin and mTOR inhibitor in the composition is about 9:1 or about 8:1. In some embodiments, the average or mean diameter of the nanoparticles is about 10 nm to about 150 nm. In some embodiments, the average or mean diameter of the nanoparticles is about 40 nm to about 120 nm.

In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin). In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the nanoparticles have an average diameter of no greater than about 200 nm. In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the nanoparticles have an average diameter of no greater than about 150 nm. In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the nanoparticles have an average diameter of about 10 nm to about 150 nm. In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the nanoparticles have an average diameter of about 40 nm to about 120 nm. In some embodiments, the mTOR inhibitor nanoparticle compositions described herein comprise nanoparticles comprising sirolimus associated (e.g., coated) with human albumin (such as human serum albumin), wherein the nanoparticles have an average diameter of no greater than about 150 nm (for example about 100-120 nm, for example about 100 nm). In some embodiments, the mTOR inhibitor nanoparticle compositions described herein comprise nanoparticles comprising sirolimus associated (e.g., coated) with human albumin (such as human serum albumin), wherein the nanoparticles have an average diameter of about 10 nm to about 150 nm. In some embodiments, the mTOR inhibitor nanoparticle compositions described herein comprise nanoparticles comprising sirolimus associated (e.g., coated) with human albumin (such as human serum albumin), wherein the nanoparticles have an average diameter of about 40 nm to about 120 nm.

In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the nanoparticles have an average diameter of no greater than about 200 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) associated (e.g., coated) with an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising sirolimus associated (e.g., coated) with human albumin (such as human serum albumin), wherein the nanoparticles have an average diameter of no greater than about 150 nm (for example about 100-120 nm, for example about 100 nm), wherein the weight ratio of albumin and the sirolimus in the composition is about 9:1 or about 8:1. In some embodiments, the average or mean diameter of the nanoparticles is about 10 nm to about 150 nm. In some embodiments, the average or mean diameter of the nanoparticles is about 40 nm to about 120 nm.

In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin). In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin), wherein the nanoparticles have an average diameter of no greater than about 200 nm. In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin), wherein the nanoparticles have an average diameter of no greater than about 150 nm. In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin), wherein the nanoparticles have an average diameter of no greater than about 150 nm (for example about 100-120 nm, for example about 100 nm). In some embodiments, the mTOR inhibitor nanoparticle compositions described herein comprise nanoparticles comprising sirolimus stabilized by human albumin (such as human serum albumin), wherein the nanoparticles have an average diameter of no greater than about 150 nm (for example about 100-120 nm, for example about 100 nm). In some embodiments, the average or mean diameter of the nanoparticles is about 10 nm to about 150 nm. In some embodiments, the average or mean diameter of the nanoparticles is about 40 nm to about 120 nm.

In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin), wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin), wherein the nanoparticles have an average diameter of no greater than about 200 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising an mTOR inhibitor (such as a limus drug, e.g., sirolimus or a derivative thereof) stabilized by an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the mTOR inhibitor nanoparticle compositions described herein comprise nanoparticles comprising sirolimus stabilized by human albumin (such as human serum albumin), wherein the nanoparticles have an average diameter of no greater than about 150 nm (for example about 100-120 nm, for example about 100 nm), wherein the weight ratio of albumin and the sirolimus in the composition is about 9:1 or about 8:1. In some embodiments, the average or mean diameter of the nanoparticles is about 10 nm to about 150 nm. In some embodiments, the average or mean diameter of the nanoparticles is about 40 nm to about 120 nm.

In some embodiments, the mTOR inhibitor nanoparticle composition comprises nab-sirolimus. In some embodiments, the mTOR inhibitor nanoparticle composition is nab-sirolimus. Nab-sirolimus is a formulation of sirolimus stabilized by human albumin USP, which can be dispersed in directly injectable physiological solution. The weight ratio of human albumin and sirolimus is about 8:1 to about 9:1. When dispersed in a suitable aqueous medium such as 0.9% sodium chloride injection or 5% dextrose injection, nab-sirolimus forms a stable colloidal suspension of sirolimus. The mean particle size of the nanoparticles in the colloidal suspension is about 100 nanometers. Since HSA is freely soluble in water, nab-sirolimus can be reconstituted in a wide range of concentrations ranging from dilute (0.1 mg/ml sirolimus or a derivative thereof) to concentrated (20 mg/ml sirolimus or a derivative thereof), including for example about 2 mg/ml to about 8 mg/ml, or about 5 mg/ml.

Methods of making nanoparticle compositions are known in the art. For example, nanoparticles containing an mTOR inhibitor (such as a limus drug, e.g., sirolimus or a derivative thereof) and an albumin (such as human serum albumin or human albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579, 7,820,788, and 8,911,786, and also in U. S. Pat. Pub. Nos. 2007/0082838, 2006/0263434 and PCT Application WO08/137148.

Briefly, the mTOR inhibitor (such as a limus drug, e.g., sirolimus or a derivative thereof) is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1,4:1, 5:1, 6:1,7:1, 8:1, or 9:1).

A. mTOR Inhibitor

The methods described herein in some embodiments comprise administration of nanoparticle compositions of mTOR inhibitors. "mTOR inhibitor" used herein refers to an inhibitor of mTOR. mTOR is a serine/threonine-specific protein kinase downstream of the phosphatidylinositol 3-kinase (PI3K)/Akt (protein kinase B) pathway, and a key regulator of cell survival, proliferation, stress, and metabolism. mTOR pathway dysregulation has been found in many human carcinomas, and mTOR inhibition produced substantial inhibitory effects on tumor progression.

The mammalian target of rapamycin (mTOR) (also known as mechanistic target of rapamycin or FK506 binding protein 12-rapamycin associated protein 1 (FRAP1)) is an atypical serine/threonine protein kinase that is present in two distinct complexes, mTOR Complex 1 (mTORC1) and mTOR Complex 2 (mTORC2). mTORC1 is composed of mTOR, regulatory-associated protein of mTOR (Raptor), mammalian lethal with SEC13 protein 8 (MLST8), PRAS40 and DEPTOR (Kim et al. (2002). Cell 110: 163-75; Fang et al. (2001). Science 294 (5548): 1942-5). mTORC1 integrates four major signal inputs: nutrients (such as amino acids and phosphatidic acid), growth factors (insulin), energy and stress (such as hypoxia and DNA damage). Amino acid availability is signaled to mTORC1 via a pathway involving the Rag and Ragulator (LAMTOR1-3) Growth factors and hormones (e.g., insulin) signal to mTORC1 via Akt, which inactivates TSC2 to prevent inhibition of mTORC1. Alternatively, low ATP levels lead to the AMPK-dependent activation of TSC2 and phosphorylation of raptor to reduce mTORC1 signaling proteins.

Active mTORC1 has a number of downstream biological effects including translation of mRNA via the phosphorylation of downstream targets (4E-BP1 and p70 S6 Kinase), suppression of autophagy (Atg13, ULK1), ribosome biogenesis, and activation of transcription leading to mitochondrial metabolism or adipogenesis. Accordingly, mTORC1 activity promotes either cellular growth when conditions are favorable or catabolic processes during stress or when conditions are unfavorable.

mTORC2 is composed of mTOR, rapamycin-insensitive companion of mTOR (RICTOR), GβL, and mammalian stress-activated protein kinase interacting protein 1 (mSIN1). In contrast to mTORC1, for which many upstream signals and cellular functions have been defined (see above), relatively little is known about mTORC2 biology. mTORC2 regulates cytoskeletal organization through its stimulation of F-actin stress fibers, paxillin, RhoA, Rac1, Cdc42, and protein kinase C α (PKCα). It had been observed that knocking down mTORC2 components affects actin polymerization and perturbs cell morphology (Jacinto et al. (2004). Nat. Cell Biol. 6, 1122-1128; Sarbassov et al. (2004). Curr. Biol. 14, 1296-1302). This suggests that mTORC2 controls the actin cytoskeleton by promoting protein kinase Cα (PKCα) phosphorylation, phosphorylation of paxillin and its relocalization to focal adhesions, and the GTP loading of RhoA and Rac1. The molecular mechanism by which mTORC2 regulates these processes has not been determined.

In some embodiments, the mTOR inhibitor (such as a limus drug, e.g., sirolimus or a derivative thereof) is an inhibitor of mTORC1. In some embodiments, the mTOR inhibitor (such as a limus drug, e.g., sirolimus or a derivative thereof) is an inhibitor of mTORC2. In some embodiments, the mTOR inhibitor (such as a limus drug, e.g., sirolimus or a derivative thereof) is an inhibitor of both mTORC1 and mTORC2.

In some embodiments, the mTOR inhibitor is a limus drug, which includes sirolimus and its analogs. Examples of limus drugs include, but are not limited to, temsirolimus (CCI-779), everolimus (RAD001), ridaforolimus (AP-23573), deforolimus (MK-8669), zotarolimus (ABT-578), pimecrolimus, and tacrolimus (FK-506). In some embodiments, the limus drug is selected from the group consisting of temsirolimus (CCI-779), everolimus (RAD001), ridaforolimus (AP-23573), deforolimus (MK-8669), zotarolimus (ABT-578), pimecrolimus, and tacrolimus (FK-506). In some embodiments, the mTOR inhibitor is an mTOR kinase inhibitor, such as CC-115 or CC-223.

In some embodiments, the mTOR inhibitor is sirolimus. Sirolimus is macrolide antibiotic that complexes with FKBP-12 and inhibits the mTOR pathway by binding mTORC1.

In some embodiments, the mTOR inhibitor is selected from the group consisting of sirolimus (rapamycin), BEZ235 (NVP-BEZ235), everolimus (also known as RAD001, Zortress, Certican, and Afinitor), AZD8055, temsirolimus (also known as CCI-779 and Torisel), CC-115, CC-223, PI-103, Ku-0063794, INK 128, AZD2014, NVP-BGT226, PF-04691502, CH5132799, GDC-0980 (RG7422), Torin 1, WAY-600, WYE-125132, WYE-687, GSK2126458, PF-05212384 (PKI-587), PP-121, OSI-027, Palomid 529, PP242, XL765, GSK1059615, WYE-354, and ridaforolimus (also known as deforolimus).

BEZ235 (NVP-BEZ235) is an imidazoquilonine derivative that is an mTORC1 catalytic inhibitor (Roper J, et al. PLoS One, 2011, 6(9), e25132). Everolimus is the 40-O-(2-hydroxyethyl) derivative of sirolimus and binds the cyclophilin FKBP-12, and this complex also mTORC1. AZD8055 is a small molecule that inhibits the phosphorylation of mTORC1 (p70S6K and 4E-BP1). Temsirolimus is a small molecule that forms a complex with the FK506-binding protein and prohibits the activation of mTOR when it resides in the mTORC1complex. PI-103 is a small molecule that inhibits the activation of the rapamycin-sensitive (mTORC1) complex (Knight et al. (2006) Cell. 125: 733-47). KU-0063794 is a small molecule that inhibits the phosphorylation of mTORC1 at Ser2448 in a dose-dependent and time-dependent manner. INK 128, AZD2014, NVP-BGT226, CH5132799, WYE-687, and are each small molecule inhibitors of mTORC1. PF-04691502 inhibits mTORC1 activity. GDC-0980 is an orally bioavailable small molecule that inhibits Class I PI3 Kinase and TORC1. Torin 1 is a potent small molecule inhibitor of mTOR. WAY-600 is a potent, ATP-competitive and selective inhibitor of mTOR. WYE-125132 is an ATP-competitive small molecule inhibitor of mTORC1. GSK2126458 is an inhibitor of mTORC1. PKI-587 is a highly potent dual inhibitor of PI3Kα, PI3Kγ and mTOR. PP-121 is a multi-target inhibitor of PDGFR, Hck, mTOR, VEGFR2, Src and Abl. OSI-027 is a selective and potent dual inhibitor of mTORC1 and mTORC2 with IC50 of 22 nM and 65 nM, respectively. Palomid 529 is a small molecule inhibitor of mTORC1 that lacks affinity for ABCB1/ABCG2 and has good brain penetration (Lin et al. (2013) Int J Cancer DOI: 10.1002/ijc. 28126 (e-published ahead of print). PP242 is a selective mTOR inhibitor. XL765 is a dual inhibitor of mTOR/PI3k for mTOR, p110α, p110β, p110γ and p110δ. GSK1059615 is a novel and dual inhibitor of PI3Kα, PI3Kβ, PI3Kδ, PI3Kγ and mTOR. WYE-354 inhibits mTORC1 in HEK293 cells (0.2 µM-5 µM) and in HUVEC cells (10 nM-1 µM). WYE-354 is a potent, specific and ATP-competitive inhibitor of mTOR. Deforolimus (Ridaforolimus, AP23573, MK-8669) is a selective mTOR inhibitor.

B. Other Components in the mTOR Inhibitor Nanoparticle Composition

The nanoparticles described herein can be present in a composition that includes other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the mTOR inhibitor nanoparticle composition (such as sirolimus/albumin nanoparticle composition) (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of about any of 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Second Agent

The second agent described herein can be any medication or therapy that is useful for treating a CNS disorder.

In some embodiments, the second agent is an anti-epilepsy drug.

In some embodiments, the second agent is capable of penetrating blood brain barrier (BBB).

In some embodiments, the second agent is angiogenesis inhibitor (e.g., an anti-VEGF antibody). In some embodiments, the second agent is a proteasome inhibitor (e.g., marizomib). In some embodiments, the second agent is an alkylating agent (e.g., temozolomide, lomustine). In some embodiments, the second agent is a VEGFR inhibitor.

A. Anti-VEGF Antibody

Angiogenesis is an important cellular event in which vascular endothelial cells proliferate, prune and reorganize to form new vessels from preexisting vascular network. Angiogenesis is also implicated in the pathogenesis of a variety of disorders, including but not limited to, tumors, proliferative retinopathies, age-related macular degeneration, rheumatoid arthritis (RA), and psoriasis. Angiogenesis is essential for the growth of most primary tumors and their subsequent metastasis. Tumors can absorb sufficient nutrients and oxygen by simple diffusion up to a size of 1-2 mm, at which point their further growth requires the elaboration of vascular supply. This process is thought to involve recruitment of the neighboring host mature vasculature to begin sprouting new blood vessel capillaries, which grow towards, and subsequently infiltrate, the tumor mass. In addition, tumor angiogenesis involve the recruitment of circulating endothelial precursor cells from the bone marrow to promote neovascularization. Kerbel (2000) *Carcinogenesis* 21:505-515; Lynden et al. (2001) *Nat. Med.* 7:1194-1201.

Vascular endothelial cell growth factor (VEGF), which is also termed VEGF-A or vascular permeability factor (VPF), is a pivotal regulator of both normal and abnormal angiogenesis. Ferrara and Davis-Smyth (1997) *Endocrine Rev.* 18:4-25; Ferrara (1999) *J. Mol. Med.* 77:527-543.

The terms "VEGF" and "VEGF-A" are used interchangeably to refer to the 165-amino acid vascular endothelial cell growth factor and related 121-, 189-, and 206-amino acid vascular endothelial cell growth factors, as described by Leung et al. *Science*, 246:1306 (1989), and Houck et al. *Mol. Endocrin.*, 5:1806 (1991), together with the naturally occurring allelic and processed forms thereof. In some embodiments, the term "VEGF" is also used to refer to truncated forms of the polypeptide comprising amino acids 8 to 109 or 1 to 109 of the 165-amino acid human vascular endothelial cell growth factor. The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

The methods described herein in some embodiments comprise administration of an anti-VEGF antibody. An "anti-VEGF antibody" is an antibody that binds to VEGF with sufficient affinity and specificity. In some embodiments, the anti-VEGF antibody is used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as P1GF, PDGF or bFGF. In some embodiments, the anti-VEGF antibody is a monoclonal antibody. In some embodiments, the anti-VEGF antibody binds to the same epitope as the monoclonal anti-VEGF antibody A4.6.1 produced by hybridoma ATCC HB 10709. In some embodiments, the anti-VEGF antibody is a recombinant antibody. In some embodiments, the anti-VEGF antibody is a humanized antibody. In some embodiments, the anti-VEGF is a recombinant humanized antibody. In some embodiments, the recombinant humanized anti-VEGF antibody is an antibody generated according to Presta et al. (1997) *Cancer Res.* 57:4593-4599, including but not limited to the antibody known as bevacizumab (BV; Avastin™)

In some embodiments, the anti-VEGF antibody is a fragment of an anti-VEGF antibody (e.g., a Fab fragment). In some embodiments, the anti-VEGF antibody is Ranibizumab.

In some embodiments, the anti-VEGF antibody is capable of penetrating blood brain barrier (BBB).

B. Proteasome Inhibitor

The term "proteasome" refers to the 26S proteasome, as describe e.g. in Coux, O., Tanaka, K. and Goldberg, A., Ann. Rev. Biochem. 65 (1996) 801-847; Voges, D., Annu Rev Biochem. 68 (1999) 1015-68 or Kisselev, A. L., et al., Chem Biol Vol. 8 (8) (2001) 739-758.

The term "proteasome inhibitor" as used herein refers to agents which inhibit the activity of the 26S proteasome. Such proteasome inhibitors include inter alia e.g. peptide derivatives such as peptide aldehydes (e.g. MG132, MGl 15, CEP-1615, PSI, or immunoproteasome specific inhibitor IPSI-OOl (Cbz-LnL-CHO=N-carbobenzyloxy-leucyl-norleucinal, see US 2006/0241056), peptide boronates (e.g. bortezomib (PS-341) or DFLB), peptide epoxyketones (e.g. epoxomicin, dihydroeponemycin, or epoxomicin derivative carfilzomib (PR-171)), or peptide vinyl sulfones (e.g. NLVS) and non-peptide derivatives such as salinosporamide A (NPI-0052), salinosporamide A derivates, lactacystin or lactacystin derivatives (e.g. clasto-lactacystin-L-lactone (omuralide) or PS-519). The different types and structures of said proteasome inhibitors are described e.g. in Kisselev, A. L., et al., Chem Biol Vol. 8 (8) (2001) 739-758, WO 2004/004749 and Joazeiro, C, et al., Cancer Res. 66(16) (2006) 7840-7842), Kanagasabaphy, P., et al., Curr Opin Investig Drugs 8 (2007) 447-51, Adams, J., Nat Rev Cancer 4 (2004) 349-360 and US 2006/0241056.

The proteasome inhibitors described herein include any known proteasome inhibitors, as well as other molecules that can be routinely tested for their ability to inhibit proteasome activity. Various strategies for the identification of such inhibitors are exemplified in the art. For example, small molecule libraries, often comprising extracts from plants or more simple organisms, may be screened for their ability to inhibit specific protease types. Alternatively, a rational design approach may be applied using, for example, peptide or peptidomimetic compounds designed specifically to interact with the active site of a proteasome component (see e.g., Siman, et al., WO91/13904; Powers, et al., in Proteinase Inhibitors, Barrett, et al. (eds.), Elsevier, pp. 55-152 (1986)). The inhibitors can be stable analogs of catalytic transition states such as Z-Gly-Gly-Leu-H, which inhibits the chymotrypsin-like activity of the proteasome (Orlowski, Biochemistry 29: 10289 (1990); see also Kennedy and Schultz, Biochem. 18: 349 (1979)).

In addition, a variety of natural and chemical proteasome inhibitors reported in the literature, or analogs thereof, are intended to be encompassed by the present application including peptides containing an .alpha.-diketone or an .alpha.-ketone ester, peptide chloromethyl ketone, isocoumarins, peptide sulfonyl fluorides, peptidyl boronates, peptide epoxides, and peptidyl diazomethanes. Angelastro, et al., J. Med. Chem. 33: 11 (1990); Bey, et al., EPO 363,284; Bey, et al., EPO 363,284; Bey, et al., EPO 364,344; Grubb, et al., WO 88/10266; Higuchi, et al., EPO 393,457; Ewoldt, et al., Mol. Immunol. 29(6): 713 (1992); Hernandez, et al., J. Med. Chem. 35(6): 1121 (1992); Vlasak, et al., J. Virol. 63(5): 2056 (1989); Hudig, et al., J. Immunol. 147(4): 1360 (1991); Odakc, et al., Biochem. 30(8): 2217 (1991); Vijay-alakshmi, et al., Biochem. 30(8): 2175 (1991); Kam, et al., Thrombosis and Haemostasis 64(1): 133 (1990); Powers, et al., J. Cell. Biochem. 39(1): 33 (1989); Powers, et al., Proteinase Inhibitors, Barrett et al., Eds., Elsevier, pp. 55-152 (1986); Powers, et al., Biochem 29(12): 3108 (1990); Oweida, et al., Thrombosis Res. 58(2): 391 (1990); Hudig, et al., Mol. Immunol. 26(8): 793 (1989); Orlowski, et al., Arch. Biochem. and Biophys. 269(1): 125 (1989); Zunino, et al., Biochem. et Biophys. Acta 967(3): 331 (1988); Kam, et al., Biochem. 27(7): 2547 (1988); Parkes, et al., Biochem. J. 230: 509 (1985); Green, et al., J. Biol. Chem. 256: 1923 (1981); Angliker, et al., Biochem. J. 241: 871 (1987); Puri, et al., Arch. Biochem. Biophys. 27: 346 (1989); Hanada, et al., Proteinase Inhibitors: Medical and Biological Aspects, Katunuma, et al., Eds., Springer-Verlag pp. 25-36 (1983); Kajiwara, et al., Biochem. Int. 15: 935 (1987); Rao, et al., Thromb. Res. 47: 635 (1987); Tsujinaka, et al., Biochem. Biophys. Res. Commun. 153: 1201 (1988)).

Peptide aldehydes and peptide alpha-keto esters containing a hydrophobic residue in the P.sub.1 position tested by Vinitsky, et al. (*Biochem.* 31: 9421 (1992), see also Orlowski, et al., *Biochem.* 32: 1563 (1993)) as potential inhibitors of the chymotrypsin-like activity of the proteasome are also intended to be encompassed by the present application. Other tripeptides that have been described in the literature include Ac-Leu-Leu-Leu-H, Ac-Leu-Leu-Met-OR, Ac-Leu-Leu-Nle-OR, Ac-Leu-Leu-Leu-OR, Ac-Leu-Leu-Arg-H, Z-Leu-Leu-Leu-H, Z-Arg-Leu-Phe-H and Z-Arg-Ile-Phe-H, where OR, along with the carbonyl of the preceding amino acid residue, represents an ester group, and are intended to be encompassed by the present application.

The chymotrypsin-like proteases and their inhibitors disclosed by Siman, et al. (WO 01/13904) are also intended to be encompassed by the present application. These inhibitors have the formula R-A4-A3-A2-Y, wherein R is hydrogen, or an N-terminal blocking group; A4 is a covalent bond, an amino acid or a peptide; A3 is a covalent bond, a D-amino acid, Phe, Tyr, Val or a conservative amino acid substitution of Val; A2 is a hydrophobic amino acid or lysine or a conservative amino acid substitution thereof, or when A4 includes at least two amino acids, A2 is any amino acid; and Y is a group reactive with the active site of said protease. The peptide ketoamides, ketoacids, and ketoesters and their use in inhibiting serine proteases and cysteine proteases disclosed by Powers (WO 92/12140) and the uses for calpain inhibitor compounds and pharmaceutical compositions containing them disclosed by Bartus, et al. (WO 92/1850) are also intended to be encompassed by the present application.

The following compounds, or analogues thereof, are also contemplated to be used as proteasome inhibitors in the present application: Calpain Inhibitor I, MG101, Calpain Inhibitor II, Epoxomicin, Fraction I (FrI, Hela), Fraction II (FII), clasto-Lactacystin beta-lactone, Lactacystin, MG-115, MG-132, Antiserum to NEDD8, PA28 Activator, 20S Proteasome, Polyclonal Antibody to Proteasome 20S alpha-Type 1 Subunit, Polyclonal Antibody to Proteasome 26S Subunit S10B, Polyclonal Antibody to Proteasome 26S Subunit S2, Polyclonal Antibody to Proteasome 26S Subunit S4, Polyclonal Antibody to Proteasome 26S Subunit S5A, Polyclonal Antibody to Proteasome 26S Subunit S6, Polyclonal Antibody to Proteasome 26S Subunit S6', Polyclonal Antibody to Proteasome 26S Subunit S7, Polyclonal antibody to Proteasome 26S Subunit S8, Polyclonal antibody to Proteasome Activator PA28 Alpha, polyclonal antibody to Proteasome Activator PA28 Gamma, Polyclonal antibody to Proteasome Activator PA700 Subunit 10B, 26S Proteasome Fraction, Proteasome Inhibitor I, Proteasome Inhibitor II, Proteasome Substrate I (Fluorogenic), Proteasome Substrate II (Fluorogenic), Proteasome Substrate III (Fluorogenic), Proteasome Substrate IV (Fluorogenic), 5-100 Fraction, SUMO-1/Sentrin-1 (1-101), SUMO-1/Sentrin-1 (1-97), Antiserum to SUMO-1/Sentrin-1, Ubc10, Ubc5b, Ubc5c, Ubc6, Ubc7, Antiserum to Ubc9, Ubc9, UbCH2/E2-14K, UbCH3/Cdc34, UbCH5a, Ubiquitin Activating Enzyme (E1), Ubiquitin Activating Enzyme (E1), Ubiquitin Aldehyde, Ubiquitin Conjugating Enzyme Fractions, Ubiquitin C-terminal Hydrolase, Ubiquitin K48R, Methylated Ubiquitin, GST-Ubiquitin, (His)6 Ubiquitin, Ubiquitin-AMC, Ubiquitin-Sepharose.

In some embodiments, the proteasome inhibitor is a reversible proteasome inhibitor. In some embodiments, the proteasome inhibitor is an irreversible proteasome inhibitor.

In some embodiments, the proteasome inhibitor is selected from the group consisting of bortezomib, delanzomib, ixazomib, carfilzomib, oprozomib, MG132 and marizomib. In some embodiments, the proteasome inhibitor is selected from the group consisting of peptide aldehydes (preferably N-carbobenzyloxy-leucyl-norleucinal (IPSI-OO1)), peptide boronates (preferably bortezomib (PS-341)), peptide epoxyketones (preferably epoxomicin derivative carfilzomib (PR-171)), or salinosporamide A (NPI-0052, i.e., marizomib).

In some embodiments, the proteasome inhibitor is marizomib (MRZ).

In some embodiments, the proteasome inhibitor has an IC50 of the anti-proteasome inhibitory activity of about 10 µM, 7.5 µM, 5 µM, 2.5 µM, 1 µM or less. In some embodiments, the proteasome inhibitor has an IC50 of the anti-proteasome inhibitory activity of about 500 nM, 250 nM, 100 nM, 80 nM, 60 nM, 40 nM, 20 nM, 10 nM or less.

In some embodiments, the proteasome inhibitor is capable of penetrating blood brain barrier (BBB).

C. Alkylating Agent

In some embodiments, the second agent is an alkylating agent. In some embodiments, the alkylating agent is an alkylating antineoplastic agent.

Exemplary alkylating agents include, but are not limited to, cyclophosphamide (Cytoxan), mechlorethamine, chlorambucil, melphalan, carmustine (BCNU), thiotepa, busulfan, alkyl sulphonates, ethylene imines, nitrogen mustard analogs, estramustine sodium phosphate, ifosfamide, nitrosoureas, lomustine, and streptozocin.

In some embodiments, the alkylating agent is a bifunctional alkylator (e.g., cyclophosphamide, mechlorethamine, chlorambucil, melphalan).

In some embodiments, the alkylating agent is a monofunctional alkylator (e.g., dacarbazine (DTIC), nitrosoureas, temozolomide).

Examples of the alkylating agents include temozolomide (TMZ); MeOSO2(CH2)2-lexitropsin (Me-Lex); Cis-diamminedichloroplatinum II (cis-DDP); mitomycin bioreductive alkylating agents; quinones; STZ (streptozotocin); cyclophosphamide; nitrogen mustard family members such as chloroambucil; pentostatin (purine analogs); fludarabine; bendamustine hydrochloride which is the active ingredient of Ribomustin (alkylating group in common with the nitrogen mustard family, also an antimetabolites); chloroethylating nitrosoureas (lomustine, fotemustine, cystemustine); dacarbazine (DTIC); and procarbazine.

In some embodiments, the alkylating agent is temozolomide.

In some embodiments, the alkylating agent is capable of penetrating blood brain barrier.

a) Nitrosourea Compound

In some embodiments, the alkylating agent is a nitrosourea compound. Examples of nitrosourea compounds include arabinopyranosyl-N-methyl-N-nitrosourea (aranose), carmustine (BCNU, BiCNU), chlorozotocin, ethylnitrosourea (ENU), fotemustine, lomustine (CCNU), nimustine, N-Nitroso-N-methylurea (NMU), ranimustine (MCNU), semustine, and streptozocin (Streptozotocin). In some embodiments, the alkylating agent is selected from lomustine, semustine and streptozocin.

In some embodiments, the alkylating agent is lomustine (CCNU).

In some embodiments, the nitrosourea compound (e.g., lomustine) is capable of penetrating blood brain barrier.

D. Anti-Epilepsy Drugs (AEDs)

In some embodiments, the second agent is an anti-epilepsy drug. In some embodiments, the anti-epilepsy drug is selected from the group consisting of acetazolamide (e.g., Diamox SR), carbamazepine (e.g., Carbagen SR), clobazam (e.g., Frisium, Tapclob), clonazepam (e.g., Rivotril), eslicarbazepine acetate (e.g., Zebinix), ethosuximide (e.g., Emeside, Zarotin), gabapentin (e.g., Neurotin), lacosamide (e.g., Vimpat), lamotrigine (e.g., Lamictal), levetiracetam (e.g., Desitrend, Keppra), nitrazepam, oxcarbazepine (e.g., Trileptal), perampanel (e.g., Fycompa), piracetam (e.g., Nootropil), phenobarbital, phenytoin (e.g., Epanutin, Phenotyoin Sodium Flynn), pregabalin (e.g., Lyrica), primidone, rufinamide (e.g., Inovelon), sodium valproate (e.g., Convulex, Epilim, Epilim Chrono, Epilim Chronosphere, Episenta, Epival), stiripentol (e.g., Diacomit), tiagabine (e.g., Gabitril), topiramate (e.g., Topomax), vigabatrin (e.g., Sabril), zonisamide (e.g., Zonegran).

E. VEGFR Inhibitor

In some embodiments, the second agent is a VEGFR inhibitor. In some embodiments, the VEGFR inhibitor is a tyrosine kinase inhibitor. The VEGFR inhibitor of the present application can be small molecules (e.g., less than about 1000 daltons) or large molecules (e.g., polypeptides of greater than about 1000 daltons). Exemplary VEGFR inhibitors include, but not limited to, bevacizumab, pazopanib, sunitinib, axitinib, ponatinib, cabozantinib, lenvatinib, ramucirumab, regorafenib, vandetanib, and ziv-aflibercept.

Method of Treatment Based on Presence of a Biomarker

The present application in one aspect provides methods of treating a CNS disorder in an individual based on the status of one or more mTOR-activating aberrations in one or more mTOR-associated genes. In some embodiments, the one or more biomarkers are indicative of favorable response to treatment with an mTOR inhibitor.

A. mTOR-Activating Aberrations

The present application contemplates mTOR-activating aberrations in any one or more mTOR-associated genes described above, including deviations from the reference sequences (i.e. genetic aberrations), abnormal expression levels and/or abnormal activity levels of the one or more mTOR-associated genes. The present application encompasses treatments and methods based on the status of any one or more of the mTOR-activating aberrations disclosed herein.

The mTOR-activating aberrations described herein are associated with an increased (i.e. hyperactivated) mTOR signaling level or activity level. The mTOR signaling level or mTOR activity level described in the present application may include mTOR signaling in response to any one or any combination of the upstream signals described above, and may include mTOR signaling through mTORC1 and/or mTORC2, which may lead to measurable changes in any one or combinations of downstream molecular, cellular or physiological processes (such as protein synthesis, autophagy, metabolism, cell cycle arrest, apoptosis etc.).

In some embodiments, the mTOR-activating aberration hyperactivates the mTOR activity by at least about any one of 10%, 20%, 30%, 40%, 60%, 70%, 80%, 90%, 100%, 200%, 500% or more above the level of mTOR activity without the mTOR-activating aberration. In some embodiments, the hyperactivated mTOR activity is mediated by mTORC1 only. In some embodiments, the hyperactivated mTOR activity is mediated by mTORC2 only. In some embodiments, the hyperactivated mTOR activity is mediated by both mTORC1 and mTORC2.

Methods of determining mTOR activity are known in the art. See, for example, Brian C G et al., *Cancer Discovery*, 2014, 4:554-563. The mTOR activity may be measured by quantifying any one of the downstream outputs (e.g. at the molecular, cellular, and/or physiological level) of the mTOR signaling pathway as described above. For example, the mTOR activity through mTORC1 may be measured by determining the level of phosphorylated 4EBP1 (e.g. P-S65-4EBP1), and/or the level of phosphorylated S6K1 (e.g. P-T389-S6K1), and/or the level of phosphorylated AKT1 (e.g. P-S473-AKT1). The mTOR activity through mTORC2 may be measured by determining the level of phosphorylated FoxO1 and/or Fox03a. The level of a phosphorylated protein may be determined using any method known in the art, such as Western blot assays using antibodies that specifically recognize the phosphorylated protein of interest.

Candidate mTOR-activating aberrations may be identified through a variety of methods, for example, by literature search or by experimental methods known in the art, including, but not limited to, gene expression profiling experiments (e.g. RNA sequencing or microarray experiments), quantitative proteomics experiments, and gene sequencing experiments. For example, gene expression profiling experiments and quantitative proteomics experiments conducted on a sample collected from an individual having a CNS disorder compared to a control sample may provide a list of genes and gene products (such as RNA, protein, and phosphorylated protein) that are present at aberrant levels. In some instances, gene sequencing (such as exome sequencing) experiments conducted on a sample collected from an individual having a CNS disorder compared to a control sample may provide a list of genetic aberrations. Statistical association studies (such as genome-wide association studies) may be performed on experimental data collected from a population of individuals having a CNS disorder to associate aberrations (such as aberrant levels or genetic aberrations) identified in the experiments with CNS disorder. In some embodiments, targeted sequencing experiments (such as the ONCOPANEL™ test) are conducted to provide a list of genetic aberrations in an individual having a CNS disorder.

The ONCOPANEL™ test can be used to survey exonic DNA sequences of cancer related genes and intronic regions for detection of genetic aberrations, including somatic mutations, copy number variations and structural rearrangements in DNA from various sources of samples (such as a tumor biopsy or blood sample), thereby providing a candidate list of genetic aberrations that may be mTOR-activating aberrations. In some embodiments, the mTOR-associated gene aberration is a genetic aberration or an aberrant level (such as expression level or activity level) in a gene selected from the ONCOPANEL™ test (CLIA certified). See, for example, Wagle N. et al. *Cancer discovery* 2.1 (2012): 82-93.

An exemplary version of ONCOPANEL™ test includes 300 cancer genes and 113 introns across 35 genes. The 300 genes included in the exemplary ONCOPANEL™ test are: ABL1, AKT1, AKT2, AKT3, ALK, ALOX12B, APC, AR, ARAF, ARID1A, ARID1B, ARID2, ASXL1, ATM, ATRX, AURKA, AURKB, AXL, B2M, BAP1, BCL2, BCL2L1, BCL2L12, BCL6, BCOR, BCORL1, BLM, BMPR1A, BRAF, BRCA1, BRCA2, BRD4, BRIP1, BUB1B, CADM2, CARD11, CBL, CBLB, CCND1, CCND2, CCND3, CCNE1, CD274, CD58, CD79B, CDC73, CDH1, CDK1, CDK2, CDK4, CDK5, CDK6, CDK9, CDKN1A, CDKN1B, CDKN1C, CDKN2A, CDKN2B, CDKN2C, CEBPA, CHEK2, CIITA, CREBBP, CRKL, CRLF2, CRTC1, CRTC2, CSF1R, CSF3R, CTNNB1, CUX1, CYLD, DDB2, DDR2, DEPDC5, DICER1, DIS3, DMD, DNMT3A, EED, EGFR, EP300, EPHA3, EPHA5, EPHA7, ERBB2, ERBB3, ERBB4, ERCC2, ERCC3, ERCC4, ERCC5, ESR1, ETV1, ETV4, ETV5, ETV6, EWSR1, EXT1, EXT2, EZH2, FAM46C, FANCA, FANCC, FANCD2, FANCE, FANCF, FANCG, FAS, FBXW7, FGFR1, FGFR2, FGFR3, FGFR4, FH, FKBP9, FLCN, FLT1, FLT3, FLT4, FUS, GATA3, GATA4, GATA6, GLI1, GLI2, GLI3, GNA11, GNAQ, GNAS, GNB2L1, GPC3, GSTM5, H3F3A, HNF1A, HRAS, ID3, IDH1, IDH2, IGF1R, IKZF1, IKZF3, INSIG1, JAK2, JAK3, KCNIP1, KDM5C, KDM6A, KDM6B, KDR, KEAP1, KIT, KRAS, LINC00894, LMO1, LMO2, LMO3, MAP2K1, MAP2K4, MAP3K1, MAPK1, MCL1, MDM2, MDM4, MECOM, MEF2B, MEN1, MET, MITF, MLH1, MLL (KMT2A), MLL2 (KTM2D), MPL, MSH2, MSH6, MTOR, MUTYH, MYB, MYBL1, MYC, MYCL1 (MYCL), MYCN, MYD88, NBN, NEGR1, NF1, NF2, NFE2L2, NFKBIA, NFKBIZ, NKX2-1, NOTCH1, NOTCH2, NPM1, NPRL2, NPRL3, NRAS, NTRK1, NTRK2, NTRK3, PALB2, PARK2, PAX5, PBRM1, PDCD1LG2, PDGFRA, PDGFRB, PHF6, PHOX2B, PIK3C2B, PIK3CA, PIK3R1, PIM1, PMS1, PMS2, PNRC1, PRAME, PRDM1, PRF1, PRKAR1A, PRKCI, PRKCZ, PRKDC, PRPF40B, PRPF8, PSMD13, PTCH1, PTEN, PTK2, PTPN11, PTPRD, QKI, RAD21, RAF1, RARA, RB1, RBL2, RECQL4, REL, RET, RFWD2, RHEB, RHPN2, ROS1, RPL26, RUNX1, SBDS, SDHA, SDHAF2, SDHB, SDHC, SDHD, SETBP1, SETD2, SF1, SF3B1, SH2B3, SLITRK6, SMAD2, SMAD4, SMARCA4, SMARCB1, SMC1A, SMC3, SMO, SOCS1, SOX2, SOX9, SQSTM1, SRC, SRSF2, STAG1, STAG2, STAT3, STAT6, STK11, SUFU, SUZ12, SYK, TCF3, TCF7L1, TCF7L2, TERC, TERT, TET2, TLR4, TNFAIP3, TP53, TSC1, TSC2, U2AF1, VHL, WRN, WT1, XPA, XPC, XPO1, ZNF217, ZNF708, ZRSR2. The intronic regions surveyed in the exemplary ONCOPANEL™ test are tiled on specific introns of ABL1, AKT3, ALK, BCL2, BCL6, BRAF, CIITA, EGFR, ERG, ETV1, EWSR1, FGFR1, FGFR2, FGFR3, FUS, IGH, IGL, JAK2, MLL, MYC, NPM1, NTRK1, PAX5, PDGFRA, PDGFRB, PPARG, RAF1, RARA, RET, ROS1, SS18, TRA, TRB, TRG, TMPRSS2. mTOR-activating aberrations (such as genetic aberration and aberrant levels) of any of the genes included in any embodiment or version of the ONCOPANEL™ test, including, but not limited to the genes and intronic regions listed above, are contemplated by the present application to serve as a basis for selecting an individual for treatment with the mTOR inhibitor nanoparticle compositions.

Whether a candidate genetic aberration or aberrant level is an mTOR-activating aberration can be determined with methods known in the art. Genetic experiments in cells (such as cell lines) or animal models may be performed to ascertain that the CNS disorder-associated aberrations identified from all aberrations observed in the experiments are mTOR-activating aberrations. For example, a genetic aberration may be cloned and engineered in a cell line or animal model, and the mTOR activity of the engineered cell line or animal model may be measured and compared with corresponding cell line or animal model that do not have the genetic aberration. An increase in the mTOR activity in such experiment may indicate that the genetic aberration is a candidate mTOR-activating aberration, which may be tested in a clinical study.

B. Genetic Aberrations

Genetic aberrations of one or more mTOR-associated genes may comprise a change to the nucleic acid (such as DNA and RNA) or protein sequence (i.e. mutation) or an epigenetic feature associated with an mTOR-associated gene, including, but not limited to, coding, non-coding, regulatory, enhancer, silencer, promoter, intron, exon, and untranslated regions of the mTOR-associated gene.

The genetic aberration may be a germline mutation (including chromosomal rearrangement), or a somatic mutation (including chromosomal rearrangement). In some embodiments, the genetic aberration is present in all tissues, including normal tissue and the tissue associated with the CNS disorder, of the individual. In some embodiments, the genetic aberration is present only in the tissue associated with the CNS disorder. In some embodiments, the genetic aberration is present only in a fraction of the tissue associated with the CNS disorder.

In some embodiments, the mTOR-activating aberration comprises a mutation of an mTOR-associated gene, including, but not limited to, deletion, frameshift, insertion, indel, missense mutation, nonsense mutation, point mutation, single nucleotide variation (SNV), silent mutation, splice site mutation, splice variant, and translocation. In some embodiments, the mutation may be a loss of function mutation for a negative regulator of the mTOR signaling pathway or a gain of function mutation of a positive regulator of the mTOR signaling pathway.

In some embodiments, the genetic aberration comprises a copy number variation of an mTOR-associated gene. Normally, there are two copies of each mTOR-associated gene per genome. In some embodiments, the copy number of the mTOR-associated gene is amplified by the genetic aberration, resulting in at least about any of 3, 4, 5, 6, 7, 8, or more copies of the mTOR-associated gene in the genome. In some embodiments, the genetic aberration of the mTOR-associated gene results in loss of one or both copies of the mTOR-associated gene in the genome. In some embodiments, the copy number variation of the mTOR-associated gene is loss of heterozygosity of the mTOR-associated gene. In some embodiments, the copy number variation of the mTOR-associated gene is deletion of the mTOR-associated gene. In some embodiments, the copy number variation of the mTOR-associated gene is caused by structural rearrangement of the genome, including deletions, duplications, inversion, and translocation of a chromosome or a fragment thereof.

In some embodiments, the genetic aberration comprises an aberrant epigenetic feature associated with an mTOR-associated gene, including, but not limited to, DNA methylation, hydroxymethylation, aberrant histone binding, chromatin remodeling, and the like. In some embodiments, the promotor of the mTOR-associated gene is hypermethylated in the individual, for example by at least about any of 10%, 20%, 30%, 40%, 50%, 60%, 70%, 80%, 90%, or more compared to a control level (such as a clinically accepted normal level in a standardized test).

In some embodiments, the mTOR-activating aberration is a genetic aberration (such as a mutation or a copy number variation) in any one of the mTOR-associated genes described above. In some embodiments, the mTOR-activating aberration is a mutation or a copy number variation in one or more genes selected from AKT1, MTOR, PIK3CA, PIK3CG, TSC1, TSC2, RHEB, STK11, NF1, NF2, PTEN, TP53, FGFR4, and BAP1. In some embodiments, the mTOR-activating aberration is a mutation or a copy number variation in PTEN. In some embodiments, the mTOR-activating aberration is a mutation or a copy number variation in TSC1. In some embodiments, the mTOR-activating aberration is a mutation or a copy number variation in TSC2.

Genetic aberrations in mTOR-associated genes have been identified in various human cancers, including hereditary cancers and sporadic cancers. For example, germline inactivating mutations in TSC1/2 cause tuberous sclerosis, and patients with this condition are present with lesions that include skin and brain hamartomas, renal angiomyolipomas, and renal cell carcinoma (RCC) (Krymskaya V P et al. 2011 FASEB Journal 25(6): 1922-1933). PTEN hamartoma tumor syndrome (PHTS) is linked to inactivating germline PTEN mutations and is associated with a spectrum of clinical manifestations, including breast cancer, endometrial cancer, follicular thyroid cancer, hamartomas, and RCC (Legendre C. et al. 2003 Transplantation proceedings 35(3 Suppl): 1515-1535). In addition, sporadic kidney cancer has also been shown to harbor somatic mutations in several genes in the PI3K-Akt-mTOR pathway (e.g. AKT1, MTOR, PIK3CA, PTEN, RHEB, TSC1, TSC2) (Power L A, 1990 *Am. J. Hosp. Pharm.* 475.5: 1033-1049; Badesch D B et al. 2010 Chest 137(2): 376-3871; Kim J C & Steinberg G D, 2001, *The Journal of urology*, 165(3): 745-756; McKiernan J. et al. 2010, *J. Urol.* 183(Suppl 4)). Of the top 50 significantly mutated genes identified by the Cancer Genome Atlas in clear cell renal cell carcinoma, the mutation rate is about 17% for gene mutations that converge on mTORC1 activation (Cancer Genome Atlas Research Network. "Comprehensive molecular characterization of clear cell renal cell carcinoma." 2013 *Nature* 499: 43-49). Genetic aberrations in mTOR-associated genes have been found to confer sensitivity in individuals having cancer to treatment with a limus drug. See, for example, Wagle et al., *N. Eng. J. Med.* 2014, 371:1426-33; Iyer et al., *Science* 2012, 338: 221; Wagle et al. *Cancer Discovery* 2014, 4:546-553; Grabiner et al., *Cancer Discovery* 2014, 4:554-563; Dickson et al. *Int J. Cancer* 2013, 132(7): 1711-1717, and Lim et al, *J Clin. Oncol.* 33, 2015 suppl; abstr 11010. Genetic aberrations of mTOR-associated genes described by the above references are incorporated herein. Exemplary genetic aberrations in some mTOR-associated genes are described below, and it is understood that the present application is not limited to the exemplary genetic aberrations described herein.

In some embodiments, the mTOR-activating aberration comprises a genetic aberration in MTOR. In some embodiments, the genetic aberration comprises an activating mutation of MTOR. In some embodiments, the activating mutation of MTOR is at one or more positions (such as about any one of 1, 2, 3, 4, 5, 6, or more positions) in the protein sequence of MTOR selected from the group consisting of N269, L1357, N1421, L1433, A1459, L1460, C1483, E1519, K1771, E1799, F1888, I1973, T1977, V2006, E2014, I2017, N2206, L2209, A2210, S2215, L2216, R2217, L2220, Q2223, A2226, E2419, L2431, I2500, R2505, and D2512. In some embodiments, the activating mutation of MTOR is one or more missense mutations (such as about any one of 1, 2, 3, 4, 5, 6, or more mutations) selected from the group consisting of N269S, L1357F, N1421D, L1433S, A1459P, L1460P, C1483F, C1483R, C1483W, C1483Y, E1519T, K1771R, E1799K, F1888I, F1888I L, I1973F, T1977R, T1977K, V2006I, E2014K, I2017T, N2206S, L2209V, A2210P, S2215Y, S2215F, S2215P, L2216P, R2217W, L2220F, Q2223K, A2226S, E2419K, L2431P, I2500M, R2505P, and D2512H. In some embodiments, the activating mutation of MTOR disrupts binding of MTOR with RHEB. In some embodiments, the activating mutation of MTOR disrupts binding of MTOR with DEPTOR.

In some embodiments, the mTOR-activating aberration comprises a genetic aberration in TSC1 or TSC2. In some embodiments, the genetic aberration comprises a loss of heterozygosity of TSC1 or TSC2. In some embodiments, the genetic aberration comprises a loss of function mutation in TSC1 or TSC2. In some embodiments, the loss of function mutation is a frameshift mutation or a nonsense mutation in TSC1 or TSC2. In some embodiments, the loss of function mutation is a frameshift mutation c.1907_1908del in TSC1. In some embodiments, the loss of function mutation is a splice variant of TSC1: c.1019+1G>A. In some embodiments, the loss of function mutation is the nonsense mutation c.1073G>A in TSC2, and/or p.Trp103* in TSC1. In some embodiments, the loss of function mutation comprises a missense mutation in TSC1 or in TSC2. In some embodiments, the missense mutation is in position A256 of TSC1, and/or position Y719 of TSC2. In some embodiments, the missense mutation comprises A256V in TSC1 or Y719H in TSC2.

In some embodiments, the mTOR-activating aberration comprises a genetic aberration in RHEB. In some embodiments, the genetic aberration comprises a loss of function mutation in RHEB. In some embodiments, the loss of function mutation is at one or more positions in the protein sequence of RHEB selected from Y35 and E139. In some embodiments, the loss of function mutation in RHEB is selected from Y35N, Y35C, Y35H and E139K.

In some embodiments, the mTOR-activating aberration comprises a genetic aberration in NF1. In some embodiments, the genetic aberration comprises a loss of function mutation in NF1. In some embodiments, the loss of function mutation in NF1 is a missense mutation at position D1644 in NF1. In some embodiments, the missense mutation is D1644A in NF1.

In some embodiments, the mTOR-activating aberration comprises a genetic aberration in NF2. In some embodiments, the genetic aberration comprises a loss of function mutation in NF2. In some embodiments, the loss of function mutation in NF2 is a nonsense mutation. In some embodiments, the nonsense mutation in NF2 is c.863C>G.

In some embodiments, the mTOR-activating aberration comprises a genetic aberration in PTEN. In some embodiments, the genetic aberration comprises a deletion of PTEN in the genome. In some embodiments, the genetic aberration comprises a loss of function mutation in PTEN. In some embodiments, the loss of function mutation comprises a missense mutation, a nonsense mutation or a frameshift mutation. In some embodiments, the mutation comprises at a position in PTEN selected from the group consisting of K125E, K125X, E150Q, D153Y D153N K62R, Y65C, V217A, and N323K. In some embodiments, the genetic aberration comprises a loss of heterozygosity (LOH) at the PTEN locus.

In some embodiments, the mTOR-activating aberration comprises a genetic aberration in PI3K. In some embodiments, the genetic aberration comprises a loss of function mutation in PIK3CA or PIK3CG. In some embodiments, the loss of function mutation comprises a missense mutation at a position in PIK3CA selected from the group consisting of E542, 1844, and H1047. In some embodiments, the loss of function mutation comprises a missense in PIK3CA selected from the group consisting of E542K, 1844V, and H1047R.

In some embodiments, the mTOR-activating aberration comprises a genetic aberration in AKT1. In some embodiments, the genetic aberration comprises an activating mutation in AKT1. In some embodiments, the activating mutation is a missense mutation in position H238 in AKT1. In some embodiments, the missense mutation is H238Y in AKT1.

In some embodiments, the mTOR-activating aberration comprises a genetic aberration in TP53. In some embodiments, the genetic aberration comprises a loss of function mutation in TP53. In some embodiments, the loss of function mutation is a frameshift mutation in TP53, such as A39fs*5.

The genetic aberrations of the mTOR-associated genes may be assessed based on a sample, such as a sample from the individual and/or reference sample. In some embodiments, the sample is a tissue sample or nucleic acids extracted from a tissue sample. In some embodiments, the sample is a cell sample (for example a CTC sample) or nucleic acids extracted from a cell sample. In some embodiments, the sample is a tumor biopsy. In some embodiments, the sample is a tumor sample or nucleic acids extracted from a tumor sample.

In some embodiments, the sample is a biopsy sample or nucleic acids extracted from the biopsy sample. In some embodiments, the sample is a Formaldehyde Fixed-Paraffin Embedded (FFPE) sample or nucleic acids extracted from the FFPE sample. In some embodiments, the sample is a blood sample. In some embodiments, cell-free DNA is isolated from the blood sample. In some embodiments, the biological sample is a plasma sample or nucleic acids extracted from the plasma sample.

The genetic aberrations of the mTOR-associated gene may be determined by any method known in the art. See, for example, Dickson et al. *Int. J. Cancer,* 2013, 132(7): 1711-1717; Wagle N. *Cancer Discovery,* 2014, 4:546-553; and Cancer Genome Atlas Research Network. *Nature* 2013, 499: 43-49. Exemplary methods include, but are not limited to, genomic DNA sequencing, bisulfite sequencing or other DNA sequencing-based methods using Sanger sequencing or next generation sequencing platforms; polymerase chain reaction assays; in situ hybridization assays; and DNA microarrays. The epigenetic features (such as DNA methylation, histone binding, or chromatin modifications) of one or more mTOR-associated genes from a sample isolated from the individual may be compared with the epigenetic features of the one or more mTOR-associated genes from a control sample. The nucleic acid molecules extracted from the sample can be sequenced or analyzed for the presence of the mTOR-activating genetic aberrations relative to a reference sequence, such as the wildtype sequences of AKT1, FLT-3, MTOR, PIK3CA, PIK3CG, TSC1, TSC2, RHEB, STK11, NF1, NF2, TP53, FGFR4, BAP1, KRAS, NRAS and PTEN.

In some embodiments, the genetic aberration of an mTOR-associated gene is assessed using cell-free DNA sequencing methods. In some embodiments, the genetic aberration of an mTOR-associated gene is assessed using next-generation sequencing. In some embodiments, the genetic aberration of an mTOR-associated gene isolated from a blood sample is assessed using next-generation sequencing. In some embodiments, the genetic aberration of an mTOR-associated gene is assessed using exome sequencing. In some embodiments, the genetic aberration of an mTOR-associated gene is assessed using fluorescence in-situ hybridization analysis. In some embodiments, the genetic aberration of an mTOR-associated gene is assessed prior to initiation of the methods of treatment described herein. In some embodiments, the genetic aberration of an mTOR-associated gene is assessed after initiation of the methods of treatment described herein. In some embodiments, the genetic aberration of an mTOR-associated gene is assessed prior to and after initiation of the methods of treatment described herein.

C. Aberrant levels

An aberrant level of an mTOR-associated gene may refer to an aberrant expression level or an aberrant activity level.

Aberrant expression level of an mTOR-associated gene comprises an increase or decrease in the level of a molecule encoded by the mTOR-associated gene compared to the control level. The molecule encoded by the mTOR-associated gene may include RNA transcript(s) (such as mRNA), protein isoform(s), phosphorylated and/or dephosphorylated states of the protein isoform(s), ubiquitinated and/or de-ubiquitinated states of the protein isoform(s), membrane localized (e.g. myristoylated, palmitoylated, and the like) states of the protein isoform(s), other post-translationally modified states of the protein isoform(s), or any combination thereof.

Aberrant activity level of an mTOR-associated gene comprises enhancement or repression of a molecule encoded by any downstream target gene of the mTOR-associated gene, including epigenetic regulation, transcriptional regulation, translational regulation, post-translational regulation, or any combination thereof of the downstream target gene. Additionally, activity of an mTOR-associated gene comprises downstream cellular and/or physiological effects in response to the mTOR-activating aberration, including, but not limited to, protein synthesis, cell growth, proliferation, signal transduction, mitochondria metabolism, mitochondria biogenesis, stress response, cell cycle arrest, autophagy, microtubule organization, and lipid metabolism.

In some embodiments, the mTOR-activating aberration (e.g. aberrant expression level) comprises an aberrant protein phosphorylation level. In some embodiments, the aberrant phosphorylation level is in a protein encoded by an mTOR-associated gene selected from the group consisting of AKT, TSC2, mTOR, PRAS40, S6K, S6, and 4EBP1. Exemplary phosphorylated species of mTOR-associated genes that may serve as relevant biomarkers include, but are not limited to, AKT S473 phosphorylation, PRAS40 T246 phosphorylation, mTOR S2448 phosphorylation, 4EBP1 T36 phosphorylation, S6K T389 phosphorylation, 4EBP1 T70 phosphorylation, and S6 S235 phosphorylation. In some embodiments, the individual is selected for treatment if the protein in the individual is phosphorylated. In some embodiments, the individual is selected for treatment if the protein in the individual is not phosphorylated. In some embodiments, the phosphorylation status of the protein is determined by immunohistochemistry.

The levels (such as expression levels and/or activity levels) of an mTOR-associated gene in an individual may be determined based on a sample (e.g., sample from the individual or reference sample). In some embodiments, the sample is from a tissue, organ, cell, or tumor. In some embodiments, the sample is a biological sample. In some embodiments, the biological sample is a biological fluid sample or a biological tissue sample. In further embodiments, the biological fluid sample is a bodily fluid. In some embodiments, the sample is a tissue associated with the CNS disorder, normal tissue adjacent to said tissue associated with the CNS disorder, normal tissue distal to said tissue associated with the CNS disorder, blood sample, or other biological sample. In some embodiments, the sample is a fixed sample. Fixed samples include, but are not limited to, a formalin fixed sample, a paraffin-embedded sample, or a frozen sample. In some embodiments, the sample is a biopsy containing cells from the CNS disorder tissue. In a further embodiment, the biopsy is a fine needle aspiration of cells from the tissue associated with the CNS disorder. In some embodiments, the biopsied cells are centrifuged into a pellet, fixed, and embedded in paraffin. In some embodiments, the biopsied cells are flash frozen. In some embodiments, the biopsied cells are mixed with an antibody that recognizes a molecule encoded by the mTOR-associated gene. In some embodiments, the at least one mTOR-associated gene comprises enhancement or repression of a molecule encoded by any downstream target gene of the mTOR-associated gene, including epigenetic regulation, transcriptional regulation, translational regulation, post-translational regulation, or any combination thereof of the downstream target gene. Additionally, activity of an mTOR-associated gene comprises downstream cellular and/or physiological effects in response to the mTOR-activating aberration, including, but not limited to, protein synthesis, cell growth, proliferation, signal transduction, mitochondria metabolism, mitochondria biogenesis, stress response, cell cycle arrest, autophagy, microtubule organization, and lipid metabolism.

In some embodiments, the mTOR-activating aberration (e.g. aberrant expression level) comprises an aberrant protein phosphorylation level. In some embodiments, the aberrant phosphorylation level is in a protein encoded by an mTOR-associated gene selected from the group consisting of AKT, TSC2, mTOR, PRAS40, S6K, S6, and 4EBP1. Exemplary phosphorylated species of mTOR-associated genes that may serve as relevant biomarkers include, but are not limited to, AKT S473 phosphorylation, PRAS40 T246 phosphorylation, mTOR S2448 phosphorylation, 4EBP1 T36 phosphorylation, S6K T389 phosphorylation, 4EBP1 T70 phosphorylation, and S6 S235 phosphorylation. In some embodiments, the individual is selected for treatment if the protein in the individual is phosphorylated. In some embodiments, the individual is selected for treatment if the protein in the individual is not phosphorylated. In some embodiments, the phosphorylation status of the protein is determined by immunohistochemistry.

Aberrant levels of mTOR-associates genes have been associated with cancer. For example, high levels (74%) of phosphorylated mTOR expression were found in human bladder cancer tissue array, and phosphorylated mTOR intensity was associated with reduced survival (Hansel D E et al, (2010) *Am. J. Pathol.* 176: 3062-3072). mTOR expression was shown to increase as a function of the disease stage in progression from superficial disease to invasive bladder cancer, as evident by activation of pS6-kinase, which was activated in 54 of 70 cases (77%) of T2 muscle-invasive bladder tumors (Seager C M et al, (2009) *Cancer Prev. Res. (Phila)* 2, 1008-1014). The mTOR signaling pathway is also known to be hyperactivated in pulmonary arterial hypertension.

The levels (such as expression levels and/or activity levels) of an mTOR-associated gene in an individual may be determined based on a sample (e.g., sample from the individual or reference sample). In some embodiments, the sample is from a tissue, organ, cell, or tumor. In some embodiments, the sample is a biological sample. In some embodiments, the biological sample is a biological fluid sample or a biological tissue sample. In further embodiments, the biological fluid sample is a bodily fluid. In some embodiments, the sample is a tissue associated with the CNS disorder, normal tissue adjacent to said tissue associated with the CNS disorder, normal tissue distal to said tissue associated with the CNS disorder, blood sample, or other biological sample. In some embodiments, the sample is a fixed sample. Fixed samples include, but are not limited to, a formalin fixed sample, a paraffin-embedded sample, or a frozen sample. In some embodiments, the sample is a biopsy containing cells from tissue associated with the CNS disorder. In a further embodiment, the biopsy is a fine needle aspiration of cells from tissue associated with the CNS disorder. In some embodiments, the biopsied cells are centrifuged into a pellet, fixed, and embedded in paraffin. In some embodiments, the biopsied cells are flash frozen. In some embodiments, the biopsied cells are mixed with an antibody that recognizes a molecule encoded by the mTOR-associated biomarker comprises an aberrant phosphorylation level of the protein encoded by the mTOR-associated gene comprises enhancement or repression of a molecule encoded by any downstream target gene of the mTOR-associated gene, including epigenetic regulation, transcriptional regulation, translational regulation, post-translational regulation, or any combination thereof of the downstream target gene. Additionally, activity of an mTOR-associated gene comprises downstream cellular and/or physiological effects in response to the mTOR-activating aberration, including, but not limited to, protein synthesis, cell growth, proliferation, signal transduction, mitochondria metabolism, mitochondria biogenesis, stress response, cell cycle arrest, autophagy, microtubule organization, and lipid metabolism.

In some embodiments, the mTOR-activating aberration (e.g. aberrant expression level) comprises an aberrant protein phosphorylation level. In some embodiments, the aberrant phosphorylation level is in a protein encoded by an mTOR-associated gene selected from the group consisting of PTEN, AKT, TSC2, mTOR, PRAS40, S6K, S6, and 4EBP1.

Exemplary phosphorylated species of mTOR-associated genes that may serve as relevant biomarkers include, but are not limited to, PTEN Thr366, Ser370, Ser380, Thr382, Thr383, and/or Ser385 phosphorylation, AKT S473 phosphorylation, PRAS40 T246 phosphorylation, mTOR S2448 phosphorylation, 4EBP1 T36 phosphorylation, S6K T389 phosphorylation, 4EBP1 T70 phosphorylation, and S6 S235 phosphorylation. In some embodiments, the individual is selected for treatment if the protein in the individual is phosphorylated. In some embodiments, the individual is selected for treatment if the protein in the individual is not phosphorylated. In some embodiments, the phosphorylation status of the protein is determined by immunohistochemistry.

Aberrant levels of mTOR-associates genes have been associated with cancer. For example, high levels (74%) of phosphorylated mTOR expression were found in human bladder cancer tissue array, and phosphorylated mTOR intensity was associated with reduced survival (Hansel D E et al, (2010) *Am. J. Pathol.* 176: 3062-3072). mTOR expression was shown to increase as a function of the disease stage in progression from superficial disease to invasive bladder cancer, as evident by activation of pS6-kinase, which was activated in 54 of 70 cases (77%) of T2 muscle-invasive bladder tumors (Seager C M et al, (2009) *Cancer Prev. Res. (Phila)* 2, 1008-1014). The mTOR signaling pathway is also known to be hyperactivated in pulmonary arterial hypertension.

The levels (such as expression levels and/or activity levels) of an mTOR-associated gene in an individual may be determined based on a sample (e.g., sample from the individual or reference sample). In some embodiments, the sample is from a tissue, organ, cell, or tumor. In some embodiments, the sample is a biological sample. In some embodiments, the biological sample is a biological fluid sample or a biological tissue sample. In further embodiments, the biological fluid sample is a bodily fluid. In some embodiments, the sample is a tissue associated with a CNS disorder, normal tissue adjacent to said tissue associated with the CNS disorder, normal tissue distal to said tissue associated with the CNS disorder, blood sample, or other biological sample. In some embodiments, the sample is a fixed sample. Fixed samples include, but are not limited to, a formalin fixed sample, a paraffin-embedded sample, or a frozen sample. In some embodiments, the sample is a biopsy containing cells from tissue associated with the CNS disorder. In a further embodiment, the biopsy is a fine needle aspiration of cells associated with the CNS disorder. In some embodiments, the biopsied cells are centrifuged into a pellet, fixed, and embedded in paraffin. In some embodiments, the biopsied cells are flash frozen. In some embodiments, the biopsied cells are mixed with an antibody that recognizes a molecule encoded by the mTOR-associated gene. In some embodiments, a biopsy is taken to determine whether an individual has a CNS disorder and is then used as a sample. In some embodiments, the sample comprises surgically obtained cells from tissue associated with the CNS disorder. In some embodiments, samples may be obtained at different times than when the determining of expression levels of mTOR-associated gene occurs.

In some embodiments, the sample comprises a circulating metastatic cancer cell. In some embodiments, the sample is obtained by sorting circulating tumor cells (CTCs) from blood. In a further embodiment, the CTCs have detached from a primary tumor and circulate in a bodily fluid. In yet a further embodiment, the CTCs have detached from a primary tumor and circulate in the bloodstream. In a further embodiment, the CTCs are an indication of metastasis.

In some embodiments, the level of a protein encoded by an mTOR-associated gene is determined to assess the aberrant expression level of the mTOR-associated gene. In some embodiments, the level of a protein encoded by a downstream target gene of an mTOR-associated gene is determined to assess the aberrant activity level of the mTOR-associated gene. In some embodiments, protein level is determined using one or more antibodies specific for one or more epitopes of the individual protein or proteolytic fragments thereof. Detection methodologies suitable for use in the practice of the application include, but are not limited to, immunohistochemistry, enzyme linked immunosorbent assays (ELISAs), Western blotting, mass spectroscopy, and immuno-PCR. In some embodiments, levels of protein(s) encoded by the mTOR-associated gene and/or downstream target gene(s) thereof in a sample are normalized (such as divided) by the level of a housekeeping protein (such as glyceraldehyde 3-phosphate dehydrogenase, or GAPDH) in the same sample.

In some embodiments, the level of an mRNA encoded by an mTOR-associated gene is determined to assess the aberrant expression level of the mTOR-associated gene. In some embodiments, the level of an mRNA encoded by a downstream target gene of an mTOR-associated gene is determined to assess the aberrant activity level of the mTOR-associated gene. In some embodiments, a reverse-transcription (RT) polymerase chain reaction (PCR) assay (including a quantitative RT-PCR assay) is used to determine the mRNA levels. In some embodiments, a gene chip or next-generation sequencing methods (such as RNA (cDNA) sequencing or exome sequencing) are used to determine the levels of RNA (such as mRNA) encoded by the mTOR-associated gene and/or downstream target genes thereof. In some embodiments, an mRNA level of the mTOR-associated gene and/or downstream target genes thereof in a sample are normalized (such as divided) by the mRNA level of a housekeeping gene (such as GAPDH) in the same sample.

The levels of an mTOR-associated gene may be a high level or a low level as compared to a control or reference. In some embodiments, wherein the mTOR-associated gene is a positive regulator of the mTOR activity (such as mTORC1 and/or mTORC2 activity), the aberrant level of the mTOR associated gene is a high level compared to the control. In some embodiments, wherein the mTOR-associated gene is a negative regulator of the mTOR activity (such as mTORC1 and/or mTORC2 activity), the aberrant level of the mTOR associated gene is a low level compared to the control.

In some embodiments, the level of the mTOR-associated gene in an individual is compared to the level of the mTOR-associated gene in a control sample. In some embodiments, the level of the mTOR-associated gene in an individual is compared to the level of the mTOR-associated gene in multiple control samples. In some embodiments, multiple control samples are used to generate a statistic that is used to classify the level of the mTOR-associated gene in an individual with a CNS disorder.

The classification or ranking of the level (i.e., high or low) of the mTOR-associated gene may be determined relative to a statistical distribution of control levels. In some embodiments, the classification or ranking is relative to a control sample, such as a normal tissue (e.g. peripheral blood mononuclear cells), or a normal epithelial cell sample (e.g. a buccal swap or a skin punch) obtained from the individual. In some embodiments, the level of the mTOR-associated gene is classified or ranked relative to a statistical distribution of control levels. In some embodiments, the level of the mTOR-associated gene is classified or ranked relative to the level from a control sample obtained from the individual.

Control samples can be obtained using the same sources and methods as non-control samples. In some embodiments, the control sample is obtained from a different individual (for example an individual not having the CNS disorder; an individual having a benign or less advanced form of a disease corresponding to the CNS disorder; and/or an individual sharing similar ethnic, age, and gender). In some embodiments when the sample is a tumor tissue sample, the control sample may be a non-cancerous sample from the same individual. In some embodiments, multiple control samples (for example from different individuals) are used to determine a range of levels of the mTOR-associated genes in a particular tissue, organ, or cell population.

In some embodiments, the control sample is a cultured tissue or cell that has been determined to be a proper control. In some embodiments, the control is a cell that does not have the mTOR-activating aberration. In some embodiments, a clinically accepted normal level in a standardized test is used as a control level for determining the aberrant level of the mTOR-associated gene. In some embodiments, the level of the mTOR-associated gene or downstream target genes thereof in the individual is classified as high, medium or low according to a scoring system, such as an immunohistochemistry-based scoring system.

In some embodiments, the level of the mTOR-associated gene is determined by measuring the level of the mTOR-associated gene in an individual and comparing to a control or reference (e.g., the median level for the given patient population or level of a second individual). For example, if the level of the mTOR-associated gene for the single individual is determined to be above the median level of the patient population, that individual is determined to have high expression level of the mTOR-associated gene. Alternatively, if the level of the mTOR-associated gene for the single individual is determined to be below the median level of the patient population, that individual is determined to have low expression level of the mTOR-associated gene. In some embodiments, the individual is compared to a second individual and/or a patient population which is responsive to the treatment. In some embodiments, the individual is compared to a second individual and/or a patient population which is not responsive to the treatment. In some embodiments, the levels are determined by measuring the level of a nucleic acid encoded by the mTOR-associated gene and/or a downstream target gene thereof. For example, if the level of a molecule (such as an mRNA or a protein) encoded by the mTOR-associated gene for the single individual is determined to be above the median level of the patient population, that individual is determined to have a high level of the molecule (such as mRNA or protein) encoded by the mTOR-associated gene.

Alternatively, if the level of a molecule (such as an mRNA or a protein) encoded by the mTOR-associated gene for the single individual is determined to be below the median level of the patient population, that individual is determined to have a low level of the molecule (such as mRNA or protein) encoded by the mTOR-associated gene.

In some embodiments, the control level of an mTOR-associated gene is determined by obtaining a statistical distribution of the levels of mTOR-associated gene. In some embodiments, the level of the mTOR-associated gene is classified or ranked relative to control levels or a statistical distribution of control levels.

In some embodiments, bioinformatics methods are used for the determination and classification of the levels of the mTOR-associated gene, including the levels of downstream target genes of the mTOR-associated gene as a measure of the activity level of the mTOR-associated gene. Numerous bioinformatics approaches have been developed to assess gene set expression profiles using gene expression profiling data. Methods include but are not limited to those described in Segal, E. et al. Nat. Genet. 34:66-176 (2003); Segal, E. et al. Nat. Genet. 36:1090-1098 (2004); Barry, W. T. et al. Bioinformatics 21:1943-1949 (2005); Tian, L. et al. Proc Nat'l Acad Sci USA 102:13544-13549 (2005); Novak B A and Jain A N. Bioinformatics 22:233-41 (2006); Maglietta R et al. Bioinformatics 23:2063-72 (2007); Bussemaker H J, BMC Bioinformatics 8 Suppl 6:S6 (2007).

In some embodiments, the control level is a pre-determined threshold level. In some embodiments, mRNA level is determined, and a low level is an mRNA level less than about any of 1, 0.9, 0.8, 0.7, 0.6, 0.5, 0.4, 0.3, 0.2, 0.1, 0.05, 0.02, 0.01, 0.005, 0.002, 0.001 or less time that of what is considered as clinically normal or of the level obtained from a control. In some embodiments, a high level is an mRNA level more than about 1.1, 1.2, 1.3, 1.5, 1.7, 2, 2.2, 2.5, 2.7, 3, 5, 7, 10, 20, 50, 70, 100, 200, 500, 1000 times or more than 1000 times that of what is considered as clinically normal or of the level obtained from a control.

In some embodiments, protein expression level is determined, for example by Western blot or an enzyme-linked immunosorbent assay (ELISA). For example, the criteria for low or high levels can be made based on the total intensity of a band on a protein gel corresponding to the protein encoded by the mTOR-associated gene that is blotted by an antibody that specifically recognizes the protein encoded by the mTOR-associated gene, and normalized (such as divided) by a band on the same protein gel of the same sample corresponding to a housekeeping protein (such as GAPDH) that is blotted by an antibody that specifically recognizes the housekeeping protein (such as GAPDH). In some embodiments, the protein level is low if the protein level is less than about any of 1, 0.9, 0.8, 0.7, 0.6, 0.5, 0.4, 0.3, 0.2, 0.1, 0.05, 0.02, 0.01, 0.005, 0.002, 0.001 or less time of what is considered as clinically normal or of the level obtained from a control. In some embodiments, the protein level is high if the protein level is more than about any of 1.1, 1.2, 1.3, 1.5, 1.7, 2, 2.2, 2.5, 2.7, 3, 5, 7, 10, 20, 50, or 100 times or more than 100 times of what is considered as clinically normal or of the level obtained from a control.

In some embodiments, protein expression level is determined, for example by immunohistochemistry. For example, the criteria for low or high levels can be made based on the number of positive staining cells and/or the intensity of the staining, for example by using an antibody that specifically recognizes the protein encoded by the mTOR-associated gene.

In some embodiments, the level is low if less than about 1%, 5%, 10%, 15%, 20%, 25%, 30%, 35%, 40%, 45%, or 50% cells have positive staining. In some embodiments, the level is low if the staining is 1%, 5%, 10%, 15%, 20%, 25%, 30%, 35%, 40%, 45%, or 50% less intense than a positive control staining. In some embodiments, the level is high if more than about 40%, 45%, 50%, 55%, 60%, 65%, 70%, 75%, 80%, 85%, or 90%, cells have positive staining. In some embodiments, the level is high if the staining is as intense as positive control staining. In some embodiments, the level is high if the staining is 80%, 85%, or 90% as intense as positive control staining.

In some embodiments, the scoring is based on an "H-score" as described in US Pat. Pub. No. 2013/0005678. An H-score is obtained by the formula: 3× percentage of strongly staining cells+2× percentage of moderately staining cells+percentage of weakly staining cells, giving a range of 0 to 300.

In some embodiments, strong staining, moderate staining, and weak staining are calibrated levels of staining, wherein a range is established and the intensity of staining is binned within the range. In some embodiments, strong staining is staining above the $75^{th}$ percentile of the intensity range, moderate staining is staining from the $25^{th}$ to the $75^{th}$ percentile of the intensity range, and low staining is staining is staining below the $25^{th}$ percentile of the intensity range. In some aspects one skilled in the art, and familiar with a particular staining technique, adjusts the bin size and defines the staining categories.

In some embodiments, the label high staining is assigned where greater than 50% of the cells stained exhibited strong reactivity, the label no staining is assigned where no staining was observed in less than 50% of the cells stained, and the label low staining is assigned for all of other cases.

In some embodiments, the assessment and/or scoring of the genetic aberration or the level of the mTOR-associated gene in a sample, patient, etc., is performed by one or more experienced clinicians, i.e., those who are experienced with the mTOR-associated gene expression and the mTOR-associated gene product staining patterns. For example, in some embodiments, the clinician(s) is blinded to clinical characteristics and outcome for the samples, patients, etc. being assessed and scored.

In some embodiments, level of protein phosphorylation is determined. The phosphorylation status of a protein may be assessed from a variety of sample sources. In some embodiments, the sample is a tumor biopsy. The phosphorylation status of a protein may be assessed via a variety of methods. In some embodiments, the phosphorylation status is assessed using immunohistochemistry. The phosphorylation status of a protein may be site specific. The phosphorylation status of a protein may be compared to a control sample. In some embodiments, the phosphorylation status is assessed prior to initiation of the methods of treatment described herein. In some embodiments, the phosphorylation status is assessed after initiation of the methods of treatment described herein. In some embodiments, the phosphorylation status is assessed prior to and after initiation of the methods of treatment described herein.

Further provided herein are methods of directing treatment of a CNS disorder by delivering a sample to a diagnostic lab for determination of the level of an mTOR-associated gene; providing a control sample with a known level of the mTOR-associated gene; providing an antibody to a molecule encoded by the mTOR-associated gene or an antibody to a molecule encoded by a downstream target gene of the mTOR-associated gene; individually contacting the sample and control sample with the antibody, and/or detecting a relative amount of antibody binding, wherein the level of the sample is used to provide a conclusion that a patient should receive a treatment with any one of the methods described herein.

Also provided herein are methods of directing treatment of a CNS disorder, further comprising reviewing or analyzing data relating to the status (such as presence/absence or level) of an mTOR-activating aberration in a sample; and providing a conclusion to an individual, such as a health care provider or a health care manager, about the likelihood or suitability of the individual to respond to a treatment, the conclusion being based on the review or analysis of data. In one aspect of the application a conclusion is the transmission of the data over a network.

D. Resistance biomarkers

Genetic aberrations and aberrant levels of certain genes may be associated with resistance to the treatment methods described herein. In some embodiments, the individual having an aberration (such as genetic aberration or aberrant level) in a resistance biomarker is excluded from the methods of treatment using the mTOR inhibitor nanoparticles as described herein. In some embodiments, the status of the resistance biomarkers combined with the status of one or more of the mTOR-activating aberrations are used as the basis for selecting an individual for any one of the methods of treatment using mTOR inhibitor nanoparticles as described herein.

For example, TFE3, also known as transcription factor binding to IGHM enhancer 3, TFEA, RCCP2, RCCX1, or bHLHe33, is a transcription factor that specifically recognizes and binds MUE3-type E-box sequences in the promoters of genes. TFE3 promotes expression of genes downstream of transforming growth factor beta (TGF-beta) signaling. Translocation of TFE3 has been associated with renal cell carcinomas and other cancers. In some embodiments, the nucleic acid sequence of a wildtype TFE3 gene is identified by the Genbank accession number NC_000023.11 from nucleotide 49028726 to nucleotide 49043517 of the complement strand of chromosome X according to the GRCh38.p2 assembly of the human genome. Exemplary translocations of TFE3 that may be associated with resistance to treatment using the mTOR inhibitor nanoparticles as described herein include, but are not limited to, Xp11 translocation, such as t(X; 1)(p11.2; q21), t(X; 1)(p11.2; p34), (X; 17)(p11.2; q25.3), and inv(X)(p11.2; q12). Translocation of the TFE3 locus can be assessed using immunohistochemical methods or fluorescence in situ hybridization (FISH).

Articles of Manufacture and Kits

In some embodiments of the application, there is provided an article of manufacture containing materials useful for the treatment of a CNS disorder comprising an mTOR inhibitor nanoparticle composition (such as sirolimus/albumin nanoparticle composition). In some embodiments, there is provided an article of manufacture containing materials useful for the treatment of a CNS disorder comprising an mTOR inhibitor nanoparticle composition (such as sirolimus/albumin nanoparticle composition) and a second agent selected from an anti-VEGF antibody, a proteasome inhibitor (e.g., marizomib), an alkylating agent (e.g., temozolomide or lomustine), and an anti-epilepsy drug. In some embodiments of the application, there is provided an article of manufacture containing materials useful for the treatment of a CNS disorder comprising an mTOR inhibitor nanoparticle composition (such as sirolimus/albumin nanoparticle composition) and an agent for assessing an mTOR-activating aberration. In some embodiments, there is provided an article of manufacture containing materials useful for the treatment of a CNS disorder comprising an mTOR inhibitor nanoparticle composition (such as sirolimus/albumin nanoparticle composition); a second agent selected from the group consisting of an anti-VEGF antibody, a proteasome inhibitor (e.g., marizomib), an alkylating agent (e.g., temozolomide or lomustine), and an anti-epilepsy drug; and a third agent for assessing an mTOR-activating aberration.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is a) a nanoparticle formulation of an mTOR inhibitor; or b) an agent selected from the list consisting of an anti-VEGF antibody, a proteasome inhibitor (e.g., marizomib), an alkylating agent (e.g., temozolomide or lomustine) and an anti-epilepsy drug. The label or package insert indicates that the composition is used for treating the particular CNS disorder in an individual. The label or package insert will further comprise instructions for administering the composition to the individual. Articles of manufacture and kits comprising combination therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a CNS disorder.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a CNS disorder. Kits of the application include one or more containers comprising an mTOR inhibitor nanoparticle composition (such as sirolimus/albumin nanoparticle composition) (or unit dosage form and/or article of manufacture), and in some embodiments, further comprise an agent selected from an anti-VEGF antibody, a proteasome inhibitor (e.g., marizomib), an alkylating agent (e.g., temozolomide or lomustine) and an anti-epilepsy drug, and/or instructions for use in accordance with any of the methods described herein. In some embodiments, the kit further comprises an agent for assessing an mTOR-activating aberration (such as PTEN aberration). The kit may further comprise a description of selection of individuals suitable for treatment. Instructions supplied in the kits of the application are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an mTOR inhibitor nanoparticle composition (such as sirolimus/albumin nanoparticle composition). In some embodiments, the kit comprises a) a composition comprising an mTOR inhibitor nanoparticle composition (such as sirolimus/albumin nanoparticle composition), and b) a second agent selected from an anti-VEGF antibody, a proteasome inhibitor (e.g., marizomib), an alkylating agent (e.g., temozolomide or lomustine) and an anti-epilepsy drug. In some embodiments, the kit comprises a) a composition comprising an mTOR inhibitor nanoparticle composition (such as sirolimus/albumin nanoparticle composition), and b) instructions for administering the mTOR inhibitor nanoparticle composition, optionally in combination with a second agent selected from an anti-VEGF antibody, a proteasome inhibitor (e.g., marizomib), an alkylating agent (e.g., temozolomide or lomustine) and an anti-epilepsy drug to an individual for treatment of a CNS disorder. In some embodiments, the kit comprises a) a composition comprising an mTOR inhibitor nanoparticle composition (such as sirolimus/albumin nanoparticle composition), b) a second agent selected from the group consisting of an anti-VEGF antibody, a proteasome inhibitor (e.g., marizomib), an alkylating agent (e.g., temozolomide or lomustine) and an anti-epilepsy drug, and c) instructions for administering the mTOR inhibitor nanoparticle composition and a second agent selected from the group consisting of an anti-VEGF antibody, a proteasome inhibitor (e.g., marizomib), an alkylating agent (e.g., temozolomide or lomustine) and an anti-epilepsy drug to an individual for treatment of a CNS disorder. In some embodiments, the kit comprises a) a composition comprising an mTOR inhibitor nanoparticle composition (such as sirolimus/albumin nanoparticle composition), b) a second agent selected from the group consisting of an anti-VEGF antibody, a proteasome inhibitor (e.g., marizomib), an alkylating agent (e.g., temozolomide or lomustine) and an anti-epilepsy drug, c) a third agent for assessing an mTOR-activating aberration, and d) instructions for administering the mTOR inhibitor nanoparticle composition and a second agent selected from the group consisting of an anti-VEGF antibody, a proteasome inhibitor (e.g., marizomib), an alkylating agent (e.g., temozolomide or lomustine) and an anti-epilepsy drug to an individual for treatment of a CNS disorder. The mTOR inhibitor nanoparticle composition (such as sirolimus/albumin nanoparticle composition) and a second agent selected from the group consisting of an anti-VEGF antibody, a proteasome inhibitor (e.g., marizomib), an alkylating agent (e.g., temozolomide or lomustine) and an anti-epilepsy drug can be present in separate containers or in a single container. For example, the kit may comprise one distinct composition or two or more compositions wherein one composition comprises an mTOR inhibitor nanoparticle composition (such as sirolimus/albumin nanoparticle composition) and another composition comprises the second agent selected from the group consisting of an anti-VEGF antibody, a proteasome inhibitor (e.g., marizomib), an alkylating agent (e.g., temozolomide or lomustine) and an anti-epilepsy drug.

The kits of the application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the mTOR inhibitor nanoparticle composition (such as sirolimus/albumin nanoparticle composition) and the second agent selected from the group consisting of an anti-VEGF antibody, a proteasome inhibitor (e.g., marizomib), an alkylating agent (e.g., temozolomide or lomustine) and an anti-epilepsy drug generally include information as to dosage, dosing schedule, and route of administration for the intended treatment. The containers may be unit doses, bulk packages (e.g., multi-dose packages) or sub-unit doses. For example, kits may be provided that contain sufficient dosages of an mTOR inhibitor nanoparticle composition (such as sirolimus/albumin nanoparticle composition) and a second agent selected from the group consisting of an anti-VEGF antibody, a proteasome inhibitor (e.g., marizomib), an alkylating agent (e.g., temozolomide or lomustine) and an anti-epilepsy drug as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, 12 months, 24 months or more. Kits may also include multiple unit doses of the mTOR inhibitor nanoparticle composition (such as sirolimus/albumin nanoparticle composition) and a second agent selected from the group consisting of an anti-VEGF antibody, a proteasome inhibitor (e.g., marizomib), an alkylating agent (e.g., temozolomide or lomustine) and an anti-epilepsy drug and instructions for use, packaged in quantities sufficient for storage and use in pharmacies, for example, hospital pharmacies and compounding pharmacies.

Those skilled in the art will recognize that several embodiments are possible within the scope and spirit of this application. The application will now be described in greater detail by reference to the following non-limiting examples. The following examples further illustrate the application but, of course, should not be construed as in any way limiting its scope.

EXEMPLARY EMBODIMENTS

Embodiment 1. A method of treating a CNS disorder in an individual, comprising systemically administering to the individual an effective amount of a composition comprising nanoparticles comprising an mTOR inhibitor and an albumin.

Embodiment 2. The method of embodiment 1, wherein the amount of the mTOR inhibitor in the nanoparticle composition is from about 0.1 mg/m$^2$ to about 120 mg/m$^2$ for each administration.

Embodiment 3. The method of embodiment 1 or embodiment 2, wherein the nanoparticle composition is administered once every week, twice every three weeks, or three times every four weeks.

Embodiment 4. The method of any one of embodiments 1-3, wherein the average diameter of the nanoparticles in the nanoparticle composition is no greater than about 200 nm.

Embodiment 5. The method of any one of embodiments 1-4, wherein the weight ratio of the albumin to the mTOR inhibitor in the nanoparticle composition is no greater than about 9:1.

Embodiment 6. The method of any one of embodiments 1-5, wherein the nanoparticles comprise the mTOR inhibitor associated with the albumin.

Embodiment 7. The method of any one of embodiments 1-6, wherein the nanoparticles comprise the mTOR inhibitor coated with the albumin.

Embodiment 8. The method of any one of embodiments 1-7, wherein the nanoparticle composition is administered for at least about one to six cycles, wherein each cycle consists of 21 days or 28 days.

Embodiment 9. The method of any one of embodiments 1-8, wherein the mTOR inhibitor is a limus drug.

Embodiment 10. The method of embodiment 9, wherein the mTOR inhibitor is rapamycin.

Embodiment 11. The method of any one of embodiments 1-10, wherein the CNS disorder is epilepsy.

Embodiment 12. The method of embodiment 11, wherein the individual has undergone an epilepsy surgery.

Embodiment 13. The method of embodiment 12, wherein the individual has at least 5 seizures in 30 days post epilepsy surgery or does not have a week of seizure freedom following epilepsy surgery.

Embodiment 14. The method of any one of embodiments 11-13, wherein the method further comprises administering to the individual an effective amount of an anti-epilepsy agent.

Embodiment 15. The method of any one of embodiments 11-14, wherein the amount the mTOR inhibitor in the nanoparticle composition is from about 0.1 mg/m$^2$ to about 25 mg/m$^2$ for each administration.

Embodiment 16. The method of any one of embodiments 1-10, wherein the CNS disorder is glioblastoma.

Embodiment 17. The method of embodiment 16, wherein the glioblastoma is recurrent glioblastoma.

Embodiment 18. The method of embodiment 16, wherein the glioblastoma is newly diagnosed glioblastoma.

Embodiment 19. The method of embodiment 18, wherein the individual has undergone surgical resection of newly diagnosed glioblastoma prior to the initiation of the nanoparticle administration.

Embodiment 20. The method of any one of embodiments 16-19, further comprising administering to the individual an effective amount of a second agent selected from the group consisting of an anti-VEGF antibody, an alkylating agent and a proteasome inhibitor.

Embodiment 21. The method of any one of embodiments 16-20, wherein the amount of the mTOR inhibitor in the nanoparticle composition is from about 20 mg/m$^2$ to about 100 mg/m$^2$ for each administration.

Embodiment 22. The method of embodiment 20 or embodiment 21, wherein the second agent is an anti-VEGF antibody.

Embodiment 23. The method of embodiment 22, wherein the anti-VEGF antibody is bevacizumab.

Embodiment 24. The method of embodiment 22 or embodiment 23, wherein the amount of the anti-VEGF is from about 1 mg/kg to about 5 mg/kg for each administration.

Embodiment 25. The method of any one of embodiments 22-24, wherein the anti-VEGF antibody is administered once every two weeks.

Embodiment 26. The method of embodiment 22 or embodiments 23, wherein the anti-VEGF antibody is administered at an amount of less than about 5 mg/kg each week.

Embodiment 27. The method of any one of embodiments 22-26, wherein the anti-VEGF antibody is administered within an hour of the administration of the nanoparticles.

Embodiment 28. The method of embodiment 20 or embodiment 21, wherein the second agent is a proteasome inhibitor.

Embodiment 29. The method of embodiment 28, wherein the proteasome inhibitor is marizomib.

Embodiment 30. The method of embodiment 28 or embodiment 29, wherein the amount of the proteasome inhibitor is about 0.1 mg/m$^2$ to about 5.0 mg/m$^2$ for each administration.

Embodiment 31. The method of any one of embodiments 28-30, wherein the proteasome inhibitor is administered three times every four weeks.

Embodiment 32. The method of any one of embodiments 28-31, wherein the proteasome inhibitor is administered within an hour of the administration of the nanoparticles.

Embodiment 33. The method of embodiment 20 or embodiment 21, wherein the second agent is an alkylating agent.

Embodiment 34. The method of embodiment 33, wherein the alkylating agent is temozolomide.

Embodiment 35. The method of embodiment 33 or 34, wherein the amount of the alkylating agent is about 25 mg/m$^2$ to about 100 mg/m$^2$.

Embodiment 36. The method of embodiment 35, wherein the amount of the alkylating agent is about 50 mg/m$^2$.

Embodiment 37. The method of any one of embodiments 33-36, wherein the alkylating agent is administered daily.

Embodiment 38. The method of embodiment 36 or 37, wherein the alkylating agent is administered daily for at least about three weeks.

Embodiment 39. The method of embodiment 34 or 35, wherein the amount of the alkylating agent is about 125 mg/m$^2$ to about 175 mg/m$^2$ for each administration.

Embodiment 40. The method of embodiment 39, wherein the alkylating agent is administered about 4-6 times every four weeks.

Embodiment 41. The method of embodiment 40, wherein the alkylating agent is administered daily for five consecutive days every four weeks.

Embodiment 42. The method of embodiment 41, wherein the alkylating agent is administered for at least six cycles, wherein each cycle consists of twenty-eight days.

Embodiment 43. The method of any one of embodiments 34-42, wherein the alkylating agent is administered orally.

Embodiment 44. The method of any one of embodiments 34-43, wherein the method further comprises radiotherapy.

Embodiment 45. The method of embodiment 44, wherein the radiotherapy is a focal radiotherapy.

Embodiment 46. The method of embodiment 45, wherein the focal radiotherapy is administered daily.

Embodiment 47. The method of embodiment 45 or embodiment 46, wherein about 40-80 Gy focal radiotherapy is administered each week.

Embodiment 48. The method of embodiment 33, wherein the alkylating agent is a nitrosourea compound.

Embodiment 49. The method of embodiment 48, wherein the compound is lomustine.

Embodiment 50. The method of embodiment 48 or embodiment 49, wherein the amount of the nitrosourea compound is about 80 mg/m$^2$ to about 100 mg/m$^2$ for each administration.

Embodiment 51. The method of any one of embodiments 48-50, wherein the nitrosourea compound is administered orally.

Embodiment 52. The method of any one of embodiments 48-51, wherein the nitrosourea compound is administered once every six weeks.

Embodiment 53. The method of any one of embodiments 16-52, wherein the glioblastoma comprises an mTOR-activation aberration.

Embodiment 54. The method of embodiment 53, wherein the mTOR-activation aberration comprises a PTEN aberration.

Embodiment 55. The method of any one of embodiments 1-54, wherein the individual is a human.

Embodiment 56. The method of any one of embodiments 1-55, wherein the nanoparticle composition is parenterally administered into the individual.

Embodiment 57. The method of embodiment 56, wherein the nanoparticle composition is intravenously administered into the individual.

Embodiment 58. The method of embodiment 56, wherein the nanoparticle composition is subcutaneously administered into the individual.

Embodiment 59. A kit comprising a nanoparticle composition comprising an mTOR inhibitor and an albumin for treating a CNS disorder.

Embodiment 60. The kit of embodiment 59, further comprising an agent selected from the group consisting of an anti-VEGF antibody, an alkylating agent and a proteasome inhibitor.

Embodiment 61. The kit of embodiment 59 or 60, further comprising an agent for assessing an mTOR-activating aberration.

EXAMPLES

Example 1: Use of Nab-Rapamycin as a Single Drug Therapy or in Combination with a Second Agent in Patients with Recurrent Glioblastoma (rGBM)

ABI-009 ("nab-rapamycin") is rapamycin protein-bound nanoparticles for injectable suspension (albumin bound). This study is a phase 2, open-label study of ABI-009 (nab-Rapamycin) in bevacizumab-naïve subjects with progressive glioblastoma following prior therapy to evaluate the safety and activity of intravenous ABI-009 as a single agent and in combination with bevacizumab (BEV), marizomib (MRZ), temozolomide (TMZ) or lomustine (CCNU) in subjects with recurrent glioblastoma without prior exposure to BEV, mTOR inhibitors, or MRZ. This study also aims to evaluate the safety and activity of ABI-009 as a single agent or in combination with BEV, MRZ, TMZ, and CCNU in the subject population.
A. Therapy Administration
2. Use of Nab-Rapamycin as a Single Agent ABI-009 is administered IV to subjects at 100 mg/m$^2$ as a 30-minute IV infusion on Days 1 and 8 of every 21-day cycle. Two dose reduction levels of ABI-009 are allowed: 75 mg/m$^2$ and 56 mg/m$^2$.
3. Use of nab-rapamycin in combination with bevacizumab (BEV)

ABI-009 is administered intravenously to subjects at 56 mg/m$^2$ as a 30-minute IV infusion on Days 1, 8, and 15 of every 28-day cycle. This dose is about 50% lower than the maximum tolerated dose (MTD) of 100 mg/m$^2$ as determined in a previous Phase 1 study in subjects with solid tumors (Gonzalez-Angulo et al. 2013). Two dose reduction levels of ABI-009 are allowed: 45 mg/m$^2$ and 30 mg/m$^2$.

Bevacizumab (BEV) is administered as an IV infusion (90 minutes 1st dose, 60 minutes 2nd dose and 30 minutes afterward assuming tolerability) at a fixed dose of 5 mg/kg on Days 1 and 15 of every 28-day cycle. BEV is administered approximately 10 minutes after the end of the ABI-009. Without being bound to the theory, it is hypothesized that lower doses of BEV may potentially improve chemotherapy delivery and ultimately patient outcome (Weathers et al. 2016). In one retrospective analysis, low dose intensity bevacizumab (<5 mg/kg/week) was associated with improved PFS and OS with an inverse relationship seen between dose-intensity and overall survival when compared with normal dose intensity bevacizumab at 10 mg/kg (Lorgis et al. 2012). Therefore, the BEV dose of 5 mg/kg is chosen for this study.
4. Use of Nab-Rapamycin in Combination with Marizomib (MRZ)

ABI-009 is administered IV at 56 mg/m$^2$ as a 30-minute IV infusion on Days 1, 8, and 15 of every 28-day cycle. Two dose reduction levels of ABI-009 are allowed: 45 mg/m$^2$ and 30 mg/m$^2$.

MRZ is administered at 0.8 mg/m$^2$ as a 10-minute IV infusion on Days 1, 8, and 15 of every 28-day cycle. MRZ is administered approximately 10 minutes after the end of the ABI-009 infusion.
5. Use of Nab-Rapamycin in Combination with Temozolomide (TMZ)

ABI-009 is administered IV at 56 mg/m$^2$ as a 30-minute IV infusion on Days 1, 8, and 15 of every 28-day cycle. Two dose reduction levels of ABI-009 are allowed: 45 mg/m$^2$ and 30 mg/m$^2$.

TMZ is orally administered at 50 mg/m$^2$ daily.
6. Use of Nab-Rapamycin in Combination with Lomustine (CCNU)

ABI-009 is administered IV at 56 mg/m$^2$ as a 30-minute IV infusion on Days 1 and 8 of every 21-day cycle. Two dose reduction levels of ABI-009 are allowed: 45 mg/m$^2$ and 30 mg/m$^2$.

CCNU is orally administered at 90 mg/m$^2$ every 6 weeks.

Subjects in any of the therapies described above continue to receive therapy until disease progression, unacceptable toxicity, until in the opinion of the investigator the subject is no longer benefiting from therapy, or at the subject's discretion.
B. Endpoints and Criteria to Evaluate Efficacy and Safety
1. Endpoints The primary endpoint for this study is the objective overall response rate (ORR, as determined by independent radiologic assessment using RANO 2010 criteria). The secondary endpoints for this study include duration of response (DOR), progression-free survival (PFS) rate at 6 months, PFS, overall survival (OS), and safety. This study also has exploratory endpoints including 1) assessment of pre-treatment archived tumor samples for the activity of mTOR pathway and correlation with activity/tolerability (e.g., number of seizures per week, quality of life (QOL)); 2) if available, tumor biomarkers post-progression (e.g., number of seizures per week or during the course, QOL); and 3) trough level of rapamycin following weekly treatment.
2. Criteria to Evaluate Efficacy For subjects under the combination therapies of ABI-009 with BEV, MRZ or TMZ, tumor responses, including complete response (CR), partial response (PR), stable disease (SD), or progressive disease (PD), are assessed with MRI imaging every 2 cycles (every 8 weeks, at the end of each even-numbered cycle of therapy) according to the RANO 2010 criteria, including: Radiographic Response Rate; Progression-free Survival (PFS) and Overall Survival (OS). For subjects under the single agent therapy of ABI-009 and combination therapy of ABI-009 with CCNU, tumor responses are assessed with MRI imaging every 6 weeks.

After disease progression, patients is followed for survival every 12 weeks, or more frequently as needed, until death, withdrawal of consent, or the study closes, whichever is the earliest.

The primary endpoint is ORR by independent radiologic review, and is defined as the proportion of subjects who achieve a confirmed PR or CR per RANO 2010 criteria. DOR, PFS at 6 months, median PFS, and OS will be summarized using Kaplan-Meier (KM) analysis. Quartiles with 95% CIs are summarized.

3. Criteria to Evaluate Safety

Subjects are evaluated for safety analysis if they receive at least one dose of ABI-009. Safety and tolerability are monitored through continuous reporting of treatment-emergent and treatment-related adverse events (AEs), AEs of special interest, laboratory abnormalities, and incidence of patients experiencing dose modifications, dose delay/dose not given, dose interruptions, and/or premature discontinuation of IP due to an AE. All AEs are recorded by the investigator from the time the patient signs informed consent until 28 days after the last dose of IP. Adverse events are graded by National Cancer Institute (NCI) Common Terminology Criteria for Adverse Events (CTCAE) v4.03.

Physical examination, vital sign, laboratory assessments (e.g., serum chemistry, hematology), and ECOG performance status are monitored. All SAEs (regardless of relationship to IP) are followed until resolution. Laboratory analysis will be performed as per study schedule.

The treated population (Full Analysis Set) is the analysis population for all safety analyses. Adverse events are coded using the Medical Dictionary for Medical Activities (MedDRA) and grouped by their system organ class and preferred term. Summary tables include the number and percentage of patients with AEs, serious AEs, fatal AEs and other AEs of interest.

C. Patients

A patient is eligible for inclusion in this study only if all of the following criteria are met. 1. All subjects must have histologic evidence of glioblastoma and radiographic evidence of recurrence or disease progression (defined as either a greater than 25% increase in the largest bi-dimensional product of enhancement, a new enhancing lesion, or a significant increase in T2 FLAIR). Subjects must have at least 1 measurable lesion by RANO criteria (10 mm in 2 perpendicular diameters). 2. Subjects must have previously completed standard radiation therapy and been subjected to temozolomide. 3. Subjects under any of the therapies described above are not under prior treatment with an mTOR inhibitor. Subjects under the combination therapy of the ABI-009 and BEV are not under prior treatment with BEV or any other anti-angiogenic agents, including sorafenib, sunitinib, axitinib, pazopanib, or cilengitide. Subjects under the combination therapy of ABI-009 and MRZ are not under any prior treatment with MRZ or any other proteasome inhibitors, including bortezomib (BTZ), carfilzomib (CFZ), or ixazomib (IXZ). 4. There have been at least 4 weeks from surgical resection and at least 12 weeks from the end of radiotherapy prior to enrollment in this study, unless relapse is confirmed by tumor biopsy or new lesion outside of radiation field, or if there are two MRIs confirming progressive disease that are approximately 8 weeks apart. 5. Karnofsky Performance Status (KPS) score ≥70%. 6. No investigational agent within 4 weeks prior to the first dose of study drug. 7. All AEs resulting from prior therapy and surgery must have resolved to NCI-CTCAE (v. 4.03) Grade ≤1 (except for laboratory parameters outlined below). 8. Adequate hematological, renal, and hepatic function (assessment performed within 14 days prior to study treatment) including: a) absolute neutrophil count ≥1.5×109/L; b) platelets ≥100×109/L; c) hemoglobin ≥9 g/dL; d) serum creatinine ≤1.5× upper limit of laboratory normal (ULN); e) total serum bilirubin ≤1.5×ULN, or ≤3×ULN if Gilbert's disease is documented; f) Aspartate Serine Transaminase (AST), Aspartate Leucine Transaminase (ALT), Alkaline Phosphatase (ALP) ≤2.5×ULN; and f) serum triglyceride <300 mg/dL and serum cholesterol <350 mg/dL. 9. Subjects are without seizures for at least 14 days prior to enrollment, and patients who receive treatment with anti-epileptic drugs (AEDs) are on stable doses for at least 14 days prior to enrollment. 10. Steroid therapy for control of cerebral edema is allowed at the discretion of the Investigator. Subjects are on stable or decreasing dose of corticosteroids for at least 1 week prior to the first dose of study drug.

D. Duration of Treatment

The study takes approximately 32 months from first patient enrolled to last patient follow-up, including approximately 24 months of enrollment period, an estimated 6 months of treatment (or until acceptable toxicity or disease progression) and an end of treatment visit at 4 weeks (+/−7 days) after last treatment.

The End of Study (EOS) defined as either the date of the last visit of the last patient to complete the study, or the date of receipt of the last data point from the last patient that is required for primary, secondary, and/or exploratory analysis, as pre-specified in the protocol.

End of Treatment (EOT) for a patient is defined as the date of the last dose of ABI-009. End of Treatment Visit for a patient is when safety assessments and procedures are performed after the last treatment, which must occur at least 4 weeks (±7 days) after the last dose of ABI-009.

Follow-up period is the on-study time period after the EOT Visit. All patients that discontinue study drug and have not withdrawn full consent to participate in the study will continue in the follow-up phase for survival and initiation anticancer therapy. Follow up will continue approximately every 12 weeks (+/−3 weeks), until death, withdrawal of consent, or the study closes, whichever is the earliest. This evaluation may be made by record review and/or telephone contact.

E. A Phase 2, Open-Label Study of ABI-009 (Nab-Rapamycin) in Bevacizumab-Naïve Patients with Recurrent High-Grade Glioma.

Patients in different cohorts as discussed below in detail were treated with ABI-009. Patients in cohorts 2-4 were also treated with a second agent. 1. Cohort 1, ABI-009 at 100/mg/m$^2$ Patient I has Grade 4 GBNM and has undergone completed surgery, standard TMZ/RT treatment, Optune device for ndGBM, and surgery for recurrent disease. Patient I was treated with ABI-009 at 100 mg/m$^2$, on study for 3 cycles (9 weeks).

Patient 2 has Grade 4 GBM and has undergone completed surgery, standard TMZ/RT treatment for ndGBM, surgery for recurrent disease. Patient 2 was treated with ABI-009 at 100 mg/m$^2$, on study for 2 cycles (6 weeks).

Patient 3 has Grade 4 GBM and has undergone completed surgery, standard TMZ/RT treatment for ndGBNM and surgery for recurrent disease. Patient 3 was treated with ABI-009 at 100 mg/m$^2$, on study for 3 cycles (9 weeks).

Patient 4 has Grade 4 GBM and has undergone completed surgery, standard TMZ/RT treatment for ndGBM. Patient 4 has had no treatment for recurrent disease. Patient 4 treated with AB1-009 at 100 mg/m$^2$, then dose reduced to 75 then 60 mg/m$^2$, stayed on study for 3 cycles (9 weeks).

2. Cohort 2, ABI-009 at 60/Mg/m², TMZ at 50 mg/m²

Patient 1 has Grade 4 GBM and has undergone completed surgery and standard TMZ/RT treatment for ndGBM. Patient 1 has had no treatment for recurrent disease. Patient 1 was treated with ABI-009 at 60 ng/m², then dose reduced to 45 mg/hn², on study for 5 weeks. 3. Cohort 3, ABI-009 at 60/mg/m², BEV at 5 mg/kg Patient 1 has Grade 3 Anaplastic Oligodendroglioma and has undergone completed surgery for newly diagnosed high-grade gliomas (ndHGG) and surgery for recurrent disease. Patient was treated with ABI-009 at 60 mg/m², on study for 1 cycle (4 weeks).

Patient 2 has Grade 4 GBM and has undergone completed surgery and standard TMZ/RT treatment for ndGBM. Patient 2 has had no treatment for recurrent disease. Patient 2 was treated with ABI-009 at 60 mg/m², on study for 2 weeks. 4. Cohort 4, ABI-009 at 60/mg/m², CCNU at 90 mg/m²

Patient 1 has Grade 4 GBM and has undergone completed surgery and standard TMZ/RT treatment, Optune device, marizomib for ndGBM, and CAR-T cell immunotherapy for recurrent disease. Patient 1 was treated with ABI-009 at 60 mg/m², on study for 1 cycle (3 weeks)

Example 2: Use of Nab-Rapamycin as a Single Drug Therapy or in Combination with a Second Agent in Patients with Newly Diagnosed Glioblastoma (ndGBM)

As discussed above, ABI-009 ("nab-rapamycin") is rapamycin protein-bound nanoparticles for injectable suspension (albumin bound). This study is a phase 2, open-label study of ABI-009 (nab-Rapamycin) in subjects with newly diagnosed glioblastoma to evaluate the safety and activity of 1) ABI-009 as a single agent (see initiation treatment below), 2) the combination of ABI-009, temozolomide (TMZ) and radiotherapy (RT) (see concomitant treatment, and 3) the combination of ABI-009 and TMZ.

A. Therapy Administration

The therapy includes three phases of treatments: a) Initiation Treatment; b) Concomitant Treatment; and c) Adjuvant Treatment.

1. Initiation Treatment

Initiation Treatment starts 3-4 weeks following surgical resection of ndGBM. For subjects with enhancing tumor as detected by MRI, ABI-009 is administered IV at 100 mg/m² as a 30-minute IV infusion every week for 4 weeks. Two dose reduction levels are allowed: 75 mg/m² and 56 mg/m².

2. Concomitant Treatment

Concomitant Treatment starts 1 week after the completion of Initiation Treatment and lasts for 6 weeks. ABI-009 is administered IV at 56 mg/m² as a 30-minute IV infusion on Days 8 and 15 of every 21-day cycle. Two dose reduction levels are allowed: 45 mg/m² and 30 mg/m². TMZ is orally administered at 75 mg/m² daily for 6 weeks. Focal radiotherapy is given daily at 30×200 cGy, 5 days/week for a total dose of 60 Gy. 3. Adjuvant Treatment Adjuvant Treatment starts 4 weeks after the completion of Concomitant Treatment and will last for 24 weeks. ABI-009 is administered IV at 56 mg/m² as a 30-minute IV infusion on Days 1, 8, and 15 of every 28-day cycle for 6 cycles. Two dose reduction levels are allowed: 45 mg/m² and 30 mg/m². TMZ is orally administered at 150 mg/m² daily on Days 1-5 of every 28-day cycle for 6 cycles.

B. Endpoints and Criteria to Evaluate Efficacy and Safety

1. Endpoints

The primary endpoint for this study is the objective overall response rate (ORR, as determined by independent radiologic assessment using RANO 2010 criteria). The secondary endpoints for this study include PFS, OS, and safety. This study also has exploratory endpoints including 1) assessment of pre-treatment archived tumor samples for the activity of mTOR pathway and correlation with activity/tolerability (e.g., number of seizures per week, quality of life (QOL)); 2) if available, tumor biomarkers post-progression (e.g., number of seizures per week or during the course, QOL); and 3) trough level of rapamycin following weekly treatment.

2. Criteria to Evaluate Efficacy

Tumor response is assessed with MRI imaging 1 week after the completion of Initiation Treatment, 4 weeks after the completion of radiotherapy, and every 3 months thereafter.

After disease progression, patients is followed for survival every 12 weeks, or more frequently as needed, until death, withdrawal of consent, or the study closes, whichever is the earliest.

The primary endpoint is ORR by independent radiologic review, and is defined as the proportion of subjects who achieve a confirmed PR or CR per RANO 2010 criteria. DOR, PFS at 6 months, median PFS, and OS will be summarized using Kaplan-Meier (KM) analysis. Quartiles with 95% CIs are summarized.

3. Criteria to evaluate safety

Subjects are evaluated for safety analysis if they receive at least one dose of ABI-009. Safety and tolerability are monitored through continuous reporting of treatment-emergent and treatment-related adverse events (AEs), AEs of special interest, laboratory abnormalities, and incidence of patients experiencing dose modifications, dose delay/dose not given, dose interruptions, and/or premature discontinuation of IP due to an AE. All AEs are recorded by the investigator from the time the patient signs informed consent until 28 days after the last dose of IP. Adverse events are graded by National Cancer Institute (NCI) Common Terminology Criteria for Adverse Events (CTCAE) v4.03.

Physical examination, vital sign, laboratory assessments (e.g., serum chemistry, hematology), and ECOG performance status are monitored. All SAEs (regardless of relationship to IP) are followed until resolution. Laboratory analysis will be performed as per study schedule.

The treated population (Full Analysis Set) is the analysis population for all safety analyses. Adverse events are coded using the Medical Dictionary for Medical Activities (MedDRA) and grouped by their system organ class and preferred term. Summary tables include the number and percentage of patients with AEs, serious AEs, fatal AEs and other AEs of interest.

C. Patients

A patient is eligible for inclusion in this study only if all of the following criteria are met. 1. The patient is histologically confirmed to have newly diagnosed glioblastoma. 2. The patient has had surgery and has a measurable post-contrast lesion after surgery detected by MRI. 3. There is no prior treatment with mTOR inhibitors, and no prior local or systemic therapy for GBM. 4. Karnofsky Performance Status (KPS) score ≥70%. 5. No investigational agent within 4 weeks prior to the first dose of study drug. 6. All AEs resulting from prior therapy and surgery must have resolved to NCI-CTCAE (v. 4.03) Grade ≤1 (except for laboratory parameters outlined below). 7. Adequate hematological, renal, and hepatic function (assessment performed within 14 days prior to study treatment) including: a) absolute neutrophil count ≥1.5×109/L; b) platelets ≥100×109/L; c) hemoglobin ≥9 g/dL; d) serum creatinine 1.5× upper limit of laboratory normal (ULN); e) total serum bilirubin ≤1.5× ULN, or ≤3×ULN if Gilbert's disease is documented; f) Aspartate Serine Transaminase (AST), Aspartate Leucine Transaminase (ALT), Alkaline Phosphatase (ALP) ≤2.5× ULN; and f) serum triglyceride <300 mg/dL and serum cholesterol <350 mg/dL. 8. Subjects are without seizures for at least 14 days prior to enrollment, and patients who receive treatment with anti-epileptic drugs (AEDs) are on stable doses for at least 14 days prior to enrollment. 9. Steroid therapy for control of cerebral edema is allowed at the discretion of the Investigator. Subjects are on stable or decreasing dose of corticosteroids for at least 1 week prior to the first dose of study drug.

D. Duration of treatment

This study takes approximately 24 months from first patient enrolled to last patient follow-up, including approximately 16 months of enrollment period, up to 12 months of treatment (or until acceptable toxicity or disease progression) and an end of treatment visit at 4 weeks (+/−7 days) after last treatment.

The End of Study (EOS) defined as either the date of the last visit of the last patient to complete the study, or the date of receipt of the last data point from the last patient that is required for primary, secondary, and/or exploratory analysis, as pre-specified in the protocol.

End of Treatment (EOT) for a patient is defined as the date of the last dose of ABI-009. End of Treatment Visit for a patient is when safety assessments and procedures are performed after the last treatment, which must occur at least 4 weeks (±7 days) after the last dose of ABI-009.

Follow-up period is the on-study time period after the EOT Visit. All patients that discontinue study drug and have not withdrawn full consent to participate in the study will continue in the follow-up phase for survival and initiation anticancer therapy. Follow up will continue approximately every 12 weeks (+/−3 weeks), until death, withdrawal of consent, or the study closes, whichever is the earliest. This evaluation may be made by record review and/or telephone contact.

Example 3: Use of Nab-rapamycin in Patients with Surgically-Refractory Epilepsy

As discussed above, ABI-009 ("nab-rapamycin") is rapamycin protein-bound nanoparticles for injectable suspension (albumin bound). This is a prospective, single-center, phase I safety study to investigate the safety, tolerability, seizure control, and quality of life in patients with medically-refractory epilepsy who failed epilepsy surgery. These patients have continued seizures despite being at least 3 months post-epilepsy surgery (resective surgery with intent to cure). Upon enrollment, patients are continued and observed on their pre-existing, clinically prescribed anti-epilepsy drugs (AED) regimen for 1 month. At the 1-month mark, patients receive weekly ABI-009 intravenously at different dose levels in cohorts of 3 patients each using the standard 3+3 dose-finding design. ABI-009 is continued for a total of 24 weeks. ABI-009 is then discontinued and the patients are observed for an additional 3 months.

A. Therapy administration
1. ABI-009

For dose finding, the administration of ABI-009 starts at 5 mg/m²/dose IV on Days 1, 8, 15, and 28 of every 4 week cycle, in cohorts of 3 patients each using the standard 3+3 dose-finding design. See Table 1.

TABLE 1

| Dose-levels | ABI-009 in mg/m² |
| --- | --- |
| −2 | 1 |
| −1 | 2.5 |
| 1 | 5 |
| 2 | 10 |
| 3 | 20 |

Escalation to the next dose level with a new cohort of 3 patients occurs after no DLT was observed in the first 2 treatment cycles (6 weeks). There is no intra-patient dose escalation allowed. If a DLT occurs in a cohort, additional 3 patients are recruited to the cohort. If no further DLTs occur, then a new cohort of 3 patients at the next higher dose level can be enrolled. If 2/6 patients at dose level 1 experience a DLT, then that cohort is closed to further enrollment and 3 patients are enrolled at the next lower dose level, and so on. The MTD is the highest dose level in which ≤1 patient has a DLT.

ABI-009 is administered IV every seven days, on Days 1, 8, X+7, etc. for a total of 24 weeks.

2. Concomitant Medications

Standard therapy for epilepsy is allowed except for treatments noted in the prohibited medications section below. Rescue medication is allowed for prolonged seizure event or cluster of seizures.

The following medication changes are prohibited during participation in the trial, and as such will be considered a protocol violation. 1. The therapy that results in any changes in dosage of AED regimen, unless solely to address subtherapeutic levels of AEDs as determined by the treating neurologist. 2. The therapy that result in any additions or removal of AEDs to the subject's AED regimen during participation unless medically necessary and discussed with investigator.

3. Control

Subjects serve as their own controls by continuing their pre-existing AED regimen for 1 month after enrollment prior to starting treatment with ABI-009. At the time of treatment, to proceed with drug administration subjects have to have had >8 seizures in 30 days without 2 weeks of seizure freedom.

B. Objectives and Endpoints
1. Objectives

The primary objectives of this study are as following: 1) to determine dose-limiting toxicities (DLTs) and maximum tolerated dose (MTD) of ABI-009 in patients with surgically-refractory epilepsy; 2) to record the AEs and document their severity with ABI-009 therapy for medically intractable epilepsy that has failed surgical resection, administered in conjunction with their pre-existing AED regimen; and 3) to record the compliance of families with medication, and record the number of patients that withdraw from treatment either voluntarily or by necessity secondary to AEs.

The secondary objectives are to 1) change in seizure frequency (% of patients demonstrating ≥50% reduction) from week 0-4 (baseline) to week 16 and 24 after start of treatment with ABI-009 in conjunction with pre-existing AED regimens, then at 3-months post end of treatment; 2) evaluate quality of life indices for subjects before, during, and after treatment with ABI-009 in conjunction with pre-existing AED regimens.

2. Endpoints

The primary endpoints include the following: 1) DLT; 2) MTD; 3) incidence of adverse events and clinically significant abnormal lab values; 4) number of subjects withdrawn from study; and 5) adherence to prescribed ABI-009 regimen.

The secondary endpoints include: 1) seizure frequency, expressed as both number of seizures/week and percent reduction from baseline seizure frequency; 2) quality of life and behavioral index.

C. Patients

A patient is eligible for inclusion in this study only if all of the following criteria are met. 1. The patient is no more than 26 years old and no less than three years old at the first visit. 2. The patient has a documentation of a diagnosis of medically intractable epilepsy as defined by the failure of at least 2 appropriately dosed and tolerated AEDs to eliminate all clinical seizures over a 6 month period (prior to epilepsy surgery). 3. The patient has a documentation of resective epilepsy surgery following appropriate presurgical evaluation. 4. The patient has a documentation of continued clinical seizures that persist at least 3 months following resective epilepsy surgery. At the time of treatment, to proceed with drug administration, the patient has >8 seizures in the last 30 days without 2 weeks of seizure freedom. 5. The patient has a documentation that the subject is not a candidate for OR refuses any additional resective epilepsy surgery. 6. Patients have not been previously treated with a systemic mTOR inhibitor for epilepsy. Skin cream use with rapamycin or everolimus, however, is permitted. 7. The patient has adequate bone marrow function (ANC≥1,000/mm$^3$, platelet count of ≥100,000/mm$^3$, and hemoglobin ≥9 gm/dL), liver function (SGPT/ALT≤5 times ULN and bilirubin ≤5 times ULN), and renal function, defined as: Creatinine clearance or radioisotope GFR>/=70 mL/min/1.73 m$^2$ or a serum creatinine based on age/gender shown in Table 2 before starting therapy. 8. The patient has a fasting cholesterol level <350 mg/dL and triglycerides <400 mg/dL before starting therapy. In case one or both of these are exceeded, the patient can only be included after initiation of appropriate lipid lowering medication and documentation of cholesterol <350 mg/dL and triglycerides <400 mg/dl before start of therapy.

TABLE 2

| | Maximum Serum Creatinine (mg/dL) | |
|---|---|---|
| Age | Male | Female |
| 3 to <6 years | 0.8 | 0.8 |
| 6 to <10 years | 1 | 1 |
| 10 to <13 years | 1.2 | 1.2 |
| 13 to <16 years | 1.5 | 1.4 |
| >=16 years | 1.7 | 1.4 |

The threshold creatinine values in this table were derived from Schwartz formula for estimating GFR utilizing child length and stature data published by the CDC.

D. Patients with Surgically Refractory Epilepsy Treated with ABI-009

Participating patients were refractory to anti-epileptic medication and had continued seizures even after surgery to the brain.

Participating patients had a 4-week baseline observation period to obtain baseline seizure frequencies and rates. After the baseline period, participants were started on the assigned dose of ABI-009, given once weekly for a total of 3 weeks and the seizure frequencies and rates of seizures were measured. Any adverse events were noted and reported according to the NCI CTCAE v5.

Four patients were consented for the study. Patient 3 withdrew consent before starting the study hence data was available for 3 patients (Patients 1, 2 and 4). Three patients received ABI-009 at a dose of 5 mg/m$^2$ given by IV push, within 3 minutes, once weekly for 3 weeks.

The Efficacy results are tabulated below.

TABLE 3

| | Patient 1 | | |
|---|---|---|---|
| | Seizure Frequency/Week | % change in seizure frequency | % of Seizure Free days |
| Baseline 4 week period | 2.03 | 0% | 74% |
| Treatment week 3 | 0 | −100% | 100% |

TABLE 4

| | Patient 2 | | |
|---|---|---|---|
| | Seizure Frequency/Week | % change in seizure frequency | % of Seizure Free days |
| Baseline 4 week period | 10.84 | 0% | 42% |
| Treatment week 3 | 15 | 38% | 29% |

TABLE 5

| | Patient 4 | | |
|---|---|---|---|
| | Seizure Frequency/Week | % change in seizure frequency | % of Seizure Free days |
| Baseline 4 week period | 23.94 | 0% | 6% |
| Treatment week 3 | 6 | −75% | 71% |

Patient 1 is a 18 year old male with Cortical dysplasia type 2A and type 2B. He had a relatively lower rate of seizures at baseline (average of ~2 seizures/week). Following treatment with ABI-009 for 3 weeks, no seizures were observed and the % of seizure-free days increased from 74% to 100%.

Patient 2 is a 15 year old female with Cortical dysplasia within left frontal regions. She had a medium rate of seizures at baseline (average of ~11 seizures/week). Following treatment with ABI-009 for 3 weeks, the frequency of seizures was not decreased.

Patient 4 is a 12 year old male with Intractable infantile spasms and left-sided congenital hemiparesis. He had a high rate of seizures at baseline (average of ~24 seizures/week). Following treatment with ABI-009 for 3 weeks, the frequency of seizures was decreased by 75% and the % of seizure-free days increased from 6% to 71%.

Thus, 2 out of 3 patients that were refractory to both surgery and antiepileptic medications responded to treatment with ABI-009. Currently there is no approved treatment for these patients.

Safety: Adverse events related to the drug were mild (all Grade 1) and included increased aspartate aminotransferase, eosinophilia, diarrhea, myalgia, and decrease in platelet count.

Example 4: Rapamycin Distribution to Different Organs Following a Single Intravenous Administration of ABI-009

This example describes rapamycin distribution to different organs including brain following a single intravenous administration of ABI-009 in rodents.

In this study, female SD rats received a single intravenous dose of ABI-009 at 1.7, 9.5, and 17 mg/kg with a 10 ml/kg dosing volume. At 2, 8, 24, 72, and 120 hours following administration, whole blood and organ samples were collected from 3 animals at each ABI-009 dose. Whole blood was collected into pre-chilled K2EDTA tubes and stored at −80° C., whereas brain, heart, liver, lung, and pancreas were collected, flushed with saline to remove the blood, divided into 2 portions, flash frozen in individually labeled tubes, and stored at −80° C.

All tissue samples were weighed and homogenated after adding solvent at ratio of 5 ml of homogenate solvent for each gram of tissue before analysis. Rapamycin was extracted from lysed whole blood or tissue homogenate by protein precipitation using 50:50 methanol:zinc sulfate. Tacrolimus was added as internal standard prior to the extraction.

After vortexmixing and centrifugation, a portion of the supernatant was transferred to a clean plate and injected into an LC-MS/MS system using a Synergi Polar-RP column with a gradient ammonium acetate/water/formic acid/acetonitrile mobile phases. Detections were made by MS-MS monitoring of positive ions produced with Sciex API5000.

Rapamycin concentrations in blood, brain, heart, liver, lung, and pancreas are listed in FIG. 3.

Figure 1:
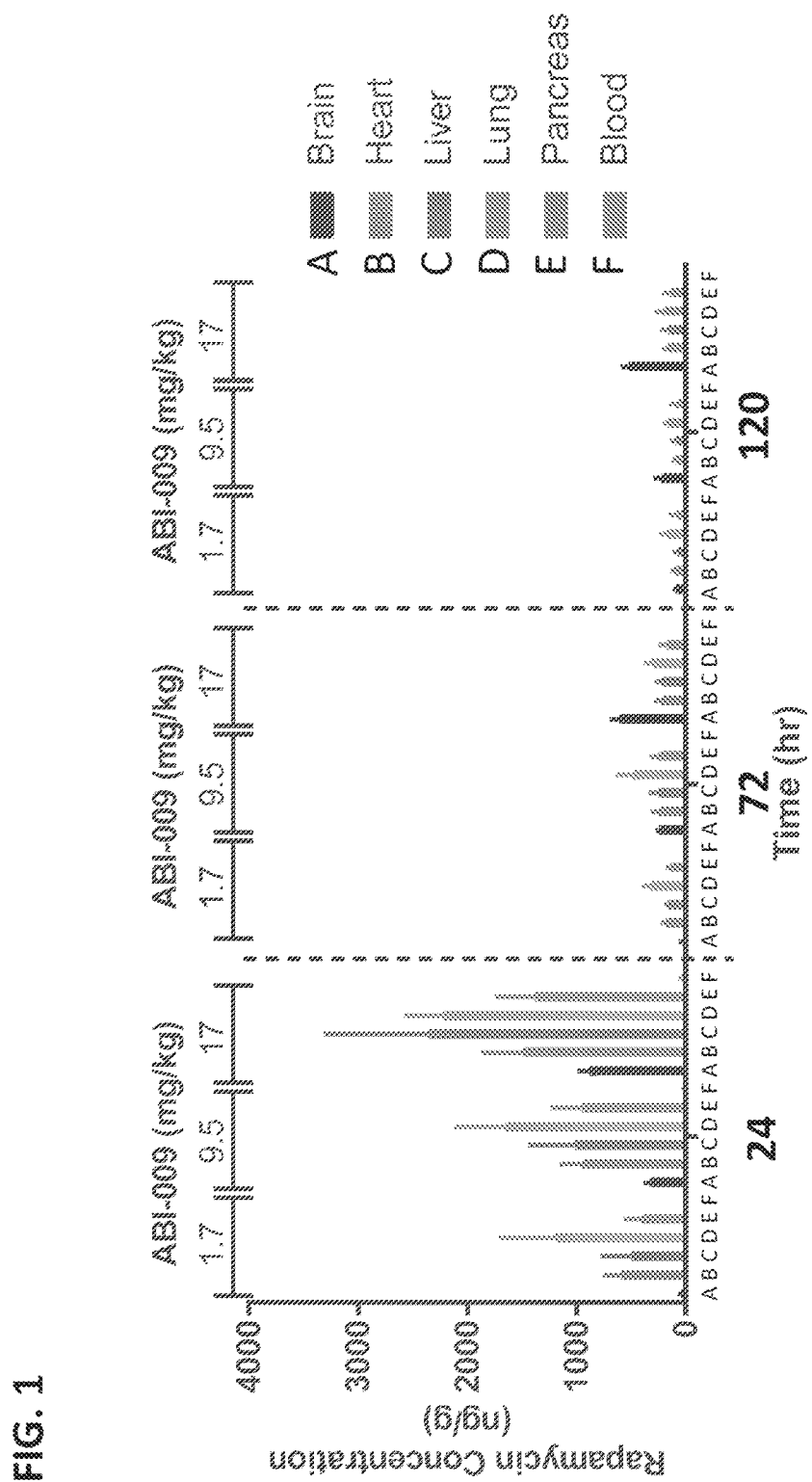
FIG. 1 provides rapamycin concentrations in brain, heart, liver, lung, pancreas, and blood at 24 hours, 72 hours and 120 hours following intravenous administration of three different doses (1.7 mg/kg, 9.5 mg/kg, and 17 mg/kg) of ABI-009 into rats.

There was a rapid decline of blood rapamycin levels between 2 hours and 24 hours following a single ABI-009 IV dosing. At these earlier time points, there were increasing blood rapamycin levels with higher ABI-009 doses, in a largely dose-proportional manner. After 72 hours, there were only trace amount of rapamycin in the blood, with no difference observed among different ABI-009 dose groups (FIG. 1).

Figure 2:
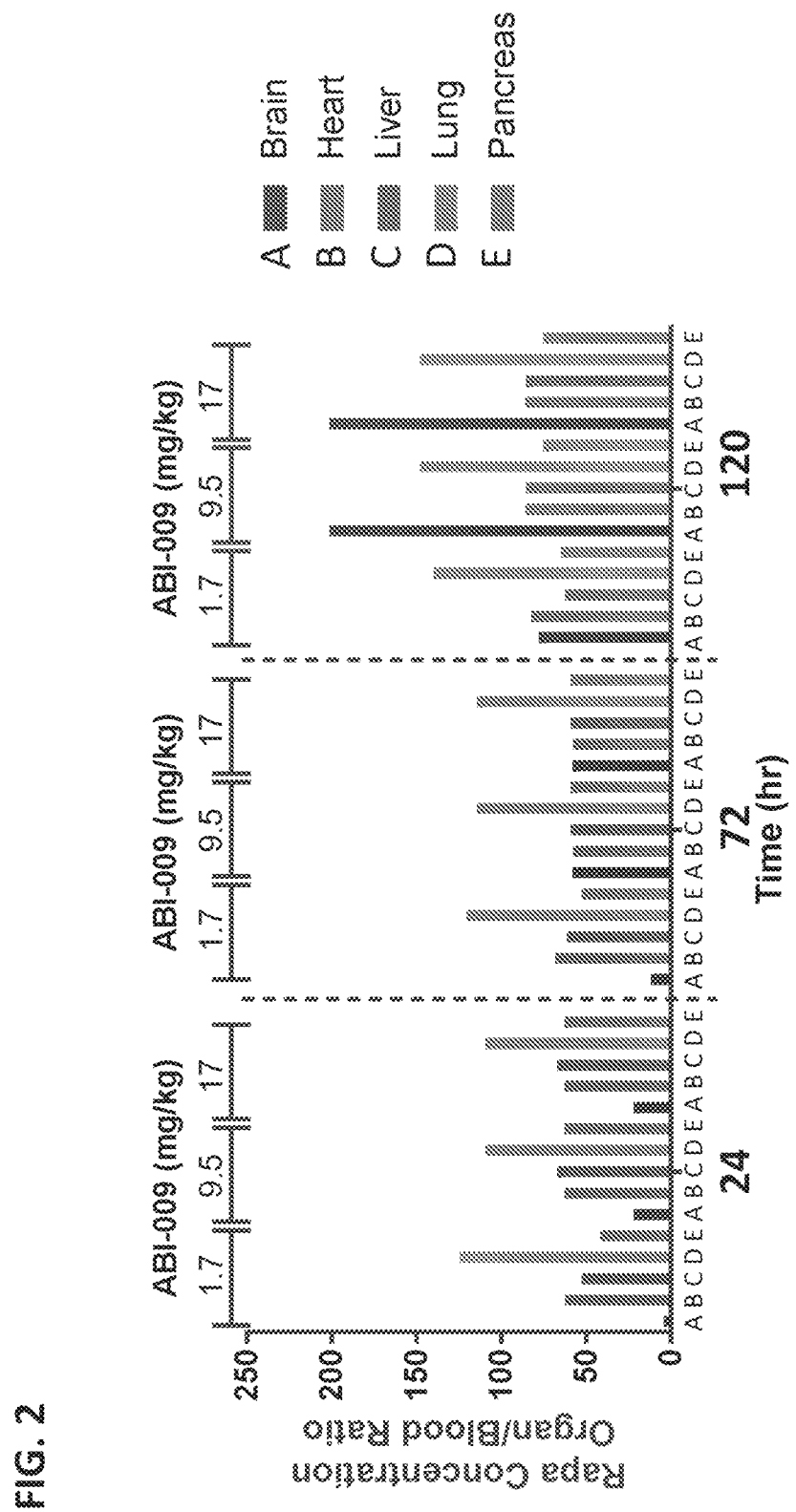
FIG. 2 provides the ratios of rapamycin concentrations in different organs (brain, heart, liver, lung, and pancreas) to rapamycin concentrations in blood at 24 hours, 72 hours and 120 hours following intravenous administration of three different doses (1.7 mg/kg, 9.5 mg/kg, and 17 mg/kg) of ABI-009 into rats.

In well-perfused organs including heart, liver, lung, and pancreas, the rapamycin concentration profiles were similar to that of the blood, with high peaks at earlier time points that dropped quickly with time between 2 hours and 24 hours. In contrast with the blood, significant levels of rapamycin remained in heart, liver, lung, and pancreas after 72 and 120 hours, demonstrating that these organs can retain therapeutic levels of rapamycin long after ABI-009 IV administration and supporting the dosing of ABI-009 once weekly or even less frequently for the treatment of disease conditions in these organs (FIG. 1). At all time points, there was a high organ/blood ratio of rapamycin concentrations, demonstrating effective extraction of rapamycin from blood and distribution into organs with ABI-009 (FIG. 2). At earlier time points of 2, 8 and 24 hours, there were increasing rapamycin levels with higher ABI-009 doses in the well-perfused organs, in a largely dose-proportional manner. After 72 hours, rapamycin levels in these organs were similar among different ABI-009 dose groups.

In contrast to well-perfused organs, rapamycin concentrations in the brain were relatively low at 2 hours but maintained at a steady level over time. The lower initial distribution into the brain is presumably due to the presence of the blood brain barrier. After 5 days, rapamycin level in the brain was similar or higher compared with other organs, suggesting substantial and prolonged drug distribution to the brain with ABI-009. With the drop in blood rapamycin levels, organ/blood ratios of most organs increase with time; however, the brain/blood rapamycin concentration ratios increase most significantly over time. Also in contrast to other organs, rapamycin levels in the brain and brain/blood ratios also increased with higher initial dose of ABI-009 at all time points, especially after 72 hours and 120 hours. In summary, the brain distribution profile after a single IV ABI-009 dosing is significantly different from other organs. ABI-009 IV administration results in significant and steady rapamycin concentrations well over the required minimum therapeutic levels of 5-20 ng/ml for mTOR inhibitors in the brain over prolonged time. Results from this PK study strongly support the treatment of different disease conditions in the brain with ABI-009 IV administration once weekly or even less frequently, and prove that higher sustainable rapamycin levels in the brain can be achieved with a higher initial ABI-009 dose.

Unexpected findings of this study include the following.

There was an initial rapid decrease in tissue level of rapamycin in the first 24 hours for all organs except the brain that showed a fairly flat or increasing tissue level.

The dose response for tissue levels was seen only in the first 24 hours. At 72 hours and thereafter, there was no observable dose response in all tissues except the brain.

These data suggested the brain slowly accumulated the drug over 120 hours whereas all the other tissues rapidly cleared the drug after 24 hours.

Tissue levels for all organs except the brain followed the blood clearance profile of rapamycin. This was further supported by observing the tissue/blood ratio of rapamycin over the period of the experiment. The tissue/blood ratios for all tissues except the brain remained fairly constant over 120 hours. In contrast, the brain/blood ratio increased over the same time period.

There was a preferential accumulation of rapamycin into the brain with the highest tissue extraction ratio for any of the organs seen at 120 hours.

At all times and all doses, tissue levels of rapamycin in the brain were well above the threshold of 5-20 ng/ml (or ng/g) which is required for therapeutic activity.

Preclinical studies have shown that other mTOR inhibitors, everolimus and temsirolimus have poor brain penetration, limiting their potential use for the treatment of disease conditions in the brain. In contrast, ABI-009 IV administration can achieve brain rapamycin concentration well above the required minimum therapeutic level of 5-20 ng/ml.

The brain was the only tissue that showed a dose response for tissue levels after at 120 hours (5 days) after administration. For all other organs, no significant differences in rapamycin concentrations were observed after 72 hours with different initial ABI-009 doses.

These results also support that high ABI-009 doses may be desirable to achieve improved clinical benefits for the treatment of disease conditions in the brain.

Example 5: Pharmacokinetics Study Following Subcutaneous and Intravenous Dosing of ABI-009 in Sprague Dawley (SD) Rats Female SD rats received a single dose of nab-rapamycin (ABI-009) subcutaneously (i.e., "SC" or "subQ") or intravenously (IV). The study design is summarized below in Table 6. No inflammation or toxicity was observed after administration at the subcutaneous injection sites at any time point compared with the saline control (vehicle).

TABLE 6

Study Design of Single Dose of ABI-009 in Rats

| Group | No. mice | Test material | Route of administration | Dose | | Euthanasia time point (hours) |
|---|---|---|---|---|---|---|
| 1 | 3 | vehicle | SC | 0.5 | ml/kg | 168 |
| 2 | 3 | ABI-009 | SC | 0.56 | mg/kg | 24 |
| 3 | 3 | ABI-009 | SC | 0.56 | mg/kg | 168 |
| 4 | 3 | ABI-009 | SC | 1.7 | mg/kg | 24 |
| 5 | 3 | ABI-009 | SC | 1.7 | mg/kg | 168 |
| 6 | 3 | ABI-009 | SC | 5 | mg/kg | 24 |
| 7 | 3 | ABI-009 | SC | 5 | mg/kg | 168 |
| 8 | 3 | ABI-009 | SC | 9.5 | mg/kg | 24 |
| 9 | 3 | ABI-009 | SC | 9.5 | mg/kg | 168 |
| 10 | 3 | ABI-009 | IV | 1.7 | mg/kg | 24 |
| 11 | 3 | ABI-009 | IV | 1.7 | mg/kg | 168 |

Figure 4:
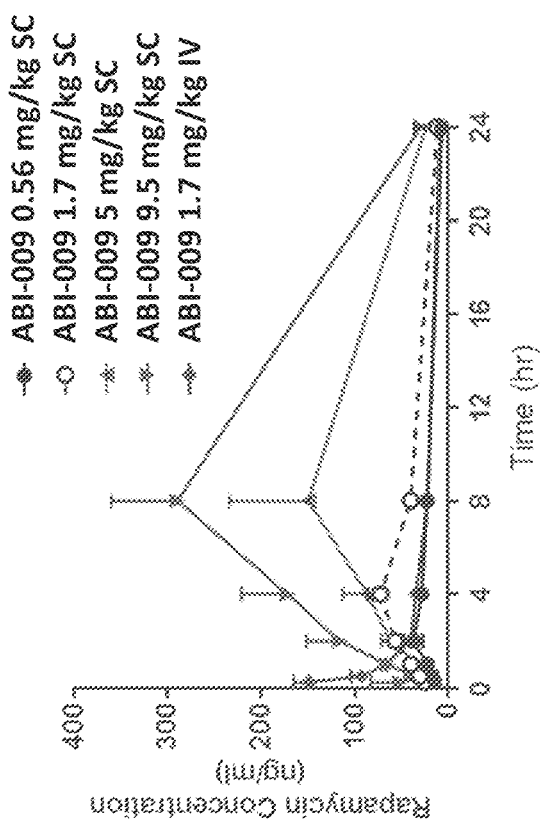
FIG. 4 shows rapamycin concentrations in whole blood samples taken from rats after subcutaneous (SC) or intravenous (IV) administration of a single dose of nab-rapamycin (ABI-009) between 0 and 24 hours after administration.
Figure 5:
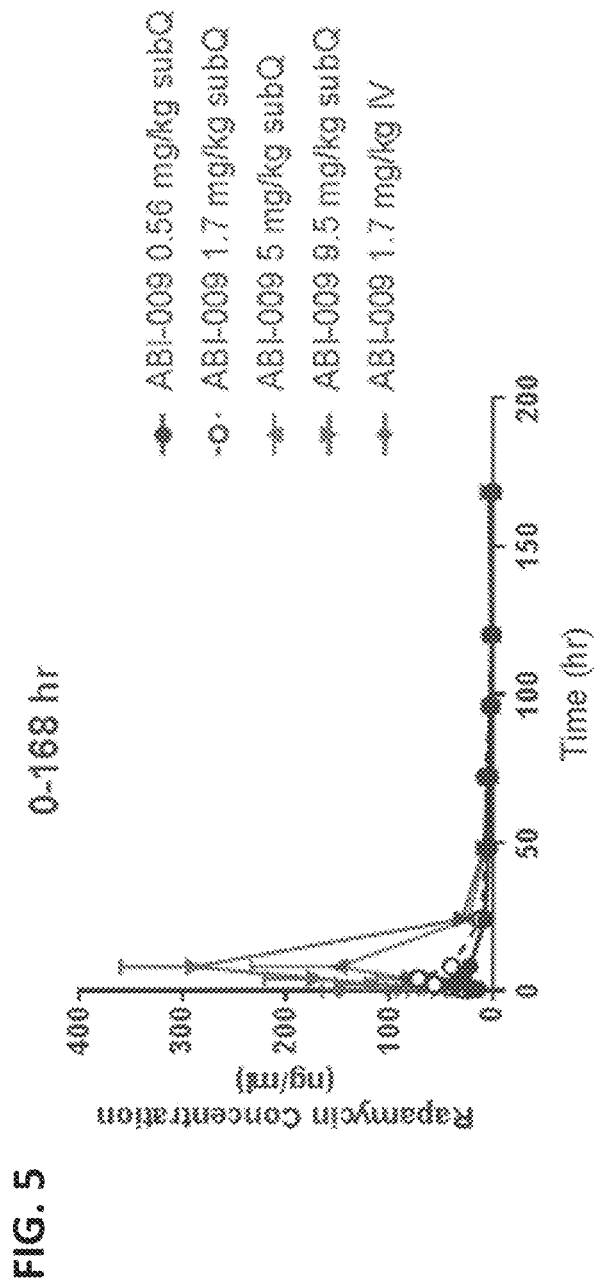
FIG. 5 shows rapamycin concentrations in whole blood samples taken from rats after subcutaneous (SC) or intravenous (IV) administration of a single dose of nab-rapamycin (ABI-009) between 0 and 168 hours after administration.
Figure 6:
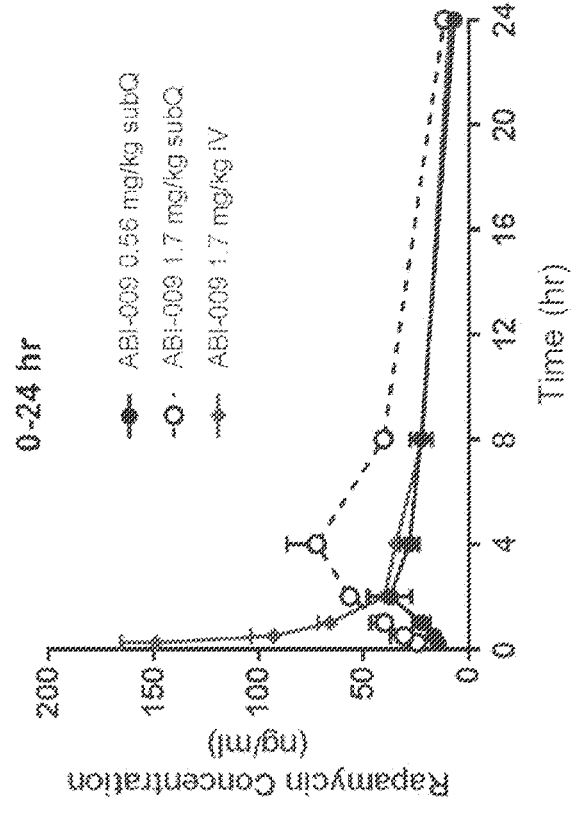
FIG. 6 shows rapamycin concentrations in whole blood samples taken from rats after subcutaneous (SC) or intravenous (IV) administration of a single dose of nab-rapamycin (ABI-009) between 0 and 24 hours after administration.

After subcutaneous or intravenous injection of ABI-009, rapamycin concentrations in the whole blood were measured at different time points. The results of the whole blood collections are shown in FIGS. 4-6 and summarized in Tables 7 and 8 below.

Further, subcutaneous administration reduced the maximum concentration achieved (Cmax) and delayed the time to reach the maximum concentration (Cmax time). Rapamycin peak levels and AUC in blood increased with higher subcutaneous ABI-009 doses.

TABLE 7

Rapamycin Concentration after ABI-009 Administration

| Time | ABI-009 0.56 mg/kg SC | | | ABI-009 1.7 mg/kg SC | | | ABI-009 5 mg/kg SC | | |
|---|---|---|---|---|---|---|---|---|---|
| (hr) | Average | SD | N | Average | SD | N | Average | SD | N |
| 0.25 | 14.70 | 3.66 | 3 | 24.63 | 4.74 | 3 | 21.40 | 5.39 | 3 |
| 0.5 | 16.77 | 3.66 | 3 | 30.93 | 6.37 | 3 | 19.20 | 6.92 | 3 |
| 1 | 22.53 | 4.27 | 3 | 40.23 | 6.55 | 3 | 30.17 | 5.91 | 3 |
| 2 | 37.40 | 10.02 | 3 | 56.67 | 1.62 | 3 | 61.73 | 9.81 | 3 |
| 4 | 28.37 | 4.58 | 3 | 72.60 | 14.10 | 3 | 86.60 | 26.54 | 3 |
| 8 | 22.70 | 5.22 | 3 | 40.57 | 3.56 | 3 | 149.70 | 84.47 | 3 |
| 24 | 6.95 | 1.29 | 3 | 11.80 | 1.80 | 3 | 24.17 | 11.65 | 3 |
| 48 | 4.13 | 1.10 | 3 | 5.75 | 0.80 | 3 | 6.87 | 2.04 | 3 |
| 72 | 4.57 | 3.51 | 3 | 7.32 | 5.96 | 3 | 3.59 | 0.27 | 3 |
| 96 | 1.89 | 0.52 | 3 | 2.37 | 0.80 | 3 | 1.80 | 0.54 | 3 |
| 120 | 1.40 | 0.44 | 3 | 1.75 | 0.60 | 3 | 1.48 | 0.29 | 3 |
| 168 | 1.01 | 0.28 | 3 | 1.18 | 0.19 | 3 | 0.90 | 0.39 | 3 |

TABLE 8

Rapamycin Concentration after ABI-009 Administration

| Time | ABI-009 9.5 mg/kg SC | | | ABI-009 1.7 mg/kg IV | | |
|---|---|---|---|---|---|---|
| (hr) | Average | SD | N | Average | SD | N |
| 0.25 | 51.70 | 31.20 | 3 | 149.00 | 16.64 | 3 |
| 0.5 | 37.83 | 8.17 | 3 | 93.00 | 10.75 | 3 |
| 1 | 64.93 | 7.43 | 3 | 66.30 | 5.48 | 3 |
| 2 | 116.27 | 36.19 | 3 | 40.07 | 8.59 | 3 |
| 4 | 171.67 | 49.57 | 3 | 34.80 | 0.85 | 3 |
| 8 | 289.33 | 70.88 | 3 | 22.13 | 3.86 | 3 |
| 24 | 30.03 | 4.82 | 3 | 8.85 | 1.46 | 3 |
| 48 | 8.93 | 1.20 | 3 | 4.66 | 1.53 | 3 |
| 72 | 5.09 | 2.08 | 3 | 2.95 | 0.85 | 3 |
| 96 | 2.58 | 0.84 | 3 | 1.78 | 0.42 | 3 |
| 120 | 1.76 | 0.44 | 3 | 1.39 | 0.36 | 3 |
| 168 | 4.09 | 5.06 | 3 | 0.87 | 0.30 | 3 |

Figure 7:
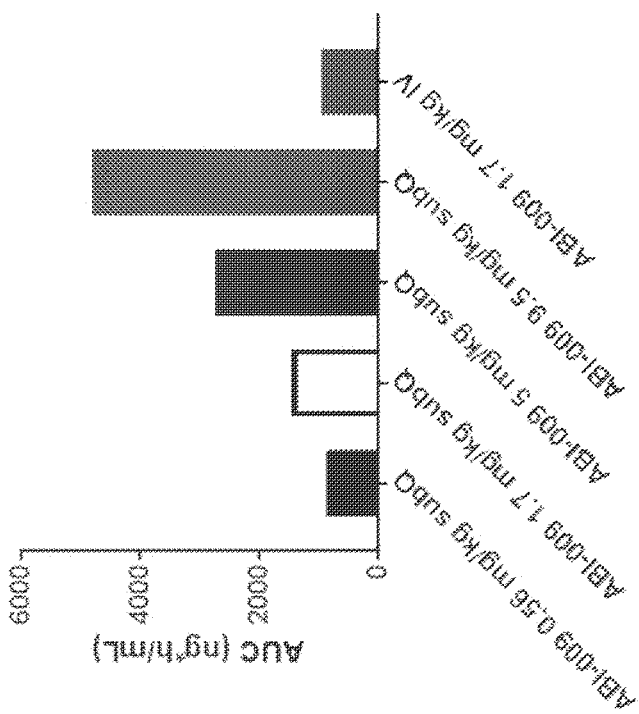
FIG. 7 shows the bioavailability of nab-rapamycin (ABI-009) after subcutaneous (subQ) or intravenous (IV) administration of a single dose in rats as indicated by the calculated area under the curve (AUC).

Surprisingly, as summarized in FIG. 7 and Table 9, below, subcutaneous administration enhanced bioavailability as indicated by total area under the curve (AUC) compared with intravenous administration. Subcutaneous administration of only 0.56 mg/kg ABI-009 produced similar drug exposure at ⅓rd the dose of IV ABI-009 (1.7 mg/kg).

TABLE 9

Pharmacokinetics of ABI-009 Administration in Rats

| Route | SC | SC | SC | SC | IV |
|---|---|---|---|---|---|
| Dose (mg/kg) | 0.56 | 1.7 | 5 | 9.5 | 1.7 |
| Cmax (ng/mL) | 37.40 | 72.60 | 149.70 | 289.33 | 149.00 |
| Cmax Time (h) | 2 | 4 | 8 | 8 | 0.25 |
| AUC (ng*h/mL) | 860.8 | 1451 | 2734 | 4813 | 962.6 |

Example 6: Biodistribution of ABI-009 after Administration in Rats

Figure 8:
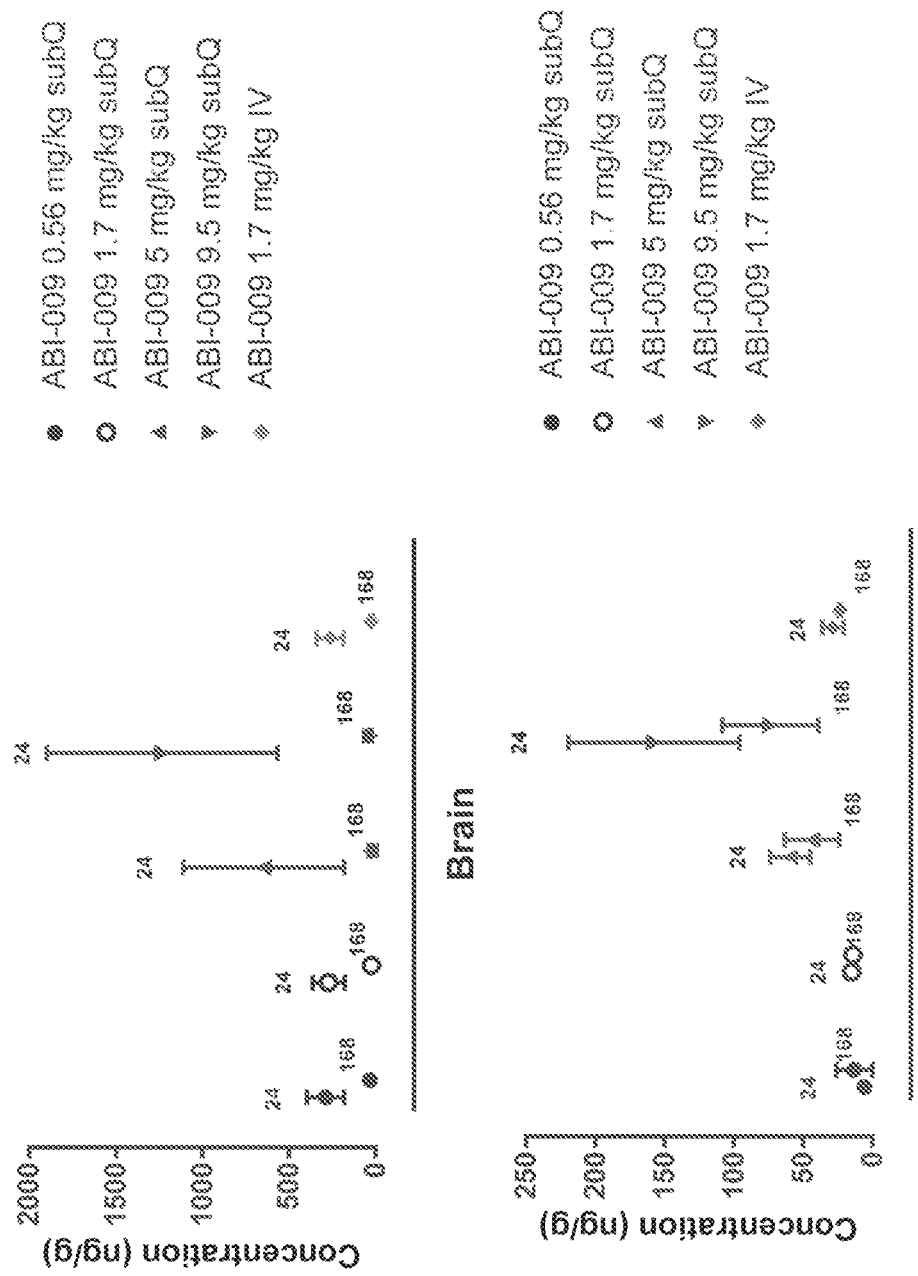
FIG. 8 shows the concentration of rapamycin in rat bone marrow (top) or brain (bottom) 24 or 168 hours after subcutaneous (subQ) or intravenous (IV) administration of a single dose of nab-rapamycin (ABI-009).
Figure 9:
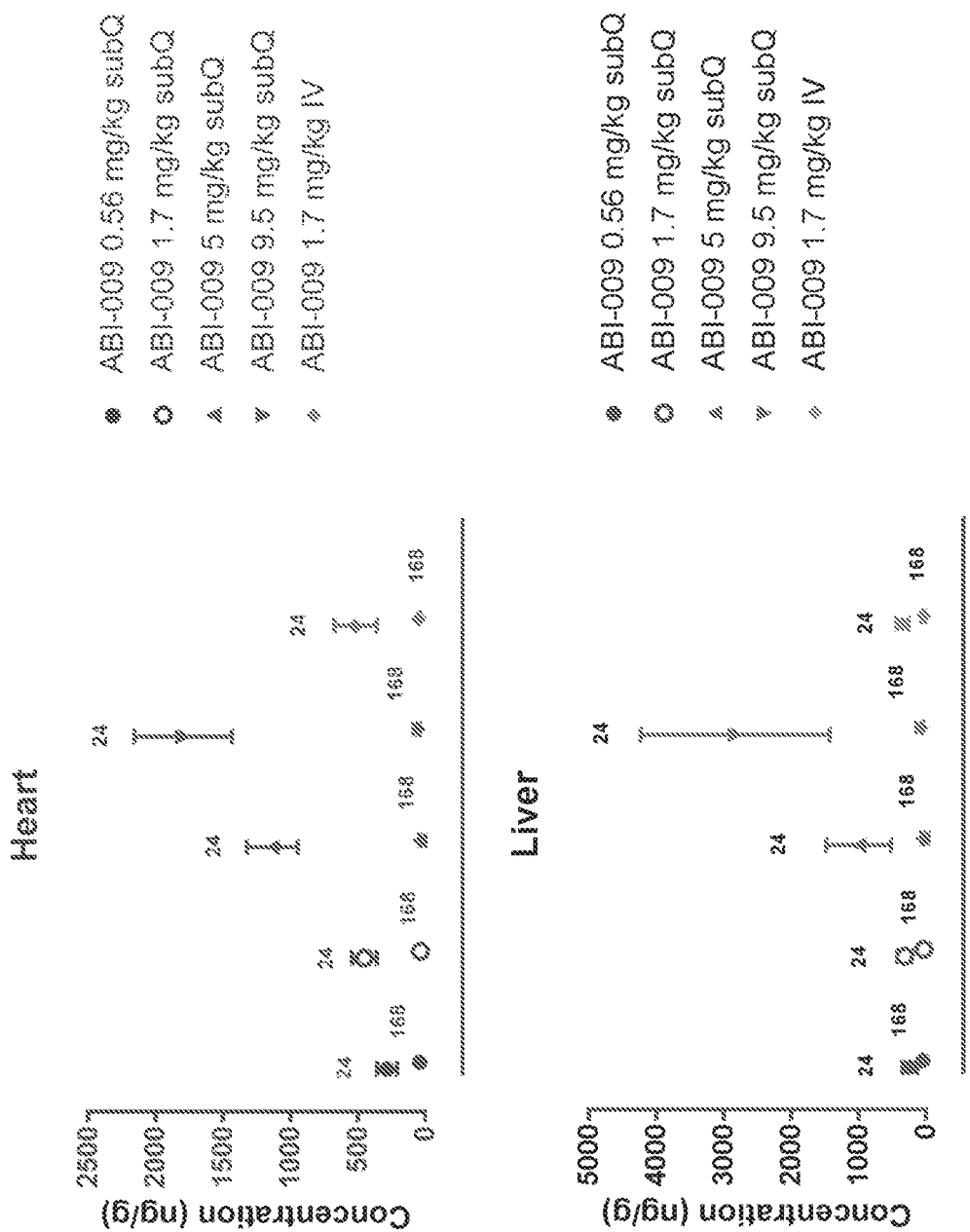
FIG. 9 shows the concentration of rapamycin in rat heart (top) or liver (bottom) 24 or 168 hours after subcutaneous (subQ) or intravenous (IV) administration of a single dose of nab-rapamycin (ABI-009).
Figure 10:
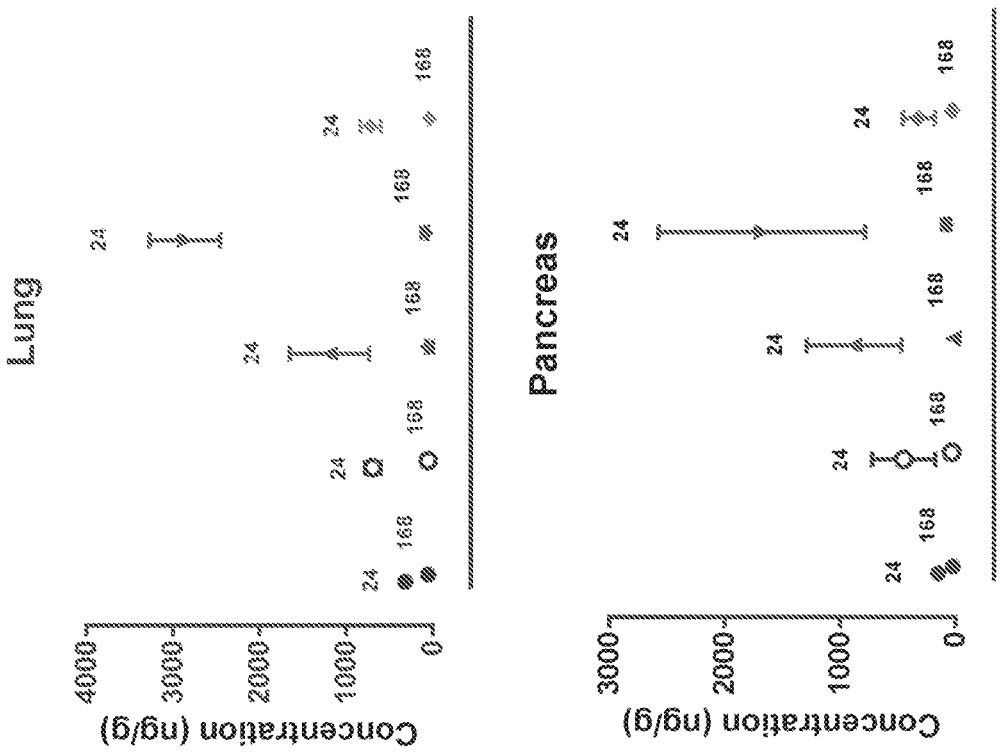
FIG. 10 shows the concentration of rapamycin in rat lung (top) or pancreas (bottom) 24 or 168 hours after subcutaneous (subQ) or intravenous (IV) administration of a single dose of nab-rapamycin (ABI-009).

Tissues were harvested from the rats described above in Example 5 at either 24 hours or 168 hours (see Table 6 for study design) post-administration by subcutaneous (subQ) or intravenous (IV) route of ABI-009. The concentration of rapamycin in particular rat tissues 24 or 168 hours post-administration is indicated in FIG. 8 (bone marrow and brain), FIG. 9 (heart and lung), and FIG. 10 (lung and pancreas).

The subcutaneous route of administration resulted in significant distribution to all organs tested, including bone marrow, brain, heart, liver, lung, and pancreas. The pattern of organ distribution was similar between subcutaneous and intravenous but subcutaneous administration at 0.56 mg/kg dose was able to produce similar tissue concentrations as intravenous administration at 1.7 mg/kg dose. There was a significant drop in rapamycin concentration between 24 and 168 hours in well-perfused organs including the heart, liver, lung, and pancreas. However, the brain concentration was relatively stable between 24 and 168 hours.

Figure 11:
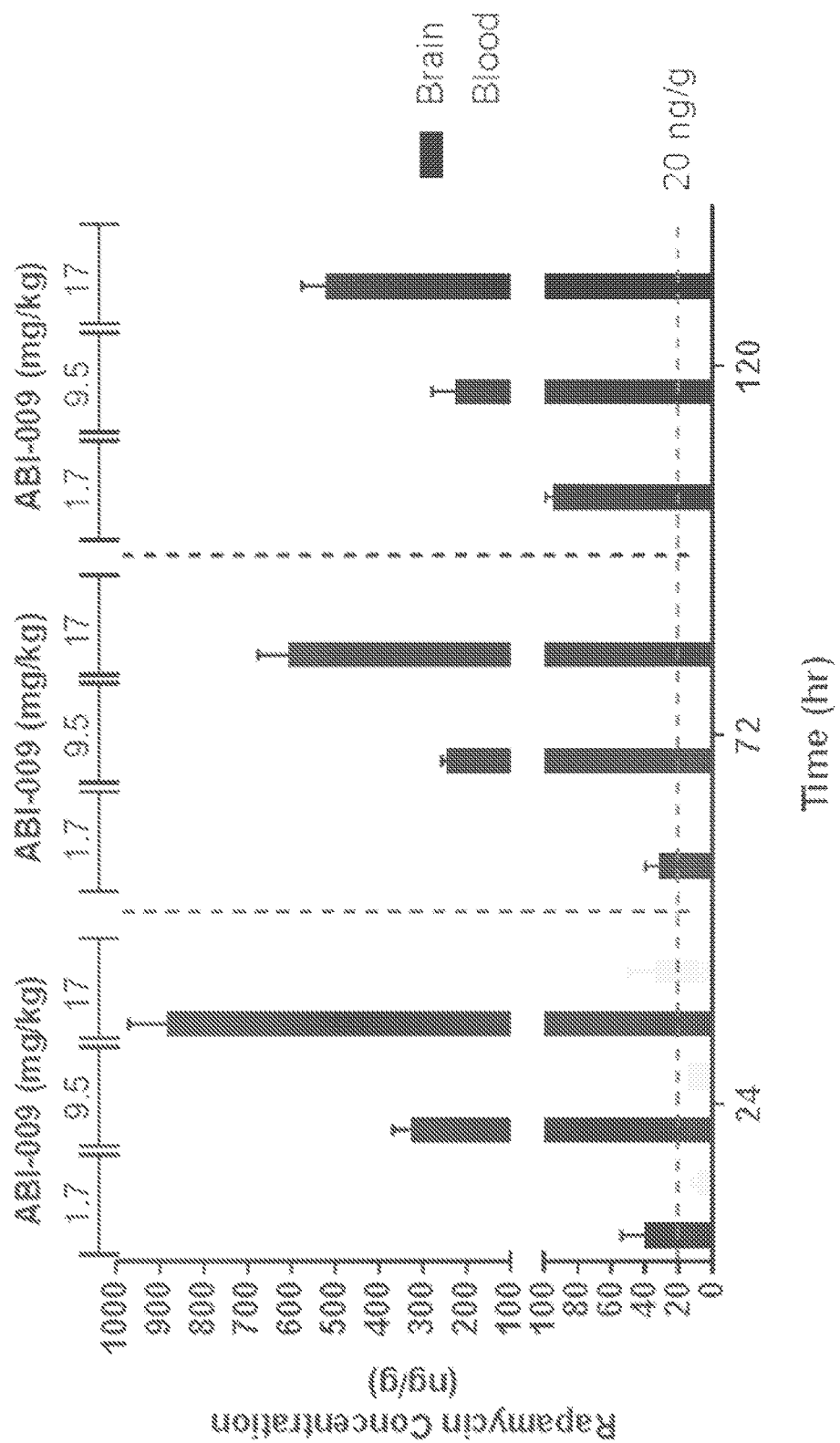
FIG. 11 shows a comparison of rapamycin concentrations over time in brain or whole blood from rats after 24, 72, and 120 post-administration of a single subcutaneous dose of nab-rapamycin (ABI-009) at a dose of 1.7 mg/kg, 9.5 mg/kg or 17 mg/kg.

To further clarify the difference between brain and blood distribution of rapamycin, a further experiment was conducted with rats. Rats were subcutaneously administered a single dose of nab-rapamycin (ABI-009) at a dose of 1.7 mg/kg, 9.5 mg/kg, or 17 mg/kg. Mice were sacrificed at 24, 72, and 120 hours and whole blood and brain tissue were collected. Rapamycin concentrations were measured at each time points for each sample. As indicated in FIG. 11, a dose-dependent increase in brain rapamycin levels was observed. Surprisingly, while blood levels of rapamycin rapidly approached baseline, even at the high 17 mg/kg dose, brain rapamycin levels were well-maintained over the entire 120 hours, even at the lowest dose.

Example 7: Toxicology Study Following Repeated Subcutaneous Dosing of ABI-009 in SD Rats The objectives of the study were to assess the overall safety and local toxicity at injection sites following repeated ABI-009 SC injections in SD rats. The signs of clinical distress were observed to determine toxicity. Skin samples from the injection sites were analyzed for signs of inflammation and necrosis by histopathology.

Fifteen female Sprague Dawley (SD) rats weighing 160-180 g were used in the study. ABI-009 was dissolved in saline to prepare a stock solution (10 mg/ml), then further diluted in HSA 0.9% saline solution to prepare subcutaneous (volume: 1.0 ml/kg).

A. Study Design

Rats were divided into 5 groups of 3 animals each. Rats were weighed and dosed SC as specified in Table 10 every 4 days for 4 weeks (7 injections).

TABLE 10

Treatment Groups

| Group | Number of Rats | Test articles | ROA | Dose | Dose volume | Schedule |
|---|---|---|---|---|---|---|
| 1 | 3 | 0.9% Saline | SC | — | 1.0 ml/kg | Once every 4 days for 4 weeks |
| 2 | 3 | HSA in 0.9% Saline | SC | 90 mg HSA/kg | | |
| 3 | 3 | ABI-009 | SC | 1.7 mg/kg | | |
| 4 | 3 | ABI-009 | SC | 5 mg/kg | | |
| 5 | 3 | ABI-009 | SC | 10 mg/kg | | |

SC = subcutaneous injection

Animals were examined daily for clinical signs of overall toxicity and the local injection sites examined for reactions to subcutaneous injection.

Whole blood samples were collected prior to each injection for animals receiving ABI-009 (Groups 3, 4, and 5) and analyzed for trough sirolimus levels.

All animals were euthanized after 4 weeks and skin samples from local injection sites were examined by histopathology for signs of local toxicity.

B. Experiment Procedures

1. Dosing Solution Preparation

Vehicle controls consist of 0.9% saline solution and HSA in 0.9% saline solution. Final concentration of HSA solution is 90 mg/ml, based on the albumin:sirolimus ratio of 9:1 of the test article ABI-009 (manufacture lot #C345-001, Fisher lot #51394.2). Each vial of ABI-009 (C345-001) contains 97.4 mg sirolimus and 874 mg human albumin. HSA saline solution is diluted from 20% Grifols albumin stock solution (200 mg/ml).

For ABI-009 dosing solutions, first make a stock ABI-009 solution of 10 mg/ml, then dilute to desired concentrations for dosing solution using HSA-saline solution. A vial of 100 mg of ABI-009 was dissolved in 10 ml of 0.9% saline to prepare a solution of 10 mg/ml.

ABI-009 solution of 5 mg/ml was prepared by diluting 0.6 ml of stock solution (10 mg/ml) with 0.6 ml of HSA-0.9% saline to prepare a solution of 5.0 mg/ml for group 4. ABI-009 solution of 1.7 mg/ml was prepared by diluting 0.3 ml of ABI-009 solution from group 4 (5.0 mg/ml) with 0.6 ml of HSA-0.9% saline to prepare a solution of 1.7 mg/ml for group 3.

2. Dosing

The rats were anesthetized, weighed, and administered with ABI-009 solutions, HSA solution and saline according to Table 11 by subcutaneous (SC) injection every 4 days for 4 weeks (7 injections).

TABLE 11

Dosing volume

| Group | Test articles | ROA | Dose (mg/kg) | Dosing Sol (mg/ml) | Dose Volume (ml/kg) |
|---|---|---|---|---|---|
| 1 | 0.9% Saline | SC | 0 | 0 | 1.0 |
| 2 | HSA in 0.9% Saline | SC | 0 (90 mg HSA) | 0 (90 mg HSA) | 1.0 |
| 3 | ABI-009 | SC | 1.7 | 1.7 | 1.0 |
| 4 | ABI-009 | SC | 5 | 5 | 1.0 |
| 5 | ABI-009 | SC | 10 | 10 | 1.0 |

Rats were examined once daily for clinical signs of overall toxicity and the local injection sites for reactions to subcutaneous injection. The signs of clinical distress were observed to determine toxicity. Piloerection, weight loss, lethargy, discharges, neurological symptoms, morbidity, redness and inflammation of injection site, and any other signs considered abnormal for animal behavior. Pictures of the injection site for all rats were taken before and after the SC injection.

3. Sample Collection and Analysis

For rats treated with ABI-009 (Groups 3, 4, and 5), rats were anesthetized and bled for samples into pre-chilled K2EDTA tubes before each administration (except 1st dose). Whole blood was collected, stored in labeled Eppendorf tubes at −80° C., and analyzed for trough sirolimus levels.

All animals were euthanized at the final euthanasia points of Day 29 (96 hrs post week 4 Day 25 ABI-009 administrations). At the final euthanasia time point, whole blood samples were collected for analysis of trough sirolimus level. The brain, lung, liver, heart, pancreas, and bone marrow were collected, flushed with saline to remove the blood, divided into 2 portions, and flash frozen in individually labeled tubes, and stored at −80° C. The frozen blood samples from ABI-009 treated groups (Groups 3, 4, and 5) are shipped on dry ice to BASi. Trough sirolimus blood levels were analyzed by BASi by LC/MS/MS method.

At the final euthanasia time point, skin and lower dermal layer at region of SC administration were excised for histological analysis by H&E staining for signs of inflammation by histopathology. Fifteen formalin-fixed rat skin samples were subject to histopathologic measurement and processed routinely. One slide from each block was sectioned and stained with hematoxylin and eosin (H&E). Slides were evaluated by a board-certified veterinary pathologist using light microscopy. Histologic lesions were graded for severity 0-5 (0=not present/normal, 1=minimal, 2=mild, 3=moderate, 4=marked, 5=severe). Mean scores of different groups were analyzed by t-test.

C. Results

1. Systemic Toxicity

The signs of clinical distress were observed daily to determine toxicity. Piloerection, weight loss, lethargy, discharges, neurological symptoms, morbidity, redness and inflammation of injection site, and any other signs considered abnormal for animal behavior. Rats were normal post dosing of saline, HSA, and AB-009 at current dose regimen (1.7-10 mg/kg, 7 doses), with no signs of clinic stress observed during the study.

There was no body weight loss (<20%), and all treatment groups gained weight during the study (Table 12). The results showed that rats tolerated subcutaneous injection of ABI-009 over a dose range of 1.7-10.0 mg/kg.

2. Local toxicity PU-3F

Fifteen formalin-fixed rat skin samples from the region of SC administration were subject to histopathologic measurement. Histopathologic findings in skin samples included necrosis and mixed infiltrates of inflammatory cells in perivascular zones; both lesions were observed in the subcutaneous tissues/subcutis.

Figure 12:
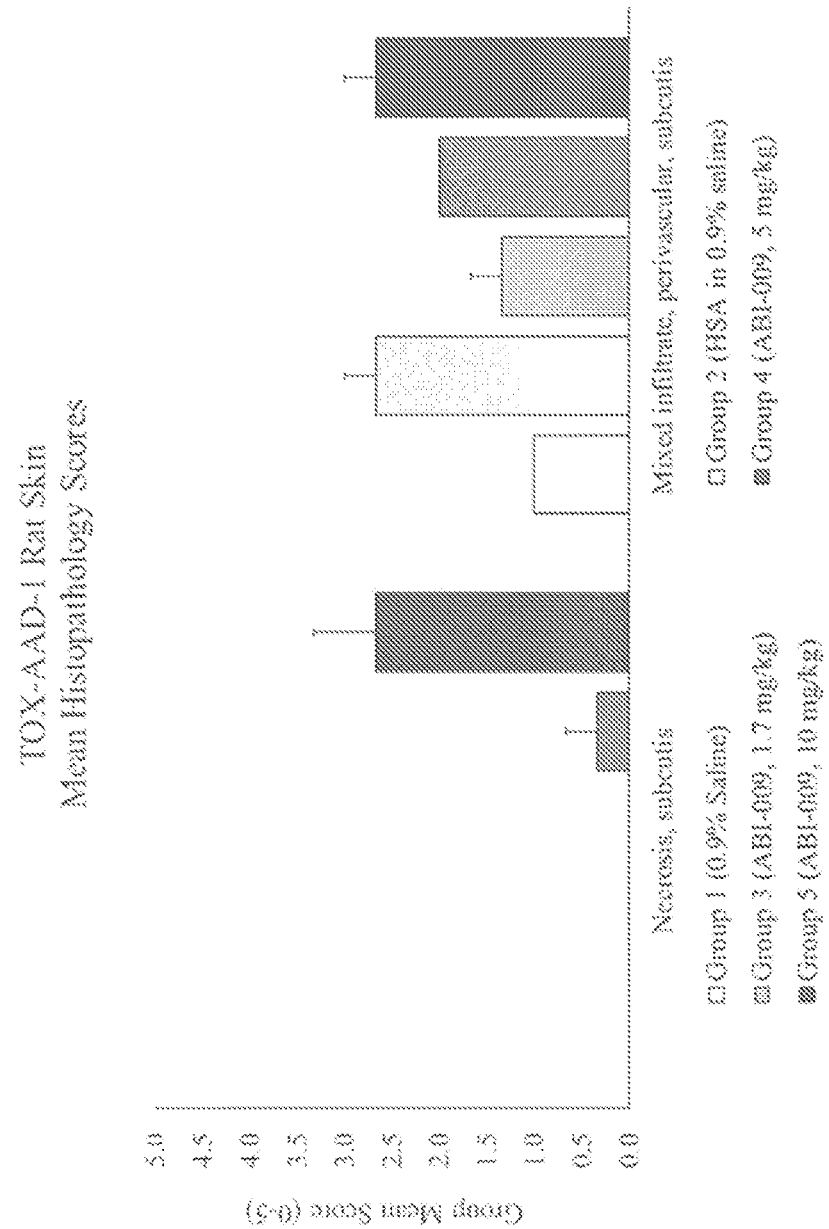
FIG. 12 shows a comparison of histopathology scores assessed on skins from rats among different treatment groups.
Figure 13:
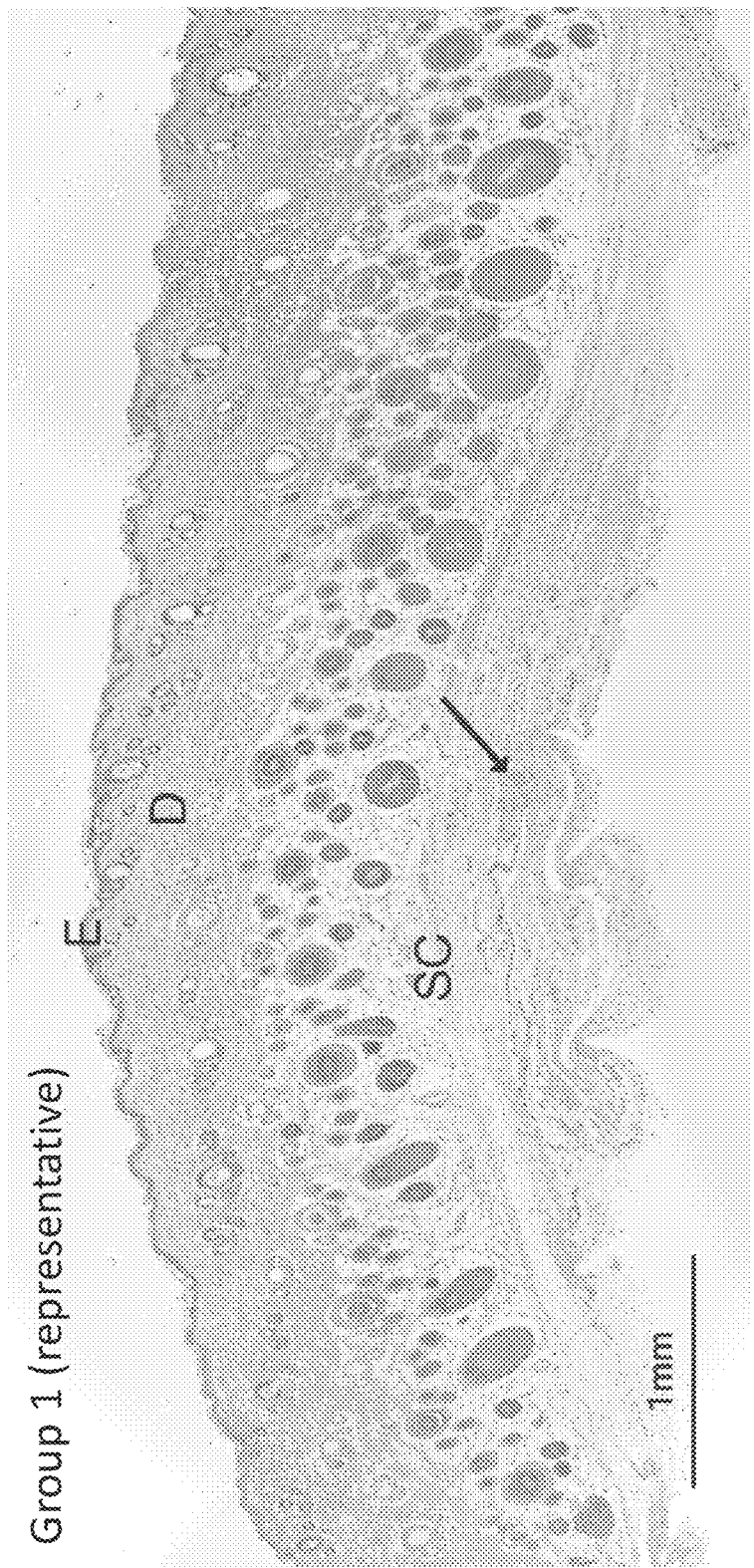
FIG. 13 is a representative histogram image of skin from rat in Group 1 (0.9% saline).

Necrosis was focal and characterized by a region of loss of normal cells, neutrophil infiltration, hemorrhage, and fibrin exudation, with variable adjacent fibroplasia. Necrosis was only observed in samples from animals treated with ABI-009 at 5 mg/kg (Group 4, 1 animal with minimal necrosis) and 10 mg/kg (Group 5, all 3 animals with mild to marked necrosis) dose levels, whereas saline (Group 1), HSA (Group 2), and AB-009 at 1.7 mg/kg (Group 3) caused no necrosis. See Table 13 and FIG. 12. Only AB-009 at the highest dose of 10 mg/kg showed significantly increased necrosis score compared with HSA group (P 0.02, t-test).

TABLE 12

Effect of Treatment on the Body Weight of Rats

| Groups | Mouse # | Body weight (g) | | | | | | |
| --- | --- | --- | --- | --- | --- | --- | --- | --- |
| | | Day 1 | Day 5 | Day 9 | Day 13 | Day 17 | Day 21 | Day 25 |
| Group 1 | 1 | 181 | 187 | 195 | 202 | 207 | 210 | 213 |
| 0.9% saline | 2 | 200 | 196 | 206 | 210 | 214 | 218 | 228 |
| 1 ml/kg | 3 | 187 | 191 | 193 | 201 | 204 | 209 | 219 |
| | average | 189 | 191 | 198 | 204 | 208 | 212 | 220 |
| | SD | 9.71 | 4.51 | 7.00 | 4.93 | 5.13 | 4.93 | 7.55 |
| Group 2 | 4 | 182 | 188 | 196 | 201 | 210 | 212 | 222 |
| HSA in 0.9% saline | 5 | 197 | 200 | 208 | 214 | 221 | 226 | 239 |
| 1 ml/kg | 6 | 173 | 180 | 188 | 199 | 207 | 211 | 216 |
| | average | 184 | 189 | 197 | 205 | 213 | 216 | 226 |
| | SD | 12.12 | 10.07 | 10.07 | 8.14 | 7.37 | 8.39 | 11.93 |
| Group 3 | 7 | 191 | 189 | 192 | 199 | 207 | 206 | 215 |
| ABI-009 | 8 | 186 | 189 | 186 | 193 | 199 | 200 | 209 |
| 1.7 mg/kg | 9 | 186 | 188 | 189 | 195 | 205 | 205 | 212 |
| | average | 188 | 189 | 189 | 196 | 204 | 204 | 212 |
| | SD | 2.89 | 0.58 | 3.00 | 3.06 | 4.16 | 3.21 | 3.00 |
| Group 4 | 10 | 195 | 193 | 192 | 196 | 200 | 199 | 208 |
| ABI-009 | 11 | 181 | 182 | 189 | 193 | 195 | 198 | 202 |
| 5 mg/kg | 12 | 196 | 197 | 190 | 195 | 204 | 202 | 208 |
| | average | 191 | 191 | 190 | 195 | 200 | 200 | 206 |
| | SD | 8.39 | 7.77 | 1.53 | 1.53 | 4.51 | 2.08 | 3.46 |
| Group 5 | 13 | 182 | 179 | 182 | 183 | 191 | 192 | 198 |
| ABI-009 | 14 | 188 | 180 | 187 | 189 | 193 | 198 | 197 |
| 10 mg/kg | 15 | 190 | 183 | 189 | 193 | 198 | 195 | 204 |
| | average | 187 | 181 | 186 | 188 | 194 | 195 | 200 |
| | SD | 4.16 | 2.08 | 3.61 | 5.03 | 3.61 | 3.00 | 3.79 |

TABLE 13

Effect of Treatment on the Body Weight of Rats

| Group | Sample | Necrosis, subcutis | Mixed infiltrate, perivascular, subcutis |
|---|---|---|---|
| Group 1 (0.9% Saline) | 1 | 0 | 1 |
|  | 2 | 0 | 1 |
|  | 3 | 0 | 1 |
|  | mean | 0.00 | 1.00 |
|  | SEM | 0.00 | 0.00 |
| Group 2 (HSA in 0.9% saline) | 4 | 0 | 2 |
|  | 5 | 0 | 3 |
|  | 6 | 0 | 3 |
|  | mean | 0.00 | 2.67 |
|  | SEM | 0.00 | 0.33 |
|  | p vs Grp 1 |  | 0.01 |
| Group 3 (ABI-009, 1.7 mg/kg) | 7 | 0 | 1 |
|  | 8 | 0 | 2 |
|  | 9 | 0 | 1 |
|  | mean | 0.00 | 1.33 |
|  | SEM | 0.00 | 0.33 |
|  | p vs Grp 2 |  | 0.05 |
| Group 4 (ABI-009, 5 mg/kg) | 10 | 0 | 2 |
|  | 11 | 1 | 2 |
|  | 12 | 0 | 2 |
|  | mean | 0.33 | 2.00 |
|  | SEM | 0.33 | 0.00 |
|  | p vs Grp 2 | 0.37 | 0.12 |
| Group 5 (ABI-009, 10 mg/kg) | 13 | 2 | 3 |
|  | 14 | 4 | 3 |
|  | 15 | 2 | 2 |
|  | mean | 2.67 | 2.67 |
|  | SEM | 1.00 | 0.00 |
|  | p vs Grp 2 | 0.02 | 1.00 |

Mixed inflammatory cell infiltration in subcuticular perivascular zones was characterized by infiltration and aggregation of lymphocytes, plasma cells, macrophages, occasional multinucleated giant cells, and variable numbers of neutrophils. Mixed inflammatory cell infiltration was observed in all treatment groups, with mean scores being the highest in animals treated with HSA (Group 2) and ABI-009 at 10 mg/kg (Group 5). For low dose ABI-009 injection at 1.7 mg/kg (Group 3), the mean score was similar to control group receiving saline injection (Group 1). See Table 13 and FIG. 12. High mixed inflammatory cell infiltration observed in the HSA group (Group 2) compared with saline control (P=0.01, t-test) suggests that local inflammation was largely caused by the injection of the heteroprotein human serum albumin.

Representative histology images for rats in each group were shown in FIGS. 13-17.

For ABI-009 treatment groups, there were dose-associated increases in local toxicities with increasing ABI-009 dose. At the lowest dose of ABI-009 1.7 mg/kg, the histology of local injection sites was similar to the saline control group; whereas necrosis and subcutaneous tissue inflammatory cell infiltration were the most severe in the ABI-009-treated animals at the 10 mg/kg dose level. 3. Trough sirolimus blood levels Trough sirolimus blood samples were collected before each injection (at Day 5, 9, 13, 17, 21, 25, 29) for groups treated with ABI-009 (except the $1^s$ dose on Day 1) and analyzed by BASi using LC/MS/MS method. Individual trough levels are shown in Table 14. Most trough sirolimus blood levels 4 days after SC injection were consistently in the range of 2-20 ng/ml. Two samples in the ABI-009 10 mg/kg group (Group 5) were clearly outliers. The reason for this observation cannot be ascertained. However, the abnormal high trough levels only occurred in the highest ABI-009 dose group that also showed mild to marked necrosis in the subcutaneous tissue, suggesting that skin lesions may hamper the normal absorption of ABI-009 and lead to prolonged drug retention.

TABLE 14

Trough Sirolimus Blood Levels

| Days/ID | Group 3 (ABI-009 1.7 mg/kg) | | | Group 4 (ABI-009 5 mg/kg) | | | Group 5 (ABI-009 10 mg/kg) | | |
|---|---|---|---|---|---|---|---|---|---|
|  | #3-7 | #3-8 | #3-9 | #4-10 | #4-11 | #4-12 | #5-13 | #5-14 | #5-15 |
| 5 | 3.1 | 2.38 | 2.56 | 4.5 | 3.63 | 6 | 3.28 | 8.37 | 4.54 |
| 9 | 5.56 | 7.91 | 4.16 | 6.42 | 4.57 | 7.67 | 19.1 | 19.3 | 4.64 |
| 13 | 2.92 | 3.1 | 3.35 | 18.3 | 5.97 | 9.8 | 4.9 | 6.64 | 3.87 |
| 17 | 4.02 | 13 | 2.04 | 1.58 | 3.64 | 9.7 | 11.4 | 6.79 | 14.8 |
| 21 | 0.24 | 1.69 | 3.39 | 3.44 | 3.63 | 4.8 | ALQ 201* | 6.83 | 5.27 |
| 25 | 5.32 | 2.18 | 3.06 | 7.03 | 4.5 | 19.7 | 3.28 | 8.34 | 5.6 |
| 29 | 3.04 | 3.17 | 2.77 | 5.1 | 3.64 | 9.03 | 4.34 | 4.69 | 92.8* |
| Mean |  | 3.760 |  |  | 6.793 |  |  | 7.683 |  |
| SEM |  | 0.5736 |  |  | 1.005 |  |  | 1.139 |  |

For each ABI-009 treatment group, there was no significant drug accumulation over the time course of the study, as trough blood sirolimus levels remained generally stable. There was a dose-dependent increase in mean trough blood sirolimus levels with increasing ABI-009 dose. Compared with ABI-009 1.7 mg/kg group, higher trough levels were observed in ABI-009 5 mg/kg group (P=0.06) and 10 mg/kg group (P=0.01) (FIG. 18).

In summary, rats were normal post dosing of ABI-009 at current dose regimen (1.7-10 mg/kg, 7 doses), with no body weight loss observed during the study. The histopathology results demonstrated dose-associated local signs of toxicity, with mild to marked necrosis at the highest ABI-009 dose (10 mg/kg). Mixed inflammation cells infiltration may possibly be caused by the heteroprotein HSA. ABI-009 at 1.7 mg/kg (solution concentration 1.7 mg/ml) showed local injection responses similar to saline control. There was no significant drug accumulation following repeated SC injections. Trough blood sirolimus levels increased with higher ABI-009 dose.

The results showed that rats tolerated systemically with multiple doses of ABI-009 over a range of 1.7-10.0 mg/kg with subcutaneous injections. Locally, ABI-009 solution at 1.7 mg/ml concentration was well tolerated. There was no adverse effect observed for this dosage level.

The invention claimed is:

1. A method of treating epilepsy in an individual, comprising systemically administering to the individual an effective amount of a composition comprising nanoparticles comprising albumin-bound sirolimus, wherein the ratio of albumin to sirolimus in the nanoparticles is from about 1:1 to about 9:1.

2. The method of claim 1, wherein the nanoparticle composition is administered once every week, twice every three weeks, or three times every four weeks.

3. The method of claim 1, wherein the average diameter of the nanoparticles in the nanoparticle composition is no greater than about 200 nm.

4. The method of claim 1, wherein the nanoparticle composition is administered to the individual at a dose of about 0.1 mg/m$^2$ to 25 mg/m$^2$.

5. The method of claim 1, wherein the nanoparticle composition is administered to the individual at a dose of about 1 mg/m$^2$ to 10 mg/m$^2$, and wherein the nanoparticle composition is administered once every week, twice every three weeks, or three times every four weeks.

6. The method of claim 1, wherein the nanoparticle composition is administered for at least about one to six cycles, wherein each cycle consists of 21 days or 28 days.

7. The method of claim 1, wherein the individual is a human.

8. The method of claim 1, wherein the nanoparticle composition is parenterally administered into the individual.

9. The method of claim 8, wherein the nanoparticle composition is intravenously administered into the individual.

10. The method of claim 8, wherein the nanoparticle composition is subcutaneously administered into the individual.

11. The method of claim 1, wherein the epilepsy is associated with cortical dysplasia.

12. The method of claim 11, wherein the epilepsy is associated with focal cortical dysplasia.

13. The method of claim 1, wherein the epilepsy is associated with a lesion imaged by magnetic resonance imaging (MRI), or associated with tuberous sclerosis complex (TSC).

14. The method of claim 1, wherein the epilepsy is associated with infantile spasms.

15. The method of claim 14, wherein the epilepsy is surgically refractory epilepsy.

16. The method of claim 1, wherein the epilepsy is metabolic epilepsy, immune epilepsy, or idiopathic localization-related epilepsy with a genetic basis.

17. The method of claim 1, wherein the individual is selected for treatment on the basis of having an mTOR-activation aberration.

18. The method of claim 17, wherein the mTOR-activating aberration comprises an aberration at one or more genes selected from the group consisting of PTEN, TSC1, TSC2, AKT1, MTOR, PI3K, PIK3CA, PIK3CG, RHEB, TP53, NF1, NF2, FGFR4, and BAP1.

19. The method of claim 18, wherein the mTOR-activating aberration comprises a somatic mutation or germline mutation in the one or more genes.

20. The method of claim 18, wherein the mTOR-activating aberration comprises a loss of function mutation or deletion of the one or more genes.

* * * * *